United States Patent
Carrigan et al.

(10) Patent No.: US 9,200,073 B2
(45) Date of Patent: Dec. 1, 2015

(54) DIAGNOSTIC ASSAYS AND KITS FOR DETECTION OF FOLATE RECEPTOR 1

(71) Applicant: ImmunoGen, Inc., Waltham, MA (US)

(72) Inventors: Christina N. Carrigan, Belmont, MA (US); Olga Ab, Millis, MA (US); Daniel Tavares, Natick, MA (US); Beni B. Wolf, Lexington, MA (US)

(73) Assignee: ImmunoGen, Inc., Waltham, MA (US)

( * ) Notice: Subject to any disclaimer, the term of this patent is extended or adjusted under 35 U.S.C. 154(b) by 0 days.

(21) Appl. No.: 14/015,653

(22) Filed: Aug. 30, 2013

(65) Prior Publication Data

US 2014/0099332 A1   Apr. 10, 2014

Related U.S. Application Data

(60) Provisional application No. 61/695,791, filed on Aug. 31, 2012, provisional application No. 61/756,254, filed on Jan. 24, 2013.

(51) Int. Cl.
*C07K 16/28* (2006.01)
*G01N 33/574* (2006.01)
*G01N 33/566* (2006.01)

(52) U.S. Cl.
CPC .............. *C07K 16/28* (2013.01); *G01N 33/566* (2013.01); *G01N 33/57492* (2013.01); *G01N 2333/705* (2013.01)

(58) Field of Classification Search
None
See application file for complete search history.

(56) References Cited

U.S. PATENT DOCUMENTS

| | | | |
|---|---|---|---|
| 5,416,016 A | 5/1995 | Low et al. | |
| 5,720,954 A | 2/1998 | Hudziak et al. | |
| 5,855,866 A | 1/1999 | Thorpe et al. | |
| 6,051,230 A | 4/2000 | Thorpe et al. | |
| 7,033,594 B2 | 4/2006 | Low et al. | |
| 7,112,317 B2 | 9/2006 | Thorpe et al. | |
| 7,125,541 B2 | 10/2006 | Thorpe et al. | |
| 7,740,854 B2 | 6/2010 | Low et al. | |
| 8,557,966 B2 | 10/2013 | Ab et al. | |
| 8,557,996 B2 | 10/2013 | Chaffee et al. | |
| 8,709,432 B2 | 4/2014 | Carrigan et al. | |
| 2003/0028009 A1 | 2/2003 | Huse | |
| 2003/0148406 A1 | 8/2003 | King et al. | |
| 2003/0157090 A1 | 8/2003 | Benvenuto et al. | |
| 2003/0229208 A1 | 12/2003 | Queen et al. | |
| 2003/0233675 A1 | 12/2003 | Cao et al. | |
| 2004/0031072 A1 | 2/2004 | La Rosa et al. | |
| 2004/0087478 A1 | 5/2004 | Gillen et al. | |
| 2004/0157214 A1 | 8/2004 | McCafferty et al. | |
| 2004/0170630 A1 | 9/2004 | Huang et al. | |
| 2004/0180386 A1 | 9/2004 | Carr et al. | |
| 2004/0235840 A1 | 11/2004 | Chari et al. | |
| 2005/0025763 A1 | 2/2005 | Williams et al. | |
| 2005/0244901 A1 | 11/2005 | Peschen et al. | |
| 2006/0030524 A1 | 2/2006 | Cohen et al. | |
| 2006/0110771 A1 | 5/2006 | Katagiri et al. | |
| 2006/0228349 A1 | 10/2006 | Acton et al. | |
| 2006/0239910 A1 | 10/2006 | Nicolaides et al. | |
| 2007/0041985 A1 | 2/2007 | Unger et al. | |
| 2007/0098719 A1 | 5/2007 | Smith et al. | |
| 2007/0099251 A1 | 5/2007 | Zhang et al. | |
| 2007/0231266 A1 | 10/2007 | Low et al. | |
| 2007/0294782 A1 | 12/2007 | Abad et al. | |
| 2008/0081047 A1 | 4/2008 | Berry et al. | |
| 2008/0104734 A1 | 5/2008 | Kav et al. | |
| 2008/0138396 A1 | 6/2008 | Low et al. | |
| 2008/0181888 A1 | 7/2008 | Ambrose et al. | |
| 2008/0227704 A1 | 9/2008 | Kamens | |
| 2008/0260748 A1 | 10/2008 | Iwamoto et al. | |
| 2009/0081710 A1 | 3/2009 | Low et al. | |
| 2009/0104215 A1 | 4/2009 | Ekiel et al. | |
| 2009/0136516 A1 | 5/2009 | Tedder et al. | |
| 2009/0169547 A1 | 7/2009 | Sahin et al. | |
| 2009/0186027 A1 | 7/2009 | Solomon et al. | |
| 2009/0214636 A1 | 8/2009 | Low et al. | |
| 2009/0215165 A1 | 8/2009 | Rance et al. | |
| 2009/0232822 A1 | 9/2009 | Joseloff et al. | |
| 2009/0274697 A1 | 11/2009 | Grasso et al. | |
| 2009/0274713 A1 | 11/2009 | Chari et al. | |
| 2009/0280124 A1 | 11/2009 | Labat et al. | |
| 2009/0280128 A1 | 11/2009 | Kamogawa et al. | |
| 2009/0285795 A1 | 11/2009 | Patell | |
| 2009/0285813 A1 | 11/2009 | Frey et al. | |
| 2009/0317921 A1 | 12/2009 | Groome et al. | |
| 2009/0324491 A1 | 12/2009 | Aburatani et al. | |
| 2009/0324594 A1 | 12/2009 | Nicolaides et al. | |

(Continued)

FOREIGN PATENT DOCUMENTS

| | | |
|---|---|---|
| CN | 101139613 A | 3/2008 |
| CN | 101440130 A | 5/2009 |
| EP | 1 900 752 A1 | 3/2008 |
| EP | 1 864 133 B1 | 3/2010 |
| WO | WO 94/29351 A2 | 12/1994 |
| WO | WO 97/11971 A1 | 4/1997 |
| WO | WO 02/071928 A2 | 9/2002 |
| WO | WO 2004/110498 A1 | 12/2004 |
| WO | WO 2005/003154 A2 | 1/2005 |
| WO | WO 2005/080431 A2 | 9/2005 |

(Continued)

OTHER PUBLICATIONS

Vajdos et al., Comprehensive functional maps of the antigen-binding site of an anti-ErbB2 antibody obtained with shotgun scanning mutagenesis. J. Mol. Biol. 320:415-428, 2002.*

(Continued)

*Primary Examiner* — Ruixiang Li
(74) *Attorney, Agent, or Firm* — Sterne, Kessler, Goldstein & Fox P.L.L.C.

(57) ABSTRACT

The invention generally relates to antibodies that bind to human folate receptor 1 and diagnostic assays for folate receptor 1-based therapies. Methods of using the antibodies to monitor therapy are further provided.

15 Claims, 15 Drawing Sheets

(56) References Cited

U.S. PATENT DOCUMENTS

Figure 1:
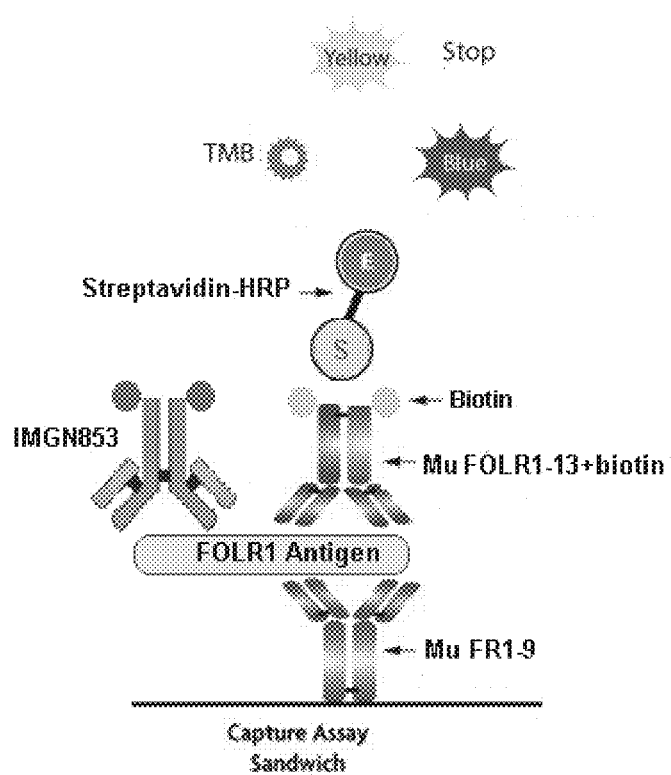

| | | |
|---|---|---|
| 2010/0055034 A1 | 3/2010 | Martin et al. |
| 2010/0086537 A1 | 4/2010 | Sooknanan et al. |
| 2010/0087509 A1 | 4/2010 | Van Rompaey et al. |
| 2010/0104626 A1 | 4/2010 | Leamon et al. |
| 2010/0111852 A1 | 5/2010 | Yoshida |
| 2010/0111866 A1 | 5/2010 | Kratz |
| 2010/0129314 A1 | 5/2010 | Singh et al. |
| 2010/0239581 A1 | 9/2010 | Joseloff et al. |
| 2010/0255479 A1 | 10/2010 | Mikolajczyk et al. |
| 2010/0272741 A1 | 10/2010 | Knutson et al. |
| 2010/0323973 A1 | 12/2010 | Leamon et al. |
| 2010/0330572 A1 | 12/2010 | Assaraf et al. |
| 2011/0059469 A1 | 3/2011 | Aburatani et al. |
| 2011/0195022 A1 | 8/2011 | Deckert et al. |
| 2012/0009181 A1 | 1/2012 | Ab et al. |
| 2012/0177664 A1 | 7/2012 | Yokoseki et al. |
| 2012/0183552 A1 | 7/2012 | Joseloff et al. |
| 2012/0207771 A1 | 8/2012 | O'Shannessy et al. |
| 2012/0253021 A1 | 10/2012 | Li et al. |
| 2012/0259100 A1 | 10/2012 | Jin |
| 2012/0282282 A1 | 11/2012 | Lutz et al. |
| 2013/0295119 A1 | 11/2013 | Ab et al. |
| 2014/0363451 A1 | 12/2014 | Running et al. |

FOREIGN PATENT DOCUMENTS

| | | |
|---|---|---|
| WO | WO 2006/105141 A1 | 10/2006 |
| WO | WO 2006/116592 A2 | 11/2006 |
| WO | WO 2007/006041 A2 | 1/2007 |
| WO | WO 2007/094754 A2 | 8/2007 |
| WO | WO 2007/147265 A1 | 12/2007 |
| WO | WO 2008/021290 A2 | 2/2008 |
| WO | WO 2008/031577 A1 | 3/2008 |
| WO | WO 2008/072723 A1 | 6/2008 |
| WO | WO 2008/101231 A2 | 8/2008 |
| WO | WO 2008/145136 A1 | 12/2008 |
| WO | WO 2009/080759 A1 | 7/2009 |
| WO | WO 2009/087978 A1 | 7/2009 |
| WO | WO 2009/132031 A2 | 10/2009 |
| WO | WO 2010/033733 A1 | 3/2010 |
| WO | WO 2010/111338 A2 | 9/2010 |
| WO | WO 2011/106528 A1 | 9/2011 |
| WO | WO 2012/135675 A2 | 10/2012 |
| WO | WO 2012/138749 A1 | 10/2012 |
| WO | WO 2014/186403 A2 | 11/2014 |

OTHER PUBLICATIONS

Brown et al., Tolerance of single, but not multiple, amino acid replacements in antibody VH CDR 2: a means of minimizing B cell wastage from somatic hypermutation? J. Immunology 156: 3285-3291, 1996.*

Ab, O., et al., "Antibody-Maytansinoid Conjugates Targeting Folate Receptor 1 for Cancer Therapy," *2010 EORTC-NCI-AACR Symposium*—Berlin, Germany (Nov. 16-19, 2010), Abstract 236, 1 Page, American Association for Cancer Research, Germany (distributed in print Nov. 16, 2010; available online Oct. 29, 2010).

Ab, O., et al., "IMGN853, an anti-Folate Receptor I antibody-maytansinoid conjugate for targeted cancer therapy," *102nd Annual AACR Meeting*—Orlando, FL (Apr. 2-6, 2011), Abstract 4576, 1 Page, American Association for Cancer Research, United States (distributed on print Mar. 8, 2011; available online Feb. 25, 2011).

Ab, O., et al., "IMGN853, an anti-Folate Receptor 1 antibody-maytansinoid conjugate for targeted cancer therapy," *102nd Annual AACR Meeting*—Orlando, FL (Apr. 2-6, 2011), Abstract 4576 Poster, American Association for Cancer Research, United States (Apr. 2, 2011).

Armstrong, D.K. et al., "Efficacy and safety of farletuzumab, a humanized monoclonal antibody to folate receptor alpha, in platinum-sensitive relapsed ovarian cancer subjects: preliminary data from a phase-2 study," *Eur. J. Cancer Suppl.* 7:450, Elsevier Science Ltd., England (2009).

Armstrong, D.K., et al., "Exploratory phase II efficacy study of MORAb-003, a monoclonal antibody against folate receptor alpha, in platinum-sensitive ovarian cancer in first relapse," *J. Clin. Oncol. Suppl.* 26:293s, Abstract 8000, American Society of Clinical Oncology, United States (2008).

Bendig, M.M., "Humanization of Rodent Monocloncal Antibodies by CDR Grafting," *METHODS: A Companion to Methods in Enzymology* 8:83-93. Academic Press, Inc., United States (1995).

Cagle, P.T., et al., "Folate Receptor in Adenocarcinoma and Squamous Cell Carcinoma of the Lung: Potential Target for Folate-Linked Therapeutic Agents," *Arch Pathol Lab Med Epub*: 1-4, College of American Pathologists, United States (2012).

Carrigan, C.N., et al., "Evaluation of Folate Receptor 1 (FOLR1) expression by calibrated immunohistochemistry identifies candidate tumor subtypes for targeting by IMGN853, an anti-FOLR1—maytansinoid conjugate," *102nd Annual AACR Meeting*—Orlando FL (Apr. 2-6, 2011), Abstract 3617, 1 Page, American Association for Cancer Research, United States (distributed in print Mar. 8, 2011; available online Feb. 25, 2011).

Carrigan, C.N., et al., "Evaluation Of Folate Receptor 1 (FLOR1) Expression by Calibrated Immunohistochemistry Identifies Candidate Tumor Subtypes for Targeting by IMGN853, an Anti-FOLR1-Maytansinoid Conjugate," *102nd Annual AACR Meeting*—Orlando, FL (Apr. 2-6, 2011), Abstract 3617 Poster, American Association for Cancer Research, United States (Apr. 2, 2011).

Chen, J., et al., "Antibody-cytotoxic agent conjugates for cancer therapy," *Expert Opin. Drug Deliv.* 2(5):873-890, Ashley Publications, England (2005).

Colman, P.M., "Effects of amino acid sequence changes on antibody-antigen interactions," *Research in Immunology* 145:33-36, Elsevier, France (1994).

Colnaghi, M.I., "Generation of Monoclonal Antibodies for In Vivo Approaches," *Nucl. Med. Biol.* 18(1);15-18, Pergamon Press plc. England (1991).

Conde, F.P., et al., "The *Aspergillus* toxin restrictocin is a suitable cytotoxic agent for generation of immunoconjugates with monoclonal antibodies directed against human carcinoma cells," *Eur. J. Biochem.* 178:795-802. Federation of European Biochemical Societies, England (1989).

Coney, L.R. et al., "Chimeric Murine-Human Antibodies Directed against Folate Binding Receptor Are Efficient Mediators of Ovarian Carcinoma Cell Killing," *Cancer Res.* 54:2448-2455. American Association for Cancer Research, United States (1994).

Coney, L.R., et al., "Cloning of a Tumor-associated Antigen: MOv18 and MOv19 Antibodies Recognize a Folate-binding Protein," *Cancer Res.* 51:6125-6132, American Association for Cancer Research, United States (1991).

Copeland, A., et al., "BIG510 (BIG510_9BURK) Unreviewed, UniProtKB/TrEMBL," UniProt, 3 pages, last modified Dec. 14, 2011, accessed at <http://www.uniprot.org/uniprot/BIG510>.

Ebel, W., et al., "Preclinical evaluation of MORAb-003, a humanized monoclonal antibody antagonizing folate receptor-alpha," *Cancer Immun.* 7:6-13, Luigi Grasso, United States (2007).

Ferrini, S., et. al., "Bispecific Monoclonal Antibodies Directed to CD16 and to a Tumor-Associated Antigen Induce Target-Cell Lysis by Resting NK Cells and by a Subset of NK Clones." *Int. J. Cancer* 48:227-233, Wiley-Liss, Inc., United States (1991).

Ferrini, S., et. al., "Retargeting of T-Cell-Receptor Gamma/Delta+Lymphocytes Against Tumor Cells by Bispecific Monoclonal Antibodies. Induction of Cytolytic Activity and Lymphokine Production," *Int. J. Cancer Supplement* 4:53-55, Alan R. Liss, Inc., United States (1989).

Figini, M., et al., "Panning Phage Antibody Libraries on Cells: Isolation of Human Fab Fragments against Ovarian Carcinoma Using Guided Selection," *Cancer Res.* 58:991-996, American Association for Cancer Research, United States (1998).

Franklin, W.A., et al., "New Anti-Lung-Cancer Antibody Cluster 12 Reacts With Human Folate Receptors Present on Adenocarcinoma," *Int. J. Cancer Supplement* 8:89-95, Wiley-Liss, Inc., United States (1994).

(56) References Cited

OTHER PUBLICATIONS

Gould, H.J., et. al., "Comparison of IgE and IgG antibody-dependent cytotoxicity in vitro and in a SCID mouse xenograft model of ovarian carcinoma," *Eur. J. Immunol.* 29:3527-3537, Wiley-VCH Verlag GmbH, Germany (1999).

Hartmann, L.C., et. al., "Folate receptor overexpression is associated with poor outcome in breast cancer," *Int. J. Cancer* 121:938-942, Wiley-Liss, Inc., United States (2007).

Jones, M.B., et al., "Rationale for folate receptor alpha targeted therapy in 'high risk' endometrial carcinomas," *Int. J. Cancer* 123:1699-1703, Wiley-Liss, Inc., United States (2008).

Karagiannis, S. N., et al., "IgE-Antibody-Dependent Immunotherapy of Solid Tumors: Cytotoxic and Phagocytic Mechanisms of Eradication of Ovarian Cancer Cells," *J. Immunol.* 179:2832-2843, American Association of Immunologists, United States (2007).

Ladd, S., et al., "Folate Receptor 1 Immunohistochemistry Repeatability and Stored Slide Antigen Stability," 38$^{th}$ *Annual NSH Symposium* Vancouver, BC Canada (Sep. 28,-Oct. 3, 2012). Abstract, 1 page, National Society for Histotechnology, Canada (2012).

Ladd, S., et. al., "Folate Receptor 1 Immunohistochemistry: Repeatability and Stored Slide Antigen Stability," 38$^{th}$ *Annual NSH Symposium*—Vancouver, BC Canada (Sep. 28,-Oct. 3, 2012), Poster P-38, National Society for Histotechnology, Canada (Sep. 28, 2012).

Lim, J., et. al., "C5A929 (C5A929_BURGB) Unreviewed, UniProtKB/TrEMBL", UniProt, 4 pages, last modified Apr. 18, 2012, accessed at <http://www.uniprot.org/uniprot/C5A929>.

Lu, Y. and Low, P.S., "Immunotherapy of folate receptor-expressing tumors: review of recent advances and future prospects," *Journal of Controlled Release* 91:17-29, Elsevier B.V., Netherlands (2003).

Melani, C., et. al., "Targeting of Interleukin 2 to Human Ovarian Carcinoma by Fusion with a Single-Chain Fv of Antifolate Receptor Antibody," *Cancer Res.* 58:4146-4154, American Association for Cancer Research, United States (1998).

Mezzanzanica, D., et al., "Human Ovarian Carcinoma Lysis by Cytotoxic T Cells Targeted by Bispecific Monoclonal Antibodies: Analysis of the Antibody Components," *Int. J. Cancer* 41:609-615, Alan R. Liss, Inc., United States (1998).

Miotti, S., et al., "Characterization of Human Ovarian Carcinoma-Associated Antigens Defined by Novel Monoclonal Antibodies With Tumor-Restricted Specificity," *Int. J. Cancer* 39:297-303, Alan R, Liss, Inc., United States (1987).

NCL-L-FRalpha, "Novocastra™ Liquid Mouse Monoclonal Antibody Folate Receptor Alpha: Product Code: NCL-L-FRalpha," 40 Pages, Leica Biosystems Newcastle Ltd, England (2009).

Nishiyama, T., et al., "A9SZW6 (A9SZW6_PHYPA) Unreviewed, UniProtKB/TrEMBL," UniProt, 3 pages, last modified Sep. 21, 2011, accessed at <http://www.uniprot.org/uniprot/A9SZW6>.

O'Shannessy, D.J., et al., "Characterization of the Human Folate Receptor Alpha Via Novel Antibody-Based Probes," *Oncotarget* 2(12):1227-1243, Impact Journals, United States (2011).

Pagnelli, G., et al., "Two-step tumour targeting in ovarian cancer patients using biotinylated monoclonal antibodies and radioactive streptavidin," *Eur J Nucl Med.* 19(5):322-329, Springer-Verlag, Germany (1992).

Paul, W.E., eds., "Structure and Function of Immunoglobulins," in *Fundamental Immunology, Third Edition*, pp. 292-295, Raven Press, New York, United States (1993).

Portolano, S., et al., "Lack of Promiscuity in Autoantigen-Specific H and L Chain Combinations as Revealed by Human H and L Chain 'Roulette'," *The Journal of Immunology* 150(3):880-887, The American Association of Immunologists, United States (1993).

Rudikoff, S., et al., "Single amino acid substitution altering antigen-binding specificity," *Proc. Natl. Acad. Sci. USA* 79:1979-1983, National Academy of Sciences, United States (1982).

Scorer, P., et al., "A Full Immunohistochemical Evaluation of a Novel Monoclonal Antibody to Folate Receptor-alpha (FR-α)," *reAGENTS* 3:8-12, Leica Biosystems Newcastle Ltd. United Kingdom (2010).

Singh, R. and Erickson, H.K., "Antibody-Cytotoxic Agent Conjugates: Preparation and Characterization," in *Therapeutics Antibodies: Method and Protocols* Volume 525, Dimitrov, A.S., ed., pp. 445-467, Humans Press, United States (2009).

Smith, A.E., et al., "A Novel Monoclonal Antibody for Detection of Folate Receptor Alpha in Paraffin-Embedded Tissues," *HYBRIDOMA* 26(5):281-288, Mary Ann Liebert, Inc., United States (2007).

Smith-Jones, P.M., et al., "Preclinical Radioimmunotargeting of Folate Receptor Alpha using the Monoclonal Antibody Conjugate DOTA-MORAb-003," *Nucl. Med. Biol.* 35(3):343-351, Elsevier, United States (2008).

Testa, N., et al., "A Method for Quantifying Soluble Folate Receptor 1 in IMGN853 0401 Clinical Trial Patients," *2013 AACR Annual Meeting*—Washington, DC (Apr. 6-10, 2013), Abstract #3503 Poster, American Association of Cancer Research, United States (Apr. 6, 2013).

Testa, N., et al., "A Method for Quantifying Soluble Folate Receptor 1 in IMGN853 0401 Clinical Trial Patients," *2013 AACR Annual Meeting*—Washington, DC (Apr. 6-10, 2013), Abstract #3503, 1 Page, American Association of Cancer Research, United States (submitted Nov. 15, 2012).

Van Dam, G.M., et al., "Intraoperative tumor-specific fluorescence imaging in ovarian cancer by folate receptor-α targeting: first in-human results," *Nature Medicine* 17(10):1315-1320, Nature America, Inc., United States (2011).

Whiteman, K.R., et al., "Preclinical evaluation of IMGN853, an anti-FLOR1 antibody-maytansinoid conjugate, as a potential therapeutic for ovarian cancer," *102nd Annual AACR Meeting*—Orlando, FL (Apr. 2-6, 2011), Abstract 1760, 1 Page, American Association for Cancer Research, United States (distributed in print Mar. 8, 2011; available online Feb. 25, 2011).

Whiteman, K.R., et al., "Preclinical evaluation of IMGN853, an anti-FOLR1 antibody-maytansinoid conjugate, as a potential therapeutic for ovarian caner," *102nd Annual AACR Meeting*—Orlando, FL (Apr. 2-6, 2011), Abstract 1760 Poster, American Association for Cancer Research, United States (Apr. 2, 2011).

Whiteman, K.R., et al., "Anti-tumor activity and pharmacokinetics of the anti-FLOR-1-maytansinoid conjugate IMGN853 is maintained over a wide range of maytansinoid-to-antibody ratios," 103$^{rd}$ *Annual AACR Meeting*—Chicago, IL (Mar. 13,-Apr. 4, 2012), Abstract #4628, 1 page, American Association for Cancer Research, United States (2012).

Whiteman, K.R., et al., "Anti-tumor activity and pharmacokinetics of the anti-FOLR-1-maytansinoid conjugate IMGN853 is maintained over a wide range of maytansiniod-to-antibody ratios," *103nd Annual AACR Meeting*—Chicago, IL (Mar. 31,-Apr. 4, 2012), Abstract #4628 Poster, American Association for Cancer Research, United States (Mar. 31, 2012).

Widdison, W.C., et al., "Semisynthetic Maytansine Analogues for the Targeted Treatment of Cancer," *J. Med. Chem.* 49:4392-4408, American Chemical Society, United States (2006).

Yuan, Y., et al., "Expression of the folate receptor genes *FOLR1* and *FOLR3* differentiates ovarian carcinoma from breast carcinoma and malignant mesothelioma in serious effusions," *Human Pathology* 40:1453-1460, Elsevier Inc., United States (2009).

Zacchetti, A., et al., "$^{177}$Lu-labeled MOv18 as compared to $^{131}$I- or $^{90}$Y-labeled MOv18 has the better therapeutic effect in eradication of alpha folate receptor-expressing tumor xenografts," *Nucl. Med. Biol.* 36:759-770, Elsevier Inc., United States (2009).

English language Abstract of Chinese Patent Publication No. CN 101139613A European Patent Office, espacent database—Worldwide, (2012).

English language Abstract of Chinese Patent Publication No. CN 101440130A, European Patent Office, espacenet database—Worldwide, (2012).

International Search Report for International Application No. PCT/US2011/026079, International Searching Authority, United States, mailed on Aug. 2, 2011.

International Search Report for International Application No. PCT/US2012/032155, International Searching Authority, United States, mailed on Jul. 6, 2012.

(56) References Cited

OTHER PUBLICATIONS

International Search Report for International Application No. PCT/US2012/031544, International Searching Authority, United States, mailed on Sep. 21, 2012.
Supplementary European Search Report for European Application No. EP 11748067.3; The Hague, Netherlands, dated Jun. 26, 2013.
Notice of Allowance, mailed Aug. 8, 2013. in U.S. Appl. No. 13/033,723, filed Feb. 24 2011.
Non-Final Office Action, mailed Apr. 2, 2013, in U.S. Appl. No. 13/435,857, filed Mar. 30, 2012.
Non-Final Office Action, mailed Oct. 11, 2013, in U.S. Appl. No. 13/439,493, filed Apr. 4, 2012.
International Preliminary Report on Patentibility, mailed Oct. 17, 2013, in International application No. PCT/US2012/032155, filed Apr. 4, 2012.
International Preliminary Report on Patentability, mailed Oct. 1, 2013, in International application No. PCT/US2012/031544, filed Mar. 30, 2012.
International Search Report in International Application No. PCT/US2013/057682, International Searching Authority, United States, Alexandria, VA, mailed Jan. 10, 2014.
Final Office Action mailed Dec. 12, 2013, in U.S. Appl. No. 13/435,857, filed Mar. 30, 2012.
Antony, A.C. "Folate Receptors," *Ann Rev Nutr 16*:501-521, Annual Reviews, Inc., United States (1996).
Basal., F., et al., "Functional Folate Receptor Alpha is Elevated in the Blood of Ovarian Cancer Patients," *PLoS ONE* 4(7):e6292, Public Library of Science, United States (2009).
Baselga, J., et al., "Phase II Study of Weekly Intravenous Recombinant Humanized Anti-p185$^{HER2}$ Monoclonal Antibody in Patients With HER2/*neu*-Overexpressing Metastatic Breast Cancer," *J Clin Oncol* 14(3):737-744, American Society of Clinical Oncology, United States (1996).
Mantovani, L.T., et al., "Folate Binding Protein Distribution in Normal Tissues and Biological Fluids from Ovarian Carcinoma Patients as Detected by the Monoclonal Antibodies MOv18 and MOv19," *Eur. J. Cancer* 30A(3):363-369, Pergamon Press, Great Britian (1994).
Tolcher, A., et al., "A Novel Dosing Strategy on Plasma Levels of CanAg in a Phase II Study of IMGN242 (huC242-DM4) in Gastric Cancer," 20$^{th}$ EORTC-NCI-AACR Symposium: Abstract #514, Oct. 21-24, 2008, Geneva, Switzerland (2008).
Notice of Allowance mailed Feb. 18, 2014, in U.S. Appl. No. 13/435,857, Carrigan, C.N., et al., filed Mar. 30, 2012.
Non-Final Office Action mailed Nov. 8, 2012, in U.S. Appl. No. 13/033,723, inventors Ab, O., et al., filed Feb. 24, 2011.
Final Office Action mailed May 1, 2013, in U.S. Appl. No. 13/033,723, inventors Ab, O., et al., filed Feb. 24, 2011.
Co-pending U.S. Appl. No. 14/245,797, inventors Carrigan, C.N., et al., filed Apr. 4, 2014 (Not Published).
Allard, J.E., et al., "Overexpression of folate binding protein is associated with shortened progression-free survival in uterine adenocarcinomas," *Gynecologic Oncology* 107(1):52-57, Academic Press, United States (2007).
Bueno, R., et al., "The α Folate Receptor is Highly Activated in Malignant Pleural Mesothelioma," *The Journal of Thoracic and Cardiovascular Surgery* 121(2):225-233, Mosby, United States (2001).
Chen, Y., et al., "Drug delivery across the blood-brain barrier," *Current Drug Delivery* 1(4):361-376, Bentham Science Publishers, United Arab Emirates (2004).
Farrell, C., et al., "Population pharmacokinetics of farletuzumab, a humanized monoclonal antibody against folate receptor alpha, in epithelial ovarian cancer," *Cancer Chemotherapy and Pharmacology* 70(5):727-734, Springer Verlag, Germany (Nov. 2012, Epub: Sep. 7, 2012).
Figini, M., et al., "Conversion of murine antibodies to human antibodies and their optimization for ovarian cancer therapy targeted to the folate receptor," *Cancer Immunology and Immunotherapy* 58(4):531-546, Springer Verlag, Germany (2009).
Kalli, R.K., et al., "Folate receptor alpha as a tumor target in epithelial ovarian cancer," *Gynecologic Oncology* 108(3):619-626, Academic Press, United States (2008).
Lawson, N. and Scorer, P., "Evaluation of Antibody to Folate Receptor alpha (FR-a)," published online on May 31, 2010, accessed at www.leicabiosystems.com/pathologyleaders/evaluation-of-antibody-to-folate-receptor-alpha-fr-%CE%B1/, accessed on Oct. 27, 2014 (1 page).
Nutt, J.E., et al., "The role of folate receptor alpha (FRα)in the response of malignant pleural mesothelioma to pemetrexed-containing chemotherapy," *British Journal of Cancer* 102(3):553-560, Nature Publishing Group, England (2010).
Office Action mailed Dec. 31, 2014, in U.S. Appl. No. 13/800,835, Ab, O., et al., filed Mar. 13, 2013.
International Search Report for International Application No. PCT/US2014/037911, International Searching Authority, United States, mailed on Oct. 31, 2014.
Supplementary Partial European Report for EP Application No. EP 12 76 4885, The Hague, Netherlands, mailed on Nov. 21, 2014.
Search Report and Written Opinion for SG Patent Application No. 20130770040, Intellectual Property Office of Singapore, Singapore, mailed on Dec. 30, 2014.

* cited by examiner

A

B

A.

B.

SEQUENCE LISTING

<160> NUMBER OF SEQ ID NOS: 49

<210> SEQ ID NO 1
<211> LENGTH: 5
<212> TYPE: PRT
<213> ORGANISM: Artificial Sequence
<220> FEATURE:
<223> OTHER INFORMATION: muFR1-9 (VH-CDR1)

<400> SEQUENCE: 1

Ser Phe Gly Met His
1               5

<210> SEQ ID NO 2
<211> LENGTH: 17
<212> TYPE: PRT
<213> ORGANISM: Artificial Sequence
<220> FEATURE:
<223> OTHER INFORMATION: muFR1-9 (VH-CDR2)

<400> SEQUENCE: 2

Tyr Ile Ser Ser Gly Ser Ser Thr Phe Tyr Tyr Ala Asp Thr Val Lys
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: muFR1-9 (VH-CDR3)

<400> SEQUENCE: 3

Glu Leu Thr Gly Thr Phe Ala Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: muFR1-13 (VH-CDR1)

<400> SEQUENCE: 4

Arg Tyr Ser Val His
1               5

<210> SEQ ID NO 5
<211> LENGTH: 16
<212> TYPE: PRT
<213> ORGANISM: Artificial Sequence
<220> FEATURE:
<223> OTHER INFORMATION: muFR1-13 (VH-CDR2)

<400> SEQUENCE: 5

Met Ile Trp Ser Gly Gly Asn Thr Asp Tyr Asn Ser Val Phe Lys Ser
1               5                   10                  15

<210> SEQ ID NO 6
<211> LENGTH: 10
<212> TYPE: PRT
<213> ORGANISM: Artificial Sequence
<220> FEATURE:
<223> OTHER INFORMATION: muFR1-13 (VH-CDR3)

```
<400> SEQUENCE: 6

Phe Asp Gly Lys Val Ser Trp Phe Ala Tyr
1               5                   10

<210> SEQ ID NO 7
<211> LENGTH: 5
<212> TYPE: PRT
<213> ORGANISM: Artificial Sequence
<220> FEATURE:
<223> OTHER INFORMATION: muFR1-53 (VH-CDR1)

<400> SEQUENCE: 7

Asp Tyr Asp Ile Ser
1               5

<210> SEQ ID NO 8
<211> LENGTH: 17
<212> TYPE: PRT
<213> ORGANISM: Artificial Sequence
<220> FEATURE:
<223> OTHER INFORMATION: muFR1-53 (VH-CDR2)

<400> SEQUENCE: 8

Glu Ile Tyr Pro Gly Ser Gly Arg Thr Tyr Tyr Asn Glu Arg Phe Lys
1               5                   10                  15

Gly

<210> SEQ ID NO 9
<211> LENGTH: 12
<212> TYPE: PRT
<213> ORGANISM: Artificial Sequence
<220> FEATURE:
<223> OTHER INFORMATION: muFR1-53 (VH-CDR3)

<400> SEQUENCE: 9

Ser Tyr Tyr Tyr Gly Thr Asn Ser Pro Phe Ala Tyr
1               5                   10

<210> SEQ ID NO 10
<211> LENGTH: 5
<212> TYPE: PRT
<213> ORGANISM: Artificial Sequence
<220> FEATURE:
<223> OTHER INFORMATION: muFR1-62 (VH-CDR1)

<400> SEQUENCE: 10

Thr Tyr Thr Met His
1               5

<210> SEQ ID NO 11
<211> LENGTH: 17
<212> TYPE: PRT
<213> ORGANISM: Artificial Sequence
<220> FEATURE:
<223> OTHER INFORMATION: muFR1-62 (VH-CDR2)

<400> SEQUENCE: 11

Tyr Ile Asn Pro Thr Ser Gly Tyr Asn Asn Tyr Asn Gln Lys Phe Lys
1               5                   10                  15

Glu

<210> SEQ ID NO 12
<211> LENGTH: 11
<212> TYPE: PRT
<213> ORGANISM: Artificial Sequence
```

<220> FEATURE:
<223> OTHER INFORMATION: muFR1-62 (VH-CDR3)

<400> SEQUENCE: 12

Gly Gly Ala Tyr Gly Arg Arg Pro Val Asp Tyr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: muFR1-9 (VL-CDR1)

<400> SEQUENCE: 13

Arg Ala Ser Gln Ser Ile Asn Asn Asn Leu His
1               5                   10

<210> SEQ ID NO 14
<211> LENGTH: 7
<212> TYPE: PRT
<213> ORGANISM: Artificial Sequence
<220> FEATURE:
<223> OTHER INFORMATION: muFR1-9 (VL-CDR2)

<400> SEQUENCE: 14

Tyr Ala Ser Gln Ser Ile Ser
1               5

<210> SEQ ID NO 15
<211> LENGTH: 10
<212> TYPE: PRT
<213> ORGANISM: Artificial Sequence
<220> FEATURE:
<223> OTHER INFORMATION: muFR1-9 (VL-CDR3)

<400> SEQUENCE: 15

Gln Gln Ser Asn Ser Trp Pro Gln Val Thr
1               5                   10

<210> SEQ ID NO 16
<211> LENGTH: 11
<212> TYPE: PRT
<213> ORGANISM: Artificial Sequence
<220> FEATURE:
<223> OTHER INFORMATION: muFR1-13 (VL-CDR1)

<400> SEQUENCE: 16

Lys Ala Ser Gln Ser Val Ser Asn Asp Val Leu
1               5                   10

<210> SEQ ID NO 17
<211> LENGTH: 7
<212> TYPE: PRT
<213> ORGANISM: Artificial Sequence
<220> FEATURE:
<223> OTHER INFORMATION: muFR1-13 (VL-CDR2)

<400> SEQUENCE: 17

Tyr Ala Tyr Asn Arg Tyr Ser
1               5

<210> SEQ ID NO 18
<211> LENGTH: 9
<212> TYPE: PRT
<213> ORGANISM: Artificial Sequence

```
<220> FEATURE:
<223> OTHER INFORMATION: muFR1-13 (VL-CDR3)

<400> SEQUENCE: 18

Gln Gln Asp His Ser Ser Pro Phe Thr
1               5

<210> SEQ ID NO 19
<211> LENGTH: 11
<212> TYPE: PRT
<213> ORGANISM: Artificial Sequence
<220> FEATURE:
<223> OTHER INFORMATION: muFR1-53 (VL-CDR1)

<400> SEQUENCE: 19

Arg Ala Ser Gln Asp Ile Ser Asn Tyr Leu His
1               5                   10

<210> SEQ ID NO 20
<211> LENGTH: 7
<212> TYPE: PRT
<213> ORGANISM: Artificial Sequence
<220> FEATURE:
<223> OTHER INFORMATION: muFR1-53 (VL-CDR2)

<400> SEQUENCE: 20

Tyr Thr Ser Arg Leu Gln Ser
1               5

<210> SEQ ID NO 21
<211> LENGTH: 9
<212> TYPE: PRT
<213> ORGANISM: Artificial Sequence
<220> FEATURE:
<223> OTHER INFORMATION: muFR1-53 (VL-CDR3)

<400> SEQUENCE: 21

Gln Gln Gly Asn Ser Leu Pro Pro Thr
1               5

<210> SEQ ID NO 22
<211> LENGTH: 11
<212> TYPE: PRT
<213> ORGANISM: Artificial Sequence
<220> FEATURE:
<223> OTHER INFORMATION: muFR1-62 (VL-CDR1)

<400> SEQUENCE: 22

Lys Ala Ser Gln Asn Val Gly Thr Asn Val Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: muFR1-62 (VL-CDR2)

<400> SEQUENCE: 23

Ser Ala Ser Ser Arg Tyr Ser
1               5

<210> SEQ ID NO 24
<211> LENGTH: 9
<212> TYPE: PRT
<213> ORGANISM: Artificial Sequence
```

```
<220> FEATURE:
<223> OTHER INFORMATION: muFR1-62 (VL-CDR3)

<400> SEQUENCE: 24

His Gln Tyr Asn Ser Tyr Pro Tyr Thr
1               5

<210> SEQ ID NO 25
<211> LENGTH: 117
<212> TYPE: PRT
<213> ORGANISM: Artificial Sequence
<220> FEATURE:
<223> OTHER INFORMATION: muFR1-9HCvar

<400> SEQUENCE: 25

Gln Val Gln Leu Val Glu Ser Gly Gly Gly Leu Val Gln Pro Gly Gly
1               5                  10                  15

Ser Arg Lys Leu Ser Cys Ala Ala Ser Gly Phe Thr Phe Ser Ser Phe
                20                  25                  30

Gly Met His Trp Val Arg Gln Ala Pro Glu Lys Gly Leu Glu Trp Val
            35                  40                  45

Ala Tyr Ile Ser Ser Gly Ser Ser Thr Phe Tyr Tyr Ala Asp Thr Val
        50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Leu Thr Gly Thr Phe Ala Tyr Trp Gly Gln Gly Thr Leu
            100                 105                 110

Val Thr Val Ser Ala
        115

<210> SEQ ID NO 26
<211> LENGTH: 118
<212> TYPE: PRT
<213> ORGANISM: Artificial Sequence
<220> FEATURE:
<223> OTHER INFORMATION: muFR1-13HCvar

<400> SEQUENCE: 26

Gln Val Gln Leu Lys Glu Ser Gly Pro Asp Leu Val Ala Pro Ser Gln
1               5                  10                  15

Ser Leu Ser Ile Thr Cys Thr Val Ser Gly Phe Ser Leu Ser Arg Tyr
                20                  25                  30

Ser Val His Trp Ile Arg Gln Pro Pro Gly Lys Gly Leu Glu Trp Leu
            35                  40                  45

Gly Met Ile Trp Ser Gly Gly Asn Thr Asp Tyr Asn Ser Val Phe Lys
        50                  55                  60

Ser Arg Leu Asn Ile Thr Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Thr Phe Asp Gly Lys Val Ser Trp Phe Ala Tyr Trp Gly Gln Gly Thr
            100                 105                 110

Leu Val Thr Val Ser Ala
        115
```

<210> SEQ ID NO 27
<211> LENGTH: 121
<212> TYPE: PRT
<213> ORGANISM: Artificial Sequence
<220> FEATURE:
<223> OTHER INFORMATION: muFR1-53HC

<400> SEQUENCE: 27

Gln Val Gln Leu Gln Gln Ser Gly Pro Glu Leu Val Arg Pro Gly Ala
1               5                   10                  15

Ser Val Lys Met Ser Cys Lys Ala Ser Gly Tyr Lys Phe Thr Asp Tyr
                20                  25                  30

Asp Ile Ser Trp Val Leu Gln Arg Thr Gly Gln Gly Leu Glu Trp Ile
            35                  40                  45

Gly Glu Ile Tyr Pro Gly Ser Gly Arg Thr Tyr Tyr Asn Glu Arg Phe
        50                  55                  60

Lys Gly Lys Ala Thr Leu Thr Ala Asp Lys Ser Ser Asn Thr Val Tyr
65                  70                  75                  80

Met Gln Leu Ser Ser Leu Thr Ser Glu Asp Ser Ala Val Tyr Phe Cys
                85                  90                  95

Ala Ser Ser Tyr Tyr Tyr Gly Thr Asn Ser Pro Phe Ala Tyr Trp Gly
                100                 105                 110

Gln Gly Thr Thr Leu Thr Val Ser Ser
        115                 120

<210> SEQ ID NO 28
<211> LENGTH: 120
<212> TYPE: PRT
<213> ORGANISM: Artificial Sequence
<220> FEATURE:
<223> OTHER INFORMATION: muFR1-62HC

<400> SEQUENCE: 28

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
                20                  25                  30

Thr Met His Trp Val Lys Gln Arg Pro Gly Gln Gly Leu Glu Trp Ile
            35                  40                  45

Ala Tyr Ile Asn Pro Thr Ser Gly Tyr Asn Asn Tyr Asn Gln Lys Phe
        50                  55                  60

Lys Glu Lys Ala Thr Leu Thr Ala Asp Lys Ser Ser Ser Thr Ala Tyr
65                  70                  75                  80

Met Gln Leu Thr Ser Leu Thr Ser Glu Asp Ser Ala Val Tyr Tyr Cys
                85                  90                  95

Ala Ser Gly Gly Ala Tyr Gly Arg Arg Pro Val Asp Tyr Trp Gly Gln
                100                 105                 110

Gly Thr Ser Val Thr Val Ser Ser
        115                 120

<210> SEQ ID NO 29
<211> LENGTH: 109
<212> TYPE: PRT
<213> ORGANISM: Artificial Sequence
<220> FEATURE:
<223> OTHER INFORMATION: muFR1-9LCvar

```
<400> SEQUENCE: 29

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Asn Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Gln
                85                  90                  95

Val Thr Phe Gly Ala Gly Thr Lys Leu Glu Leu Lys Arg
            100                 105

<210> SEQ ID NO 30
<211> LENGTH: 108
<212> TYPE: PRT
<213> ORGANISM: Artificial Sequence
<220> FEATURE:
<223> OTHER INFORMATION: muFR1-13LCvar

<400> SEQUENCE: 30

Ser Ile Val Met Thr Gln Thr Pro Lys Phe Leu Leu Val Ser Thr Gly
1               5                   10                  15

Asp Arg Phe Thr Ile Thr Cys Lys Ala Ser Gln Ser Val Ser Asn Asp
            20                  25                  30

Val Leu Trp Tyr Gln Gln Lys Pro Gly Gln Ser Pro Lys Leu Leu Ile
        35                  40                  45

Tyr Tyr Ala Tyr Asn Arg Tyr Ser Gly Val Pro Asp Arg Phe Thr Gly
    50                  55                  60

Ser Gly Tyr Gly Thr Asp Phe Thr Phe Thr Ile Thr Thr Val Gln Ser
65                  70                  75                  80

Glu Asp Leu Ala Val Tyr Phe Cys Gln Gln Asp His Ser Ser Pro Phe
                85                  90                  95

Thr Phe Gly Ser Gly Thr Lys Leu Glu Ile Lys Arg
            100                 105

<210> SEQ ID NO 31
<211> LENGTH: 108
<212> TYPE: PRT
<213> ORGANISM: Artificial Sequence
<220> FEATURE:
<223> OTHER INFORMATION: muFR1-53LC

<400> SEQUENCE: 31

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu His Trp Tyr Gln Arg Lys Pro Asp Gly Thr Val Lys Leu Leu Val
        35                  40                  45

Tyr Tyr Thr Ser Arg Leu Gln Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80
```

```
Glu Asp Ile Ala Thr Tyr Phe Cys Gln Gln Gly Asn Ser Leu Pro Pro
                85                  90                  95

Thr Phe Gly Ser Gly Thr Lys Leu Glu Ile Lys Arg
            100                 105
```

<210> SEQ ID NO 32
<211> LENGTH: 108
<212> TYPE: PRT
<213> ORGANISM: Artificial Sequence
<220> FEATURE:
<223> OTHER INFORMATION: muFR1-62LC

<400> SEQUENCE: 32

```
Asp Ile Val Met Thr Gln Ser Gln Lys Phe Met Ser Ile Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Thr Leu Ile
        35                  40                  45

Tyr Ser Ala Ser Ser Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys His Gln Tyr Asn Ser Tyr Pro Tyr
                85                  90                  95

Thr Phe Gly Gly Gly Thr Lys Leu Glu Ile Lys Arg
            100                 105
```

<210> SEQ ID NO 33
<211> LENGTH: 441
<212> TYPE: PRT
<213> ORGANISM: Artificial Sequence
<220> FEATURE:
<223> OTHER INFORMATION: muFR1-9HC

<400> SEQUENCE: 33

```
Gln Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Phe Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Glu Leu Thr Gly Thr Phe Ala Tyr Trp Gly Gln Gly Thr Leu
            100                 105                 110

Val Thr Val Ser Ala Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Glu Ser
                165                 170                 175
```

```
Asp Leu Tyr Thr Leu Ser Ser Val Thr Pro Ser Ser Met Arg
            180                 185                 190

Pro Ser Glu Thr Val Thr Cys Asn Val Ala His Pro Ala Ser Ser Thr
            195                 200                 205

Lys Val Asp Lys Lys Ile Val Pro Arg Asp Cys Gly Cys Lys Pro Cys
210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
            245                 250                 255

Val Val Asp Ile Ser Lys Asp Asp Pro Glu Val Gln Phe Ser Trp Phe
            260                 265                 270

Val Asp Asp Val Glu Val His Thr Ala Gln Thr Gln Pro Arg Glu Glu
            275                 280                 285

Gln Phe Asn Ser Thr Phe Arg Ser Val Ser Glu Leu Pro Ile Met His
            290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
            325                 330                 335

Pro Lys Ala Pro Gln Val Tyr Thr Ile Pro Pro Lys Glu Gln Met
            340                 345                 350

Ala Lys Asp Lys Val Ser Leu Thr Cys Met Ile Thr Asp Phe Phe Pro
            355                 360                 365

Glu Asp Ile Thr Val Glu Trp Gln Trp Asn Gly Gln Pro Ala Glu Asn
370                 375                 380

Tyr Lys Asn Thr Gln Pro Ile Met Asn Thr Asn Gly Ser Tyr Phe Val
385                 390                 395                 400

Tyr Ser Lys Leu Asn Val Gln Lys Ser Asn Trp Glu Ala Gly Asn Thr
            405                 410                 415

Phe Thr Cys Ser Val Leu His Glu Gly Leu His Asn His His Thr Glu
            420                 425                 430

Lys Ser Leu Ser His Ser Pro Gly Lys
            435                 440

<210> SEQ ID NO 34
<211> LENGTH: 454
<212> TYPE: PRT
<213> ORGANISM: Artificial Sequence
<220> FEATURE:
<223> OTHER INFORMATION: muFR1-13HC

<400> SEQUENCE: 34

Gln Val Gln Leu Lys Glu Ser Gly Pro Asp Leu Val Ala Pro Ser Gln
1               5                   10                  15

Ser Leu Ser Ile Thr Cys Thr Val Ser Gly Phe Ser Leu Ser Arg Tyr
            20                  25                  30

Ser Val His Trp Ile Arg Gln Pro Pro Gly Lys Gly Leu Glu Trp Leu
            35                  40                  45

Gly Met Ile Trp Ser Gly Gly Asn Thr Asp Tyr Asn Ser Val Phe Lys
        50                  55                  60

Ser Arg Leu Asn Ile Thr Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95
```

Thr Phe Asp Gly Lys Val Ser Trp Phe Ala Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Cys Gly Asp Thr Thr Gly Ser Ser Val Thr Leu Gly
    130                 135                 140

Cys Leu Val Lys Gly Tyr Phe Pro Glu Ser Val Thr Val Thr Trp Asn
145                 150                 155                 160

Ser Gly Ser Leu Ser Ser Ser Val His Thr Phe Pro Ala Leu Leu Gln
                165                 170                 175

Ser Gly Leu Tyr Thr Met Ser Ser Ser Val Thr Val Pro Ser Ser Thr
            180                 185                 190

Trp Pro Ser Gln Thr Val Thr Cys Ser Val Ala His Pro Ala Ser Ser
        195                 200                 205

Thr Thr Val Asp Lys Lys Leu Glu Pro Ser Gly Pro Ile Ser Thr Ile
    210                 215                 220

Asn Pro Cys Pro Pro Cys Lys Glu Cys His Lys Cys Pro Ala Pro Asn
225                 230                 235                 240

Leu Glu Gly Gly Pro Ser Val Phe Ile Phe Pro Pro Asn Ile Lys Asp
                245                 250                 255

Val Leu Met Ile Ser Leu Thr Pro Lys Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
    290                 295                 300

Ser Thr Ile Arg Val Val Ser Thr Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ser Pro Ile Glu Arg Thr Ile Ser Lys Ile Lys Gly Leu Val Arg Ala
            340                 345                 350

Pro Gln Val Tyr Ile Leu Pro Pro Ala Glu Gln Leu Ser Arg Lys
        355                 360                 365

Asp Val Ser Leu Thr Cys Leu Val Val Gly Phe Asn Pro Gly Asp Ile
    370                 375                 380

Ser Val Glu Trp Thr Ser Asn Gly His Thr Glu Glu Asn Tyr Lys Asp
385                 390                 395                 400

Thr Ala Pro Val Leu Asp Ser Asp Gly Ser Tyr Phe Ile Tyr Ser Lys
                405                 410                 415

Leu Asn Met Lys Thr Ser Lys Trp Glu Lys Thr Asp Ser Phe Ser Cys
            420                 425                 430

Asn Val Arg His Glu Gly Leu Lys Asn Tyr Tyr Leu Lys Lys Thr Ile
        435                 440                 445

Ser Arg Ser Pro Gly Lys
    450

<210> SEQ ID NO 35
<211> LENGTH: 445
<212> TYPE: PRT
<213> ORGANISM: Artificial Sequence
<220> FEATURE:
<223> OTHER INFORMATION: muFR1-53HC

```
<400> SEQUENCE: 35

Gln Val Gln Leu Gln Gln Ser Gly Pro Glu Leu Val Arg Pro Gly Ala
1               5                   10                  15

Ser Val Lys Met Ser Cys Lys Ala Ser Gly Tyr Lys Phe Thr Asp Tyr
            20                  25                  30

Asp Ile Ser Trp Val Leu Gln Arg Thr Gly Gln Gly Leu Glu Trp Ile
        35                  40                  45

Gly Glu Ile Tyr Pro Gly Ser Gly Arg Thr Tyr Tyr Asn Glu Arg Phe
    50                  55                  60

Lys Gly Lys Ala Thr Leu Thr Ala Asp Lys Ser Ser Asn Thr Val Tyr
65                  70                  75                  80

Met Gln Leu Ser Ser Leu Thr Ser Glu Asp Ser Ala Val Tyr Phe Cys
                85                  90                  95

Ala Ser Ser Tyr Tyr Tyr Gly Thr Asn Ser Pro Phe Ala Tyr Trp Gly
            100                 105                 110

Gln Gly Thr Thr Leu Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Glu Ser Asp Leu Tyr Thr Leu Ser Ser Ser Val Thr Val Pro
            180                 185                 190

Ser Ser Met Arg Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asn Thr Asn Gly
385                 390                 395                 400

Ser Tyr Phe Val Tyr Ser Lys Leu Asn Val Gln Lys Ser Asn Trp Glu
                405                 410                 415
```

```
                          -continued

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445

<210> SEQ ID NO 36
<211> LENGTH: 444
<212> TYPE: PRT
<213> ORGANISM: Artificial Sequence
<220> FEATURE:
<223> OTHER INFORMATION: muFR1-62HC

<400> SEQUENCE: 36

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Met His Trp Val Lys Gln Arg Pro Gly Gln Gly Leu Glu Trp Ile
        35                  40                  45

Ala Tyr Ile Asn Pro Thr Ser Gly Tyr Asn Asn Tyr Asn Gln Lys Phe
    50                  55                  60

Lys Glu Lys Ala Thr Leu Thr Ala Asp Lys Ser Ser Ser Thr Ala Tyr
65                  70                  75                  80

Met Gln Leu Thr Ser Leu Thr Ser Glu Asp Ser Ala Val Tyr Tyr Cys
                85                  90                  95

Ala Ser Gly Gly Ala Tyr Gly Arg Arg Pro Val Asp Tyr Trp Gly Gln
            100                 105                 110

Gly Thr Ser Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Glu Ser Asp Leu Tyr Thr Leu Ser Ser Ser Val Thr Val Pro Ser
            180                 185                 190

Ser Met Arg Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335
```

```
Lys Gly Arg Pro Lys Ala Pro Gln Val Tyr Thr Ile Pro Pro Pro Lys
                340                 345                 350
Glu Gln Met Ala Lys Asp Lys Val Ser Leu Thr Cys Met Ile Thr Asp
            355                 360                 365
Phe Phe Pro Glu Asp Ile Thr Val Glu Trp Gln Trp Asn Gly Gln Pro
        370                 375                 380
Ala Glu Asn Tyr Lys Asn Thr Gln Pro Ile Met Asn Thr Asn Gly Ser
385                 390                 395                 400
Tyr Phe Val Tyr Ser Lys Leu Asn Val Gln Lys Ser Asn Trp Glu Ala
                405                 410                 415
Gly Asn Thr Phe Thr Cys Ser Val Leu His Glu Gly Leu His Asn His
            420                 425                 430
His Thr Glu Lys Ser Leu Ser His Ser Pro Gly Lys
        435                 440
```

<210> SEQ ID NO 37
<211> LENGTH: 215
<212> TYPE: PRT
<213> ORGANISM: Artificial Sequence
<220> FEATURE:
<223> OTHER INFORMATION: muFR1-9LC

<400> SEQUENCE: 37

```
Asp Ile Val Leu Thr Gln Ser Pro Ala Thr Leu Ser Val Thr Pro Gly
1               5                   10                  15
Asp Ser Val Ser Leu Ser Cys Arg Ala Ser Gln Ser Ile Asn Asn Asn
                20                  25                  30
Leu His Trp Tyr Gln Gln Lys Ser His Glu Ser Pro Arg Leu Leu Ile
            35                  40                  45
Lys Tyr Ala Ser Gln Ser Ile Ser Gly Ile Pro Ser Arg Phe Ser Gly
        50                  55                  60
Ser Gly Ser Gly Thr Asp Phe Thr Leu Ser Ile Asn Ser Val Glu Thr
65                  70                  75                  80
Glu Asp Phe Gly Met Tyr Phe Cys Gln Gln Ser Asn Ser Trp Pro Gln
                85                  90                  95
Val Thr Phe Gly Ala Gly Thr Lys Leu Glu Leu Lys Arg Ala Asp Ala
                100                 105                 110
Ala Pro Thr Val Ser Ile Phe Pro Pro Ser Ser Glu Gln Leu Thr Ser
            115                 120                 125
Gly Gly Ala Ser Val Val Cys Phe Leu Asn Asn Phe Tyr Pro Lys Asp
        130                 135                 140
Ile Asn Val Lys Trp Lys Ile Asp Gly Ser Glu Arg Gln Asn Gly Val
145                 150                 155                 160
Leu Asn Ser Trp Thr Asp Gln Asp Ser Lys Asp Ser Thr Tyr Ser Met
                165                 170                 175
Ser Ser Thr Leu Thr Leu Thr Lys Asp Glu Tyr Glu Arg His Asn Ser
            180                 185                 190
Tyr Thr Cys Glu Ala Thr His Lys Thr Ser Thr Ser Pro Ile Val Lys
        195                 200                 205
Ser Phe Asn Arg Asn Glu Cys
    210                 215
```

<210> SEQ ID NO 38
<211> LENGTH: 214
<212> TYPE: PRT
<213> ORGANISM: Artificial Sequence
<220> FEATURE:
<223> OTHER INFORMATION: muFR1-13LC

<400> SEQUENCE: 38

Ser Ile Val Met Thr Gln Thr Pro Lys Phe Leu Leu Val Ser Thr Gly
1               5                   10                  15

Asp Arg Phe Thr Ile Thr Cys Lys Ala Ser Gln Ser Val Ser Asn Asp
            20                  25                  30

Val Leu Trp Tyr Gln Gln Lys Pro Gly Gln Ser Pro Lys Leu Leu Ile
        35                  40                  45

Tyr Tyr Ala Tyr Asn Arg Tyr Ser Gly Val Pro Asp Arg Phe Thr Gly
    50                  55                  60

Ser Gly Tyr Gly Thr Asp Phe Thr Phe Thr Ile Thr Thr Val Gln Ser
65                  70                  75                  80

Glu Asp Leu Ala Val Tyr Phe Cys Gln Gln Asp His Ser Ser Pro Phe
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 39
<211> LENGTH: 214
<212> TYPE: PRT
<213> ORGANISM: Artificial Sequence
<220> FEATURE:
<223> OTHER INFORMATION: muFR1-53LC

<400> SEQUENCE: 39

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu His Trp Tyr Gln Arg Lys Pro Asp Gly Thr Val Lys Leu Leu Val
        35                  40                  45

Tyr Tyr Thr Ser Arg Leu Gln Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Ser Leu Pro Pro
                85                  90                  95

Thr Phe Gly Ser Gly Thr Lys Leu Glu Ile Lys Arg Ala Asp Ala Ala
            100                 105                 110

```
Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
    210

<210> SEQ ID NO 40
<211> LENGTH: 214
<212> TYPE: PRT
<213> ORGANISM: Artificial Sequence
<220> FEATURE:
<223> OTHER INFORMATION: muFR1-62LC

<400> SEQUENCE: 40

Asp Ile Val Met Thr Gln Ser Gln Lys Phe Met Ser Ile Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Thr Leu Ile
        35                  40                  45

Tyr Ser Ala Ser Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys His Gln Tyr Asn Ser Tyr Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
    210

<210> SEQ ID NO 41
<211> LENGTH: 35
<212> TYPE: DNA
<213> ORGANISM: Artificial Sequence
```

```
<220> FEATURE:
<223> OTHER INFORMATION: EcoMH2
<220> FEATURE:
<221> NAME/KEY: misc_feature
<222> LOCATION: (1)..(35)
<223> OTHER INFORMATION: n is A, C, G, or T
<220> FEATURE:
<221> NAME/KEY: misc_feature
<222> LOCATION: (1)..(35)
<223> OTHER INFORMATION: s is G or C
<220> FEATURE:
<221> NAME/KEY: misc_feature
<222> LOCATION: (1)..(35)
<223> OTHER INFORMATION: m is A or C
<220> FEATURE:
<221> NAME/KEY: misc_feature
<222> LOCATION: (1)..(35)
<223> OTHER INFORMATION: r is A or G
<220> FEATURE:
<221> NAME/KEY: misc_feature
<222> LOCATION: (1)..(35)
<223> OTHER INFORMATION: w is A or T

<400> SEQUENCE: 41
cttccggaat tcsargtnma gctgsagsag tcwgg                                35

<210> SEQ ID NO 42
<211> LENGTH: 36
<212> TYPE: DNA
<213> ORGANISM: Artificial Sequence
<220> FEATURE:
<223> OTHER INFORMATION: BamIgG1

<400> SEQUENCE: 42
ggaggatcca tagacagatg ggggtgtcgt tttggc                               36

<210> SEQ ID NO 43
<211> LENGTH: 31
<212> TYPE: DNA
<213> ORGANISM: Artificial Sequence
<220> FEATURE:
<223> OTHER INFORMATION: SacIMK
<220> FEATURE:
<221> NAME/KEY: misc_feature
<223> OTHER INFORMATION: (1)..(31)
<220> FEATURE:
<221> NAME/KEY: misc_feature
<223> OTHER INFORMATION: (1)..(31)
<220> FEATURE:
<221> NAME/KEY: misc_feature
<223> OTHER INFORMATION: (1)..(31)
<220> FEATURE:
<221> NAME/KEY: misc_feature
<223> OTHER INFORMATION: (1)..(31)
<220> FEATURE:
<221> NAME/KEY: misc_feature
<223> OTHER INFORMATION: (1)..(31)

<400> SEQUENCE: 43
ggagctcgay attgtgmtsa cmcarwctmc a                                    31

<210> SEQ ID NO 44
<211> LENGTH: 46
<212> TYPE: DNA
<213> ORGANISM: Artificial Sequence
<220> FEATURE:
<223> OTHER INFORMATION: HindKL

<400> SEQUENCE: 44
tatagagctc aagcttggat ggtgggaaga tggatacagt tggtgc                    46
```

-continued

```
<210> SEQ ID NO 45
<211> LENGTH: 32
<212> TYPE: DNA
<213> ORGANISM: Artificial Sequence
<220> FEATURE:
<223> OTHER INFORMATION: EcoMH1
<220> FEATURE:
<221> NAME/KEY: misc_feature
<223> OTHER INFORMATION: (1)..(31)
<220> FEATURE:
<221> NAME/KEY: misc_feature
<223> OTHER INFORMATION: (1)..(31)
<220> FEATURE:
<221> NAME/KEY: misc_feature
<222> LOCATION: (1)..(31)
<223> OTHER INFORMATION: n is A, C, G, or T
<220> FEATURE:
<221> NAME/KEY: misc_feature
<222> LOCATION: (1)..(35)
<223> OTHER INFORMATION: s is G or C

<400> SEQUENCE: 45
cttccggaat tcsargtnma gctgsagsag tc                                    32

<210> SEQ ID NO 46
<211> LENGTH: 118
<212> TYPE: PRT
<213> ORGANISM: Artificial Sequence
<220> FEATURE:
<223> OTHER INFORMATION: huMov19 vHC

<400> SEQUENCE: 46
```

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

```
<210> SEQ ID NO 47
<211> LENGTH: 112
<212> TYPE: PRT
<213> ORGANISM: Artificial Sequence
<220> FEATURE:
<223> OTHER INFORMATION: huMov19 vLCv1.00

<400> SEQUENCE: 47
```

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
                20                  25                  30

Gly Thr Ser Leu Met His Trp Tyr His Gln Lys Pro Gly Gln Gln Pro
            35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 48
<211> LENGTH: 112
<212> TYPE: PRT
<213> ORGANISM: Artificial Sequence
<220> FEATURE:
<223> OTHER INFORMATION: huMov19 vLCv1.60

<400> SEQUENCE: 48

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 49
<211> LENGTH: 257
<212> TYPE: PRT
<213> ORGANISM: Homo sapiens

<400> SEQUENCE: 49

Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

-continued

```
Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225             230                 235                 240

Ala Trp Pro Phe Leu Leu Ser Leu Ala Leu Met Leu Leu Trp Leu Leu
                245                 250                 255

Ser
```

DIAGNOSTIC ASSAYS AND KITS FOR DETECTION OF FOLATE RECEPTOR 1

REFERENCE TO RELATED APPLICATIONS

Related applications U.S. 61/695,791, filed Aug. 31, 2012, and U.S. 61/756,254, filed Jan. 24, 2014, are herein incorporated by reference in their entireties.

FIELD OF THE INVENTION

The field of this invention generally relates to antibodies that bind to human folate receptor 1 (FOLR1), methods of detecting FOLR1, methods of diagnosing and treating cancer, and diagnostic assays and kits for FOLR1-based therapies.

BACKGROUND OF THE INVENTION

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which—breast, lung, colorectal, and prostate—account for over half of all new cases (Jemal et al., 2003, Cancer J. Clin. 53:5-26).

Folate Receptor 1 (FOLR1), also known as Folate Receptor-alpha or Folate Binding Protein, is an N-glycosylated protein expressed on plasma membrane of cells. FOLR1 has a high affinity for folic acid and for several reduced folic acid derivatives. FOLR1 mediates delivery of the physiological folate, 5-methyltetrahydrofolate, to the interior of cells.

FOLR1 is overexpressed in the vast majority of ovarian cancers, as well as in many uterine, endometrial, pancreatic, renal, lung, and breast cancers, while the expression of FOLR1 on normal tissues is restricted to the apical membrane of epithelial cells in the kidney proximal tubules, alveolar pneumocytes of the lung, bladder, testes, choroid plexus, and thyroid (Weitman S D, et al., Cancer Res 52: 3396-3401 (1992); Antony A C, Annu Rev Nutr 16: 501-521 (1996); Kalli K R, et al. Gynecol Oncol 108: 619-626 (2008)). This expression pattern of FOLR1 makes it a desirable target for FOLR1-directed cancer therapy.

Because ovarian cancer is typically asymptomatic until advanced stage, it is often diagnosed at a late stage and has poor prognosis when treated with currently available procedures, typically chemotherapeutic drugs after surgical debulking (von Gruenigen V et al., Cancer 112: 2221-2227 (2008); Ayhan A et al., Am J Obstet Gynecol 196: 81 e81-86 (2007); Harry V N et al., Obstet Gynecol Sury 64: 548-560 (2009)). Thus there is a clear unmet medical need for more effective therapeutics for ovarian cancers.

Some previous assays used to detect shed FOLR1 are not sufficiently specific to FOLR1. For example, some assays do not distinguish between FOLR1 and other folate receptor family members (FOLR2, 3, & 4) or report values for total FBP (Folate Binding Protein). Additionally, some assays require that human samples (e.g., plasma) be pre-treated with a light acid wash step to dissociate folic acid from the receptor. Some assay results may also have inaccuracies due to competitive effects between the antibody therapy and diagnostic antibody. Additionally, many commercially available kits are traditionally unreliable both in their reagents, and in their lot-to-lot stability. Evaluations of these kits have given very mixed results, and are intended for research use only. Many require that the human sample be pre-diluted before analysis to reduce the chance of false positives due to the "matrix effect." Thus, there is a clear need for highly sensitive and accurate diagnostic assays as a companion for FOLR1-based therapies.

SUMMARY OF THE INVENTION

The present invention provides methods for detection of FOLR1 in a sample and can be used, for example, to stratify patients. Thus, in one embodiment, the invention provides a method of treating a patient having a folate receptor 1-mediated disease comprising: (a) measuring the shed folate receptor 1 (FOLR1) expression level or FOLR1 on a circulating tumor cell (CTC) in a sample taken from a patient, relative to a shed or CTC FOLR1 level in a reference sample using an antibody or antigen-binding fragment thereof that does not competitively inhibit the binding of the antibody huMov19 to FOLR1; and (b) administering to the patient a fixed dose of an antibody or antigen-binding fragment thereof that modulates FOLR1 activity if the patient's shed or CTC FOLR1 level is elevated; wherein the fixed dose of the antibody or fragment thereof effectively treats the disease or disorder.

In another embodiment, the invention provides a method of treating a patient having a FOLR1-mediated disease or disorder comprising: (a) administering to a patient having a FOLR1-mediated disease or disorder a fixed dose of an antibody or antigen-binding fragment thereof that modulates FOLR1 activity; (b) measuring the patient's shed or CTC FOLR1 expression level relative to the FOLR1 level in a reference sample using an antibody or antigen binding fragment thereof that does not competitively inhibit the binding of the antibody huMov19 to FOLR1; and (c) increasing the amount or frequency of subsequent fixed doses if the patient's shed or CTC FOLR1 level is elevated; wherein an increase (e.g., because increased cell death results in an increased release of shed FOLR1) or decrease in FOLR1 levels of the patient is indicative of treatment efficacy. In another embodiment, the amount or frequency of subsequent fixed doses is increased if the patient's shed or CTC FOLR1 level is decreased.

In another embodiment, the invention provides a method of decreasing FOLR1 expression in a patient comprising: (a) measuring the shed or CTC FOLR1 level in a sample taken from a patient having a FOLR1-mediated disease or disorder, compared to the FOLR1 level in a reference sample using an antibody or antigen-binding fragment thereof that does not competitively inhibit the binding of the antibody huMov19 to FOLR1; and (b) administering to the patient a fixed dose of an antibody or antigen-binding fragment thereof that modulates FOLR1 activity if the patient's shed or CTC FOLR1 level is elevated; wherein the administration of the antibody or antigen-binding fragment thereof increases (e.g., because increased cell death results in an increased release of shed FOLR1) or decreases FOLR1 of the patient.

In another embodiment, the invention provides a method of decreasing FOLR1 expression in a patient comprising: (a) administering to a patient having a FOLR1-mediated disease or disorder a fixed dose of an antibody or antigen-binding fragment thereof that modulates FOLR1 activity; (b) measuring the patient's shed or CTC FOLR1 level relative to the FOLR1 level in a reference sample; and (c) increasing the amount or frequency of subsequent fixed doses if the patient's shed or CTC FOLR1 level is elevated; wherein the administration of the antibody or antigen-binding fragment thereof increases (e.g., because increased cell death results in an increased release of shed FOLR1) or decreases FOLR1 levels in the patient.

In one embodiment, the disease is cancer. In another embodiment, the cancer is a FOLR1 elevated cancer selected from the group consisting of: ovarian, non-small cell lung cancer, uterine, endometrial, pancreatic, renal, lung, and breast cancer. In another embodiment, the cancer is ovarian cancer that is platinum resistant or platinum refractory.

The invention also provides a method of monitoring therapeutic efficacy of a fixed dose of an antibody or antigen-binding fragment thereof that modulates FOLR1 activity in a patient comprising: (a) measuring a first shed or CTC FOLR1 level in a sample taken from a patient having a FOLR1-mediated disease or disorder using an antibody or antigen-binding fragment thereof that does not competitively inhibit the binding of the antibody huMov19 to FOLR1; (b) administering to the patient a fixed dose of an antibody or antigen-binding fragment thereof that modulates FOLR1 activity; (c) measuring a second shed or CTC FOLR1 level in a sample taken from the patient following antibody administration using an antibody or antigen-binding fragment thereof that does not competitively inhibit the binding of the antibody huMov19 to FOLR1; and (d) comparing the second FOLR1 level to the first FOLR1 level; wherein an increase (e.g., because increased cell death results in an increased release of shed FOLR1) or decrease between the first and second FOLR1 scores indicates therapeutic efficacy.

In one embodiment, the FOLR1 expression level is measured in a bodily fluid. In another embodiment, the bodily fluid is ascites fluid. In another embodiment, the bodily fluid is serum, blood, or plasma. In another embodiment, the FOLR1 expression level is measured in a peripheral blood sample.

In one embodiment, the patient has cancer. In another embodiment, the cancer is a FOLR1 elevated cancer selected from the group consisting of ovarian, non-small cell lung cancer, uterine, endometrial, pancreatic, renal, lung, and breast cancer. In another embodiment, the cancer is ovarian cancer that is platinum resistant or platinum refractory.

In one embodiment, the FOLR1 expression is measured using at least one additional anti-FOLR1 antibody or antigen-binding fragment thereof. In another embodiment, the FOLR1 expression is measured using two anti-FOLR1 antibodies or antigen-binding fragments thereof. In another embodiment, the In another embodiment, the antibody is a murine, chimeric, humanized, or human antibody. In another embodiment, the antibody or antigen-binding fragment thereof binds to a human folate receptor 1 with a Kd of about 1.0 to about 10 nM. In another embodiment, the antibody or antigen-binding fragment thereof binds to a human folate receptor 1 with a Kd of about 0.5 nM to about 5 nM. In another embodiment, the binding affinity is measured by cytometry, Biacore, ELISA, or radioimmunoassay. In another embodiment, the cytometry is flow cytometry.

In one embodiment, the antibody or antigen-binding fragment thereof does not bind folate receptor 2 or folate receptor 3.

In one embodiment, the at least one antibody or antigen-binding fragment thereof is bound to a solid support. In another embodiment, the at least one antibody or antigen-binding fragment thereof is bound to a microtiter plate. In another embodiment, the at least one antibody or antigen-binding fragment thereof comprises a detection agent. In another embodiment, the detection agent is a chromogenic detection agent, a fluorogenic detection agent, an enzymatic detection agent, or an electrochemiluminescent detection agent. In another embodiment, the detection agent is horseradish peroxidase (HRP).

In one embodiment, the FOLR1 levels are determined using an enzyme linked immunosorbent assay (ELISA), or cytometry (e.g., flow cytometry). In another embodiment, the ELISA is a sandwich ELISA.

In one embodiment, the at least one antibody or antigen-binding fragment thereof specifically binds to the same FOLR1 epitope as an antibody selected from the group consisting of: (a) an antibody comprising the polypeptide of SEQ ID NO:25 and the polypeptide of SEQ ID NO:29; (b) an antibody comprising the polypeptide of SEQ ID NO:26 and the polypeptide of SEQ ID NO:30; (c) an antibody comprising the polypeptide of SEQ ID NO:27 and the polypeptide of SEQ ID NO:31; and (d) an antibody comprising the polypeptide of SEQ ID NO:28 and the polypeptide of SEQ ID NO:32.

In one embodiment, the at least one antibody or antigen-binding fragment thereof specifically binds to FOLR1, wherein the antibody or fragment thereof competitively inhibits FOLR1 binding of an antibody selected from the group consisting of: (a) an antibody comprising the polypeptide of SEQ ID NO:25 and the polypeptide of SEQ ID NO:29; (b) an antibody comprising the polypeptide of SEQ ID NO:26 and the polypeptide of SEQ ID NO:30; (c) an antibody comprising the polypeptide of SEQ ID NO:27 and the polypeptide of SEQ ID NO:31; and (d) an antibody comprising the polypeptide of SEQ ID NO:28 and the polypeptide of SEQ ID NO:32.

In one embodiment, the at least one antibody or antigen-binding fragment thereof specifically binds to FOLR1, wherein the antibody comprises polypeptide sequences selected from the group consisting of: (a) SEQ ID NOs: 1, 2, and 3 and SEQ ID NOs: 13, 14, and 15; (b) SEQ ID NOs: 4, 5, and 6 and SEQ ID NOs: 16, 17, and 18; (c) SEQ ID NOs: 7, 8, and 9 and SEQ ID NOs: 19, 20, and 21; (d) SEQ ID NOs: 10, 11, and 12 and SEQ ID NOs: 22, 23, and 24; and (e) variants of (a) to (d) comprising 1, 2, 3, or 4 conservative amino acid substitutions.

In one embodiment, the at least one antibody or antigen-binding fragment thereof is detectably labeled.

In one embodiment, the administered antibody comprises the FOLR1 antibody huMov19.

In one embodiment, the huMov19 is administered as an antibody maytansinoid conjugate. In one embodiment the antibody maytansinoid conjugate comprises the maytansinoid DM4 and the cleavable sulfo-SPDB linker (IMGN853).

The invention also provides a method of treating a patient having a FOLR1-mediated disease or disorder comprising: (a) administering to a patient having a FOLR1-mediated disease or disorder a fixed dose of an antibody or antigen-binding fragment thereof that modulates FOLR1 activity; (b) submitting a sample taken from the patient for measurement of a FOLR1 expression level; (c) determining from the results of the measurement whether the patient's shed or CTC FOLR1 level is elevated relative to the FOLR1 level in a reference sample; and, (d) increasing the amount or frequency of subsequent fixed doses if the patient's shed or CTC FOLR1 level is elevated.

The invention also provides a method of treating a patient having a FOLR1-mediated disease or disorder comprising: (a) administering to a patient having a FOLR1-mediated disease or disorder a fixed dose of an antibody or antigen-binding fragment thereof that modulates FOLR1 activity; (b) submitting a sample taken from the patient for measurement of a shed or CTC FOLR1 level and comparison to a FOLR1 level in a reference sample; and (c) increasing the amount or frequency of subsequent fixed doses if the patient's shed or CTC FOLR1 level is elevated; wherein an increase (e.g., because increased cell death results in an increased release of shed FOLR1) or decrease in the FOLR1 levels of the patient is indicative of treatment efficacy.

In one embodiment, the administered antibody comprises the FOLR1 antibody huMov19. In another embodiment, the huMov19 is administered as an antibody maytansinoid conjugate. In one embodiment the antibody maytansinoid conjugated comprises the maytansinoid DM4 and the cleavable sulfo-SPDB linker (IMGN853).

The invention also provides a method of treating a patient having a FOLR1-mediated disease or disorder comprising: (a) obtaining a sample from a patient having a FOLR1-mediated disease or disorder, where the patient has received a fixed dose of an antibody or antigen-binding fragment thereof that modulates FOLR1 activity; (b) measuring a shed or CTC FOLR1 level from the sample using an antibody or antigen-binding fragment thereof that does not competitively inhibit the binding of the antibody huMov19 to FOLR1; (c) determining whether the patient's shed or CTC FOLR1 level is elevated relative to a FOLR1 level in a reference sample; (d) instructing a healthcare provider to increase the amount or frequency of subsequent fixed doses if the patient's shed or CTC FOLR1 level is elevated; wherein an increase (e.g., because increased cell death results in an increased release of shed FOLR1) or decrease in the FOLR1 of the patient is indicative of treatment efficacy.

The invention also provides an immunoassay kit for detecting shed or CTC FOLR1 in a sample, the kit comprising: (a) a capture antibody against human FOLR1, wherein the capture antibody or antigen-binding fragment thereof does not competitively inhibit the binding of huMov19 to FOLR1, and (b) a detection reagent. In another embodiment, the kit further comprises a solid support for the capture reagent. In another embodiment, the capture reagent is immobilized on the solid support. In another embodiment, the capture reagent is coated on a microtiter plate. In another embodiment, the detection reagent is a second FOLR1 antibody. In another embodiment, the first and/or second FOLR1 antibody comprises polypeptide sequences selected from the group consisting of: (a) SEQ ID NOs: 1, 2, and 3 and SEQ ID NOs: 13, 14, and 15; (b) SEQ ID NOs: 4, 5, and 6 and SEQ ID NOs: 16, 17, and 18; (c) SEQ ID NOs: 7, 8, and 9 and SEQ ID NOs: 19, 20, and 21; (d) SEQ ID NOs: 10, 11, and 12 and SEQ ID NOs: 22, 23, and 24; and (e) variants of (a) to (d) comprising 1, 2, 3, or 4 conservative amino acid substitutions.

In one embodiment, the detection reagent is detected using a species specific antibody. In another embodiment, the kit further comprises a detection means for the detectable antibodies. In another embodiment, the detection means is colorimetric. In another embodiment, the kit further comprises a FOLR1 polypeptide as an antigen standard. In another embodiment, the FOLR1 polypeptide is FOLR1-Fc.

The invention also provides an antibody or antigen-binding fragment thereof that specifically binds to the same FOLR1 epitope as an antibody selected from the group consisting of: (a) an antibody comprising the polypeptide of SEQ ID NO:25 and the polypeptide of SEQ ID NO:29; (b) an antibody comprising the polypeptide of SEQ ID NO:26 and the polypeptide of SEQ ID NO:30; (c) an antibody comprising the polypeptide of SEQ ID NO:27 and the polypeptide of SEQ ID NO:31; and (d) an antibody comprising the polypeptide of SEQ ID NO:28 and the polypeptide of SEQ ID NO:32.

The invention also provides an antibody or antigen-binding fragment thereof that specifically binds to FOLR1, wherein the antibody or fragment thereof competitively inhibits binding to FOLR1 of an antibody selected from the group consisting of: (a) an antibody comprising the polypeptide of SEQ ID NO:25 and the polypeptide of SEQ ID NO:29; (b) an antibody comprising the polypeptide of SEQ ID NO:26 and the polypeptide of SEQ ID NO:30; (c) an antibody comprising the polypeptide of SEQ ID NO:27 and the polypeptide of SEQ ID NO:31; and (d) an antibody comprising the polypeptide of SEQ ID NO:28 and the polypeptide of SEQ ID NO:32.

The invention also provides an antibody or antigen-binding fragment thereof that specifically binds to FOLR1, wherein the antibody comprises polypeptide sequences selected from the group consisting of: (a) SEQ ID NOs: 1, 2, and 3 and SEQ ID NOs: 13, 14, and 15; (b) SEQ ID NOs: 4, 5, and 6 and SEQ ID NOs: 16, 17, and 18; (c) SEQ ID NOs: 7, 8, and 9 and SEQ ID NOs: 19, 20, and 21; (d) SEQ ID NOs: 10, 11, and 12 and SEQ ID NOs: 22, 23, and 24; and (e) variants of (a) to (d) comprising 1, 2, 3, or 4 conservative amino acid substitutions.

In one embodiment, the antibody comprises polypeptide sequences that are at least 90% identical to polypeptide sequences selected from the group consisting of: (a) SEQ ID NO:25 and SEQ ID NO:29; (b) SEQ ID NO:26 and SEQ ID NO:30; (c) SEQ ID NO:27 and SEQ ID NO:31; and (d) SEQ ID NO:28 and SEQ ID NO:32. In another embodiment, the polypeptide sequences are at least 95% identical to polypeptide sequences selected from the group consisting of: (a) SEQ ID NO:25 and SEQ ID NO:29; (b) SEQ ID NO:26 and SEQ ID NO:30; (c) SEQ ID NO:27 and SEQ ID NO:31; and (d) SEQ ID NO:28 and SEQ ID NO:32. In another embodiment, the polypeptide sequences are at least 99% identical to polypeptide sequences selected from the group consisting of: (a) SEQ ID NO:25 and SEQ ID NO:29; (b) SEQ ID NO:26 and SEQ ID NO:30; (c) SEQ ID NO:27 and SEQ ID NO:31; and (d) SEQ ID NO:28 and SEQ ID NO:32.

In one embodiment, the antibody or antigen-binding fragment thereof is murine, non-human, humanized, chimeric, resurfaced, or human. In another embodiment, the antibody binds to human FOLR1 but not FOLR2 or FOLR3. In another embodiment, the antibody is a full length antibody or an antigen-binding fragment. In another embodiment, the antibody or antigen-binding fragment thereof comprises a Fab, Fab', F(ab')2, Fd, single chain Fv or scFv, disulfide linked Fv, V-NAR domain, IgNar, intrabody, IgGΔCH2, minibody, F(ab')3, tetrabody, triabody, diabody, single-domain antibody, DVD-Ig, Fcab, mAb2, (scFv)2, or scFv-Fc.

The invention also provides a polypeptide that specifically binds FOLR1, wherein the polypeptide comprises sequences selected from the group consisting of: (a) SEQ ID NOs: 1, 2, and 3 and SEQ ID NOs: 13, 14, and 15; (b) SEQ ID NOs: 4, 5, and 6 and SEQ ID NOs: 16, 17, and 18; (c) SEQ ID NOs: 7, 8, and 9 and SEQ ID NOs: 19, 20, and 21; (d) SEQ ID NOs: 10, 11, and 12 and SEQ ID NOs: 22, 23, and 24; and (e) variants of (a) to (d) comprising 1, 2, 3, or 4 conservative amino acid substitutions. In another embodiment, the polypeptide comprises sequences that are at least 90% identical to sequences selected from the group consisting of: (a) SEQ ID NO:25 and SEQ ID NO:29; (b) SEQ ID NO:26 and SEQ ID NO:30; (c) SEQ ID NO:27 and SEQ ID NO:31; and (d) SEQ ID NO:28 and SEQ ID NO:32. In another embodiment, the sequences are at least 95% identical to sequences selected from the group consisting of: (a) SEQ ID NO:25 and SEQ ID NO:29; (b) SEQ ID NO:26 and SEQ ID NO:30; (c) SEQ ID NO:27 and SEQ ID NO:31; and (d) SEQ ID NO:28 and SEQ ID NO:32. In another embodiment, the sequences are at least 99% identical to sequences selected from the group consisting of: (a) SEQ ID NO:25 and SEQ ID NO:29; (b) SEQ ID NO:26 and SEQ ID NO:30; (c) SEQ ID NO:27 and SEQ ID NO:31; and (d) SEQ ID NO:28 and SEQ ID NO:32.

In one embodiment, the antibody or polypeptide binds to a human folate receptor 1 with a Kd of about 1.0 to about 10 nM. In another embodiment, the antibody or polypeptide binds to a human folate receptor 1 with a Kd of about 1.0 nM or better. In another embodiment, the binding affinity is measured by cytometry, Biacore, ELISA, or radioimmunoassay. In another embodiment, the cytometry is flow cytometry.

The invention also provides a method of detecting FOLR1 expression in a sample comprising contacting the sample with an antibody or antigen-binding fragment thereof or polypeptide of the invention. In another embodiment, the antibody or antigen-binding fragment thereof is detectably labeled. In another embodiment, the label is selected from the group consisting of immunofluorescent label, chemiluminescent label, phosphorescent label, enzyme label, radiolabel, avidin/biotin, colloidal gold particles, colored particles and magnetic particles. In another embodiment, the FOLR1 expression is determined by radioimmunoassay, Western blot assay, immunofluorescent assay, enzyme immunoassay, immunoprecipitation assay, chemiluminescent assay, or immunohistochemical assay. In another embodiment, the FOLR1 expression is determined using a circulating tumor cell (CTC) assay where the CTCs are enriched from a sample of blood, plasma, or serum and stained for FOLR1 expression using an antibody or antigen-binding fragment thereof of the invention. Non-limiting examples of antibodies useful for the CTC assay include FR1-9 and FR1-13. CTC assays using the antibodies of the present invention may be useful for identifying a subject as likely to respond to a FOLR1-based therapy.

The invention also provides an isolated cell producing an antibody or antigen-binding fragment thereof or polypeptide of the invention.

The inventions also provides a method of making an antibody or antigen-binding fragment thereof, or polypeptide of the invention comprising (a) culturing a cell expressing the antibody or antigen-binding fragment thereof, or polypeptide of the invention.

The invention also provides an active agent comprising an antibody or antigen-binding fragment thereof that modulates FOLR1 activity for use in a method for treating cancer, wherein increased expression of FOLR1 protein has been measured in a cancerous sample from the subject using an antibody, antigen-binding fragment thereof, or polypeptide provided herein prior to administration of the active agent.

The invention also provides an active agent comprising an antibody or antigen-binding fragment thereof thereof that modulates FOLR1 activity for use in a method for treating a FOLR1-mediated disease or disorder, comprising: (a) measuring the FOLR1 protein level in a patient sample using an antibody, antigen-binding fragment thereof, or polypeptide provided here; and (b) administering to the patient a fixed dose of the active agent if the patient's FOLR1 protein level is elevated relative to a reference FOLR1 protein level.

The invention also provides an active agent comprising an antibody or antigen-binding fragment thereof that modulates FOLR1 activity for use in a method for treating a FOLR1-mediated disease or disorder, comprising: (a) administering to a patient having a FOLR1-mediated disease or disorder a fixed dose of the active agent; (b) measuring the patient's FOLR1 protein level using the antibody, antigen-binding fragment thereof, or polypeptide provided herein; and (c) increasing the amount or frequency of subsequent fixed doses if the patient's FOLR1 protein level is elevated relative to a reference FOLR1 protein level.

The invention also provides an active agent comprising an antibody or antigen-binding fragment thereof that modulates FOLR1 activity for use in a method for treating a FOLR1-mediated disease or disorder, wherein (a) the FOLR1 protein level measured in a sample taken from a patient is compared a reference FOLR1 protein level using an antibody, antigen-binding fragment thereof, or polypeptide provided herein; and (b) a fixed dose of the active agent is administered if the patient's FOLR1 protein level is elevated relative to the reference FOLR1 protein level, wherein the administration of the active agent decreases the FOLR1 protein level.

The invention also provides an active agent comprising an antibody or antigen-binding fragment thereof that modulates FOLR1 activity for use in a method for treating a FOLR1-mediated disease or disorder, wherein FOLR1-expressing cells in a patient are decreased, wherein (a) a fixed dose of the active agent is administered to the patient; (b) the FOLR1 protein level measured in a sample obtained from the patient is compared to a reference FOLR1 protein level using an antibody, antigen-binding fragment thereof, or polypeptide provided herein; and (c) the amount or frequency of subsequent fixed doses is increased if the patient's FOLR1 protein level is elevated relative to the reference FOLR1 protein level; wherein the administration of the active agent decreases the FOLR1 protein level.

The invention also provides an active agent comprising an antibody or antigen-binding fragment thereof that modulates FOLR1 activity for use in a method for monitoring the therapeutic efficacy of a fixed dose of the active agent in a patient comprising: (a) measuring a first FOLR1 protein level in a sample from a patient having a FOLR1-mediated disease or disorder using an antibody, antigen-binding fragment thereof, or polypeptide provided herein; (b) administering to the patient a fixed dose of the active agent; (c) measuring a second FOLR1 protein level in a sample taken from the patient following active agent administration using an antibody, antigen-binding fragment thereof, or polypeptide provided herein; and (d) comparing the second FOLR1 protein level to the first FOLR1 protein level; wherein a decrease between the first and second FOLR1 protein levels indicates therapeutic efficacy.

The invention also provides an active agent comprising an antibody or antigen-binding fragment thereof that modulates FOLR1 activity for use in a method for treating a FOLR1-mediated disease or disorder in a patient, comprising: (a) administering a fixed dose of the active agent to a patient having a FOLR1-mediated disease or disorder; (b) submitting a sample taken from the patient for measurement of a FOLR1 protein level using an antibody, antigen-binding fragment thereof, or polypeptide provided herein; (c) determining from the results of the measurement whether the patient's FOLR1 protein level is elevated relative to a reference FOLR1 protein level; and, (d) increasing the amount and/or frequency of subsequent fixed doses if the patient's FOLR1 protein level is elevated relative to the reference FOLR1 protein level.

The invention also provides an active agent comprising an antibody or antigen-binding fragment thereof that modulates FOLR1 activity for use in a method for treating a FOLR1-mediated disease or disorder, comprising: (a) administering a fixed dose of the active agent to a patient having a FOLR1-mediated disease or disorder; (b) submitting a sample taken from the patient for measurement of a FOLR1 protein level using an antibody, antigen-binding fragment thereof, or polypeptide provided herein and comparison of the measured FOLR1 protein level to a reference FOLR1 protein level; and (c) increasing the amount or frequency of subsequent fixed doses if the patient's FOLR1 protein level is elevated relative to the reference FOLR1 protein level; wherein a decrease in the FOLR1 levels of the patient is indicative of treatment efficacy.

The invention also provides an active agent comprising an antibody or antigen-binding fragment thereof that modulates FOLR1 activity for use in a method for treating a FOLR1-mediated disease or disorder, comprising: (a) obtaining a sample from a patient having a FOLR1-mediated disease or disorder, where the patient has received a fixed dose of the active agent; (b) measuring a FOLR1 protein level from the sample using an antibody, antigen-binding fragment thereof, or polypeptide provided herein; (c) determining whether the patient's FOLR1 protein level is elevated relative to a a reference FOLR1 protein level; (d) increasing or instructing a healthcare provider to increase the amount and/or frequency of subsequent fixed doses if the patient's FOLR1 protein level is elevated relative to the reference FOLR1 protein level; wherein a decrease in the FOLR1 of the patient is indicative of treatment efficacy.

The invention also provides an active agent comprising an antibody or antigen-binding fragment thereof that modulates FOLR1 activity for use in a method for treating a FOLR1-mediated disease or disorder wherein increased expression of FOLR1 has been measured in a sample from the subject using an antibody, antigen-binding fragment thereof, or polypeptide provided herein prior to administration of the active agent.

In some embodiments, the measured FOLR1 protein is shed FOLR1. In some embodiments, the measured FOLR1 protein is on a circulating tumor cell.

In some embodiments, the FOLR1 protein level is measured in a bodily fluid. In some embodiments, the bodily fluid is ascites fluid. In some embodiments, the bodily fluid is serum, blood, or plasma. In some embodiments, the FOLR1 protein level is measured in a peripheral blood sample.

In some embodiments, the patient has cancer. In some embodiments, the FOLR1-mediated disease or disorder is cancer. In some embodiments, the cancer is a FOLR1 elevated cancer selected from the group consisting of: ovarian, non-small cell lung cancer, uterine, endometrial, pancreatic, renal, lung, and breast cancer. In some embodiments, the ovarian cancer is platinum resistant or platinum refractory. In some embodiments, the lung cancer is non-small cell lung cancer (NSCLC). In some embodiments, the cancer is endometrial cancer.

In some embodiments, the FOLR1 protein level is measured using two different antibodies or antigen-binding fragments thereof or polypeptides specifically binding FOLR1. In some embodiments, the antibody, antigen-binding fragment thereof, or polypeptide used to detect FOLR1 protein is bound to a solid support. In some embodiments, the solid support is a microtiter plate.

In some embodiments, the antibody, antigen-binding fragment thereof, or polypeptide used to detect FOLR1 protein comprises a detection agent. In some embodiments, the detection agent is a chromogenic detection agent, a fluorogenic detection agent, an enzymatic detection agent, or an electrochemiluminescent detection agent. In some embodiments, the detection agent is horseradish peroxidase (HRP).

In some embodiments, the FOLR1 protein levels are determined using an enzyme linked immunosorbent assay (ELISA). In some embodiments, the ELISA is a sandwich ELISA.

In some embodiments, the active agent comprises the FOLR1 antibody huMov19. In some embodiments, the huMov19 is conjugated to a cytotoxic agent. In some embodiments, the huMov19 is administered as an antibody maytansinoid conjugate further comprising the maytansinoid DM4 and the cleavable sulfo-SPDB linker (IMGN853).

The invention also provides an antibody, antigen-binding fragment thereof, or polypeptide provided herein for use as a diagnostic.

The invention also provides an antibody, antigen-binding fragment thereof, or polypeptide provided in, e.g., an antibody or antigen-binding-fragment thereof that does not competitively inhibit the binding to FOLR1 of an active agent comprising an antibody or antigen-binding fragment thereof that modulates FOLR1 activity, for use in the treatment of a FOLR1-mediated disease or disorder with an active agent comprising an antibody or antigen-binding fragment thereof that modulates FOLR1 activity and/or for monitoring therapeutic efficacy of a fixed dose of an active agent comprising an antibody or antigen-binding fragment thereof that modulates FOLR1 activity.

The invention also provides, an antibody, antigen-binding fragment thereof, or polypeptide provided herein is for use in a method of diagnosing (i) a FOLR1-mediated disease or disorder and/or (ii) the response to the treatment of a FOLR1-mediated disease or disorder with a fixed dose of an active agent comprising an antibody or antigen-binding fragment thereof that modulates FOLR1 activity and/or (iii) the therapeutic efficacy of a treatment with a fixed dose of an active agent comprising an antibody or antigen-binding fragment thereof that modulates FOLR1 activity. In some embodiments, the antibody, antigen-binding fragment thereof, or polypeptide is for use in a method for diagnosing cancer in a patient suffering therefrom. In some embodiments, the cancer is associated with elevated levels of FOLR1. In some embodiments, the antibody, antigen-binding fragment thereof, or polypeptide comprises a detection agent. In some embodiments, the detection agent is a chromogenic detection agent, a fluorogenic detection agent, an enzymatic detection agent, or an electrochemiluminescent detection agent.

The invention also provides methods wherein the FOLR-1 mediated disease is cancer, wherein the active agent comprises IMGN853, and wherein the shed FOLR1 protein level is measured using an ELISA assay using at least two anti-FOLR1 antibodies that do not competitively inhibit the binding of the active agent to FOLR1, wherein each of the at least two anti-FOLR1 comprise amino acid sequences selected from the group consisting of: (a) SEQ ID NOs: 1, 2, and 3 and SEQ ID NOs: 13, 14, and 15; (b) SEQ ID NOs: 4, 5, and 6 and SEQ ID NOs: 16, 17, and 18; (c) SEQ ID NOs: 7, 8, and 9 and SEQ ID NOs: 19, 20, and 21; and (d) SEQ ID NOs: 10, 11, and 12 and SEQ ID NOs: 22, 23, and 24.

The invention also provides methods wherein the FOLR-1 mediated disease is cancer, wherein the active agent comprises IMGN853, wherein the anti-FOLR1 antibody that does not competitively inhibit the binding of the active agent to FOLR1 comprises the amino acid sequences (a) SEQ ID NOs: 1, 2, and 3 and SEQ ID NOs: 13, 14, and 15; (b) SEQ ID NOs: 4, 5, and 6 and SEQ ID NOs: 16, 17, and 18; (c) SEQ ID NOs: 7, 8, and 9 and SEQ ID NOs: 19, 20, and 21; or (d) SEQ ID NOs: 10, 11, and 12 and SEQ ID NOs: 22, 23, and 24; and wherein the FOLR1 protein is detected by cytometry.

In some embodiments of the methods, the cancer is ovarian cancer. In some embodiments, the ovarian cancer is platinum resistant or platinum refractory. In some embodiments, the cancer is NSCLC. In some embodiments, the cancer is endometrial cancer.

The invention also provides active agents wherein the FOLR-1 mediated disease is cancer, wherein the active agent comprises IMGN853, and wherein the shed FOLR1 protein level is measured using an ELISA assay using at least two anti-FOLR1 antibodies that do not competitively inhibit the binding of the active agent to FOLR1, wherein each of the at least two anti-FOLR1 comprise amino acid sequences selected from the group consisting of: (a) SEQ ID NOs: 1, 2, and 3 and SEQ ID NOs: 13, 14, and 15; (b) SEQ ID NOs: 4, 5, and 6 and SEQ ID NOs: 16, 17, and 18; (c) SEQ ID NOs: 7, 8, and 9 and SEQ ID NOs: 19, 20, and 21; and (d) SEQ ID NOs: 10, 11, and 12 and SEQ ID NOs: 22, 23, and 24.

The invention also provides active agents wherein the FOLR-1 mediated disease is cancer, wherein the active agent comprises IMGN853, and wherein the shed FOLR1 protein level is measured using an ELISA assay using at least two anti-FOLR1 antibodies that do not competitively inhibit the binding of the active agent to FOLR1, wherein each of the at least two anti-FOLR1 comprise amino acid sequences selected from the group consisting of: (a) SEQ ID NOs: 1, 2, and 3 and SEQ ID NOs: 13, 14, and 15; (b) SEQ ID NOs: 4, 5, and 6 and SEQ ID NOs: 16, 17, and 18; (c) SEQ ID NOs: 7, 8, and 9 and SEQ ID NOs: 19, 20, and 21; and (d) SEQ ID NOs: 10, 11, and 12 and SEQ ID NOs: 22, 23, and 24.

In some embodiments of the active agents, the cancer is ovarian cancer. In some embodiments, the ovarian cancer is platinum resistant or platinum refractory. In some embodiments, the cancer is NSCLC. In some embodiments, the cancer is endometrial cancer.

The invention also provides a method of treating cancer comprising administering an active agent comprising an antibody or antigen-binding fragment thereof that modulates FOLR1 activity to a patient with elevated shed FOLR1 protein levels relative to a reference FOLR1 protein level, wherein the patient's FOLR1 protein levels were measured using an antibody, antigen-binding fragment, or polypeptide provided herein.

The invention also provides a method of treating cancer comprising administering an active agent comprising an antibody or antigen-binding fragment thereof that modulates FOLR1 activity to a patient with elevated FOLR1 protein levels on circulating tumor cells relative to a reference FOLR1 protein level, wherein the patient's FOLR1 protein levels were measured using an antibody, antigen-binding fragment, or polypeptide provided herein. In some embodiments, the active agent comprises IMGN853. In some embodiments, the cancer is ovarian cancer. In some embodiments, the ovarian cancer is platinum resistant or platinum refractory. In some embodiments, the cancer is NSCLC. In some embodiments, the cancer is endometrial cancer.

The invention also provides the use of an antibody, antigen-binding fragment thereof, or polypeptide of provided herein for the measurement of FOLR1 protein level in a sample in vitro.

BRIEF DESCRIPTIONS OF THE DRAWINGS

FIG. 1. Schematic representation of FOLR1 shed antigen assay.

Figure 2:
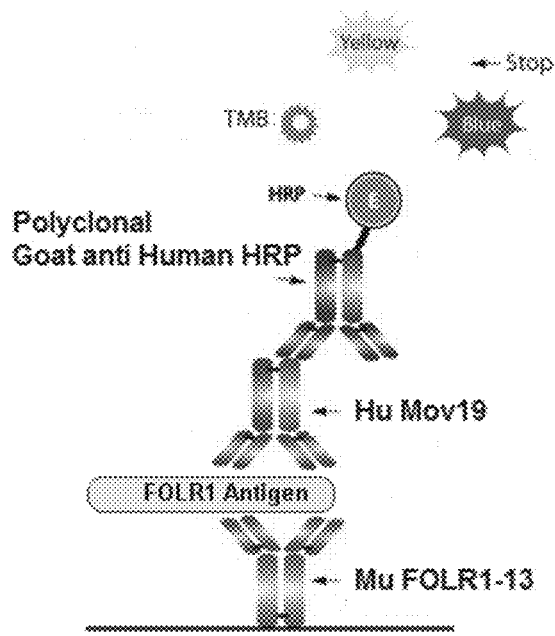
Figure 2:
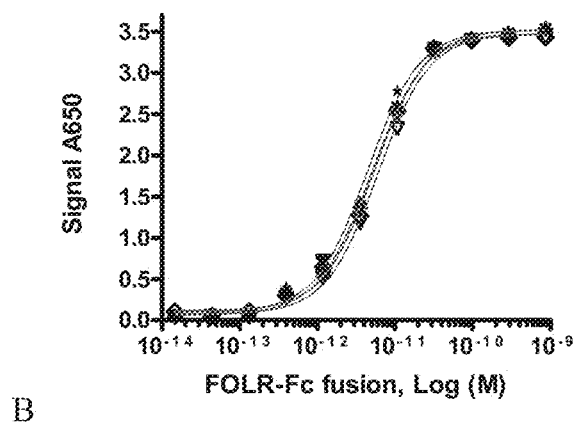

FIG. 2. (A) Schematic representation of Mov19 competition ELISA assay. (B) Determination of binding affinity of muFR1-13 by sandwich ELISA using Mov19.

Figure 3:
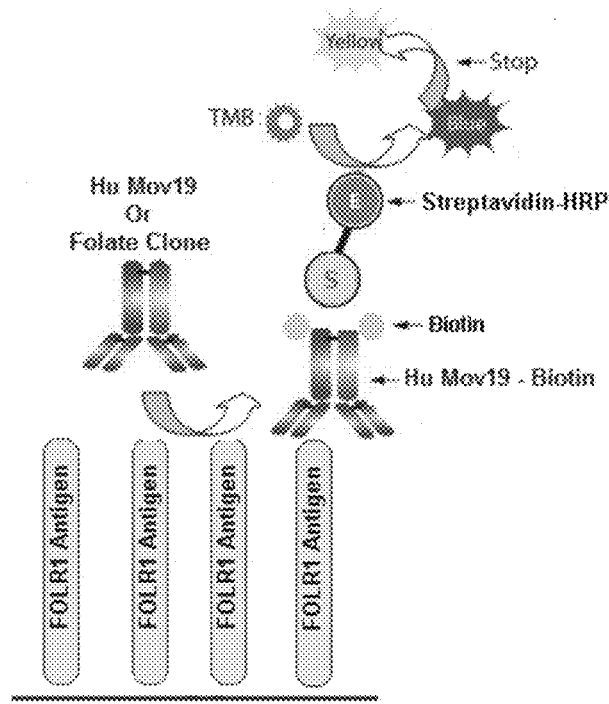
Figure 3:
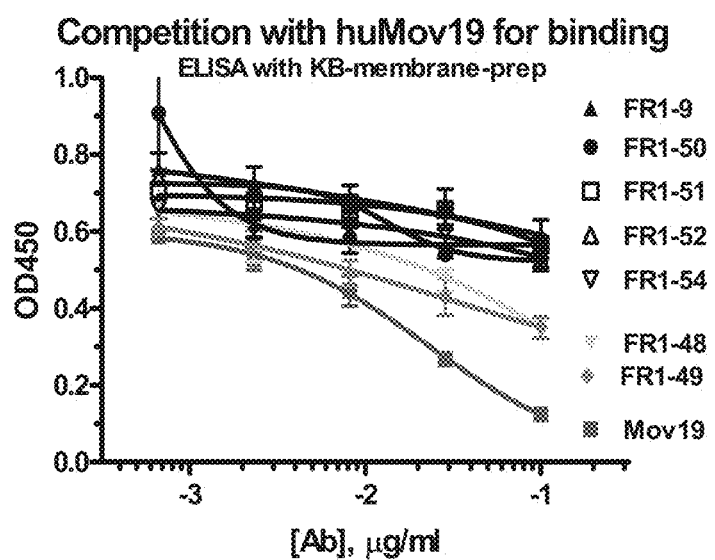

FIG. 3. (A) Schematic representation of direct binding competition ELISA to determine non-competing FOLR1 binding epitopes. (B) Log transformed graph of competition ELISA results to screen for binding interference of anti-FOLR1 antibodies with Mov19.

Figure 4:
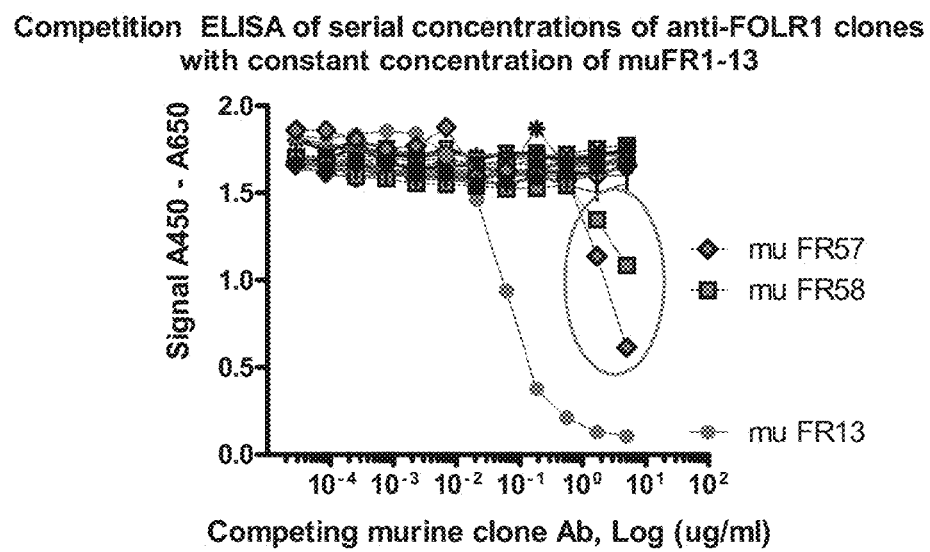

FIG. 4. Log transformed graph of competition ELISA results to screen for binding interference of anti-FOLR1 antibodies with muFR1-13.

Figure 5:
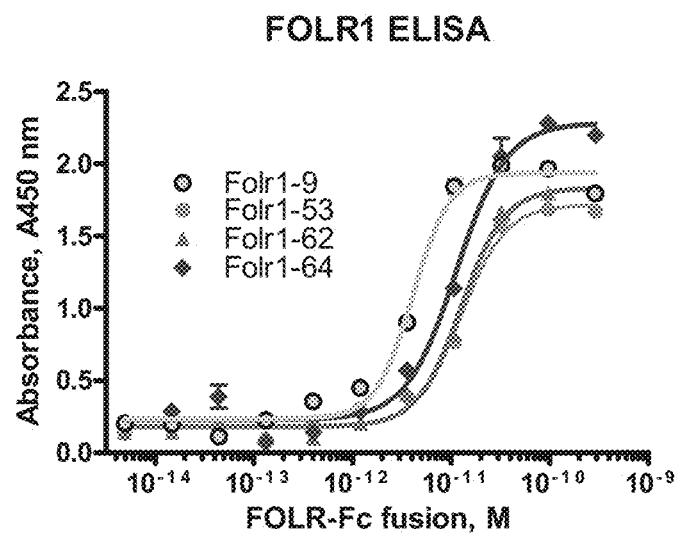

FIG. 5. Binding affinity of anti-FOLR1 antibodies by sandwich ELISA.

Figure 6:
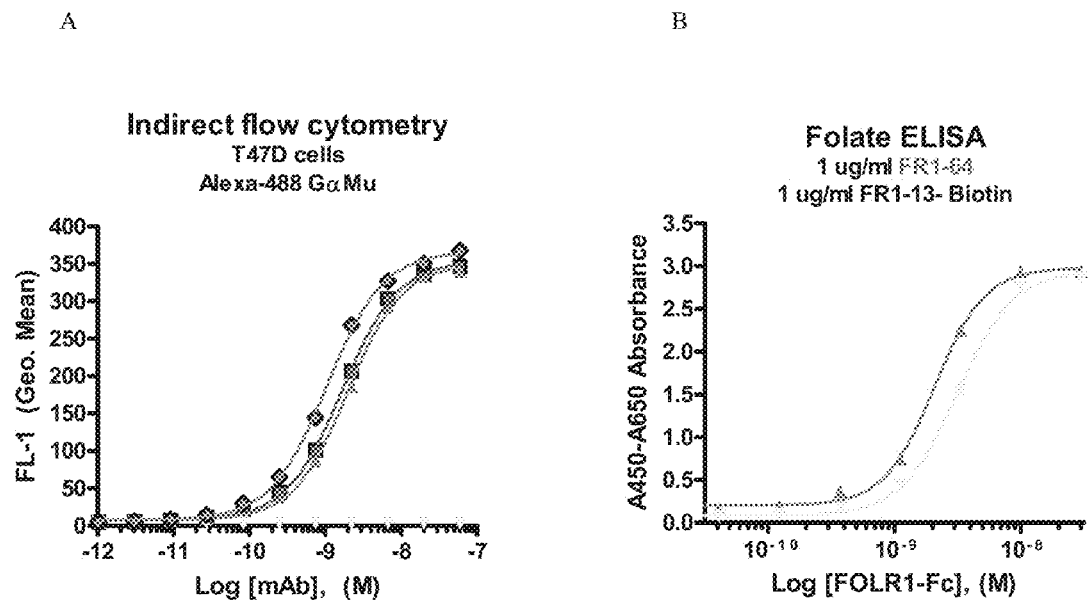

FIG. 6. Binding affinity of FR1-13 by both (A) flow cytometry and (B) sandwich ELISA.

Figure 7:
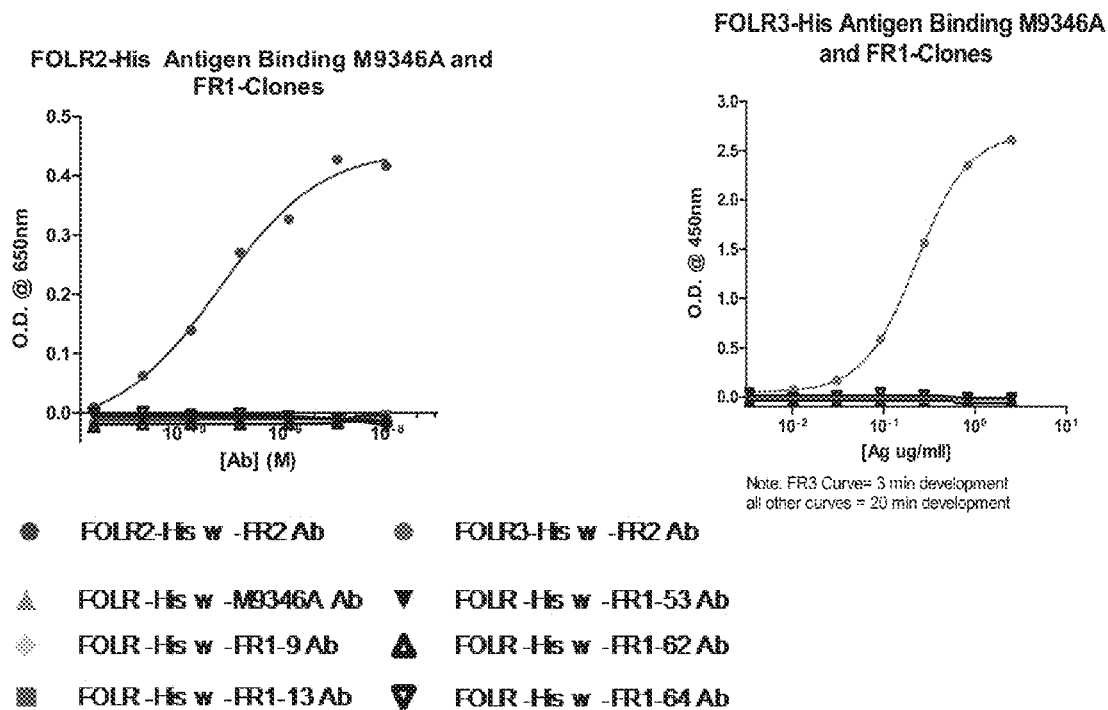

FIG. 7. Log transformed graph of results for Antibody binding to FOLR2 and FOLR3 by sandwich ELISA.

Figure 8:
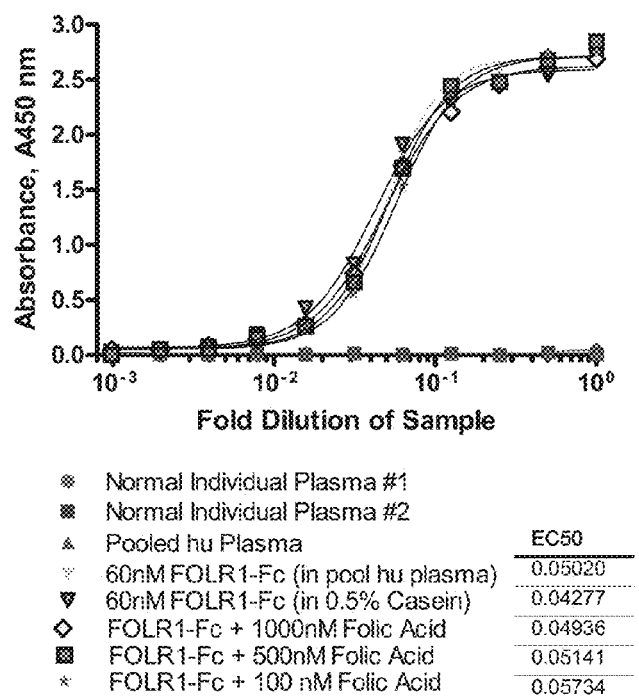

FIG. 8. Effect of pre-bound folic acid to FOLR1 on the detection of shed FOLR1 antigen using FR1-9 and FR1-13.

Figure 9:
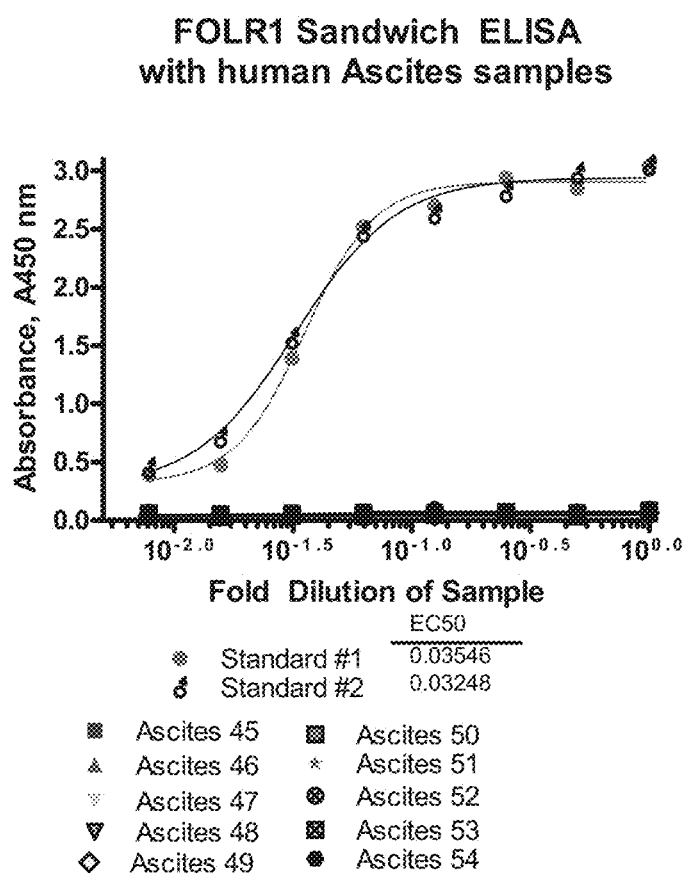

FIG. 9. Analysis of human ascites samples for the presence of FOLR1 and the presence of interfering assay proteins.

Figure 10:
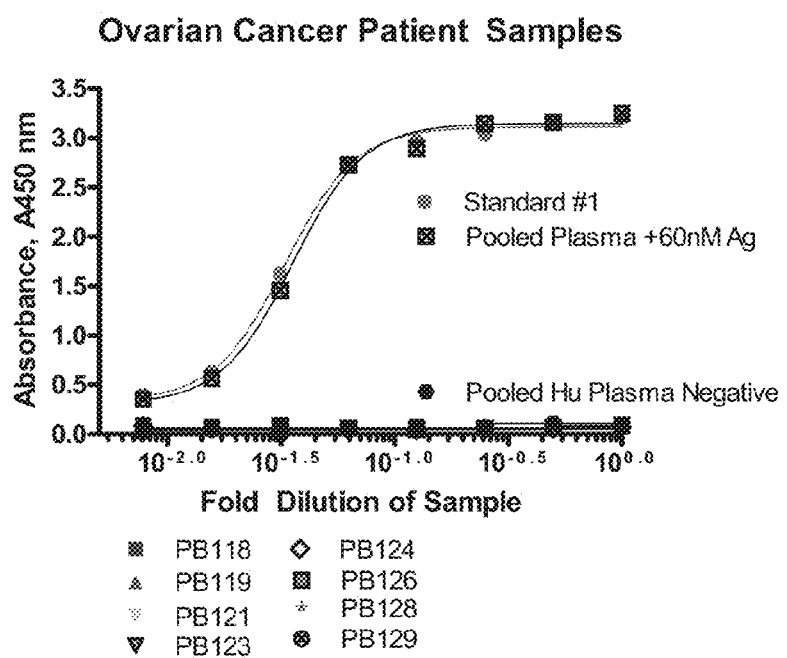

FIG. 10. Analysis of normal human pooled plasma samples for the presence of FOLR1 and the presence of interfering assay proteins.

Figure 11:
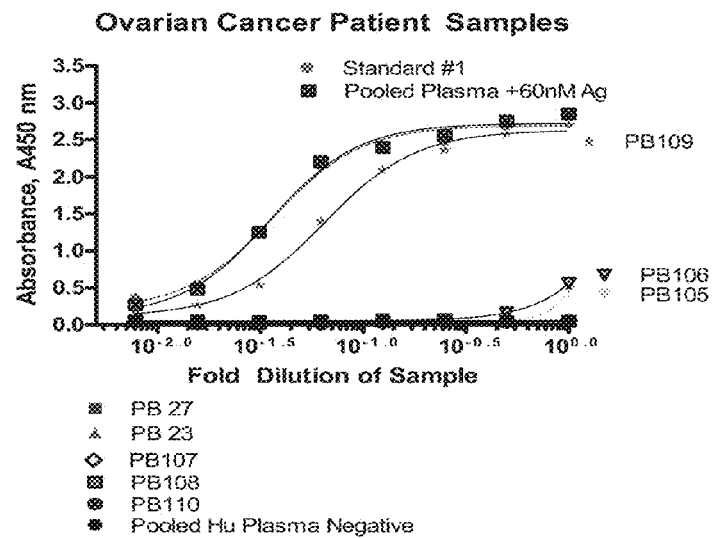

FIG. 11. Determination of FOLR1 concentration in human ovarian patient plasma samples using FOLR1 sandwich ELISA.

Figure 12:
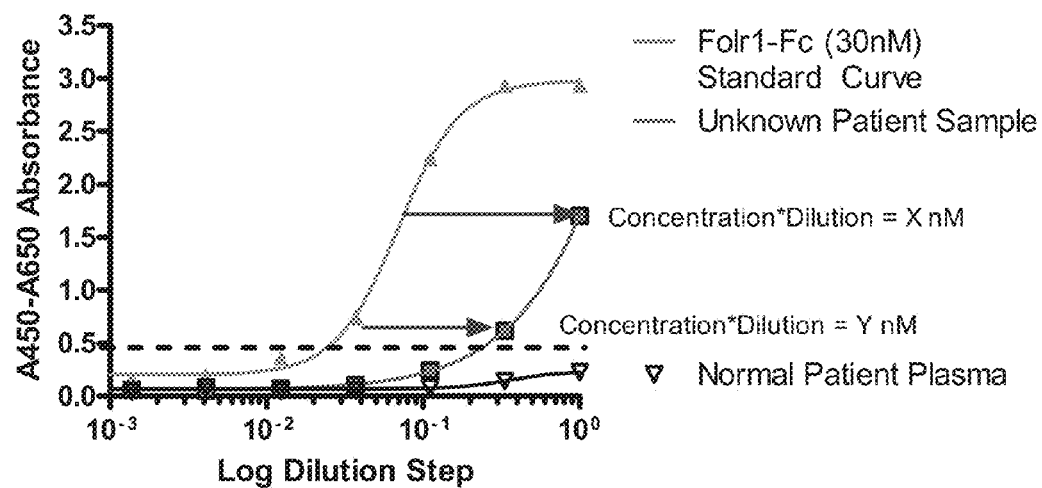

FIG. 12. Schematic representation for interpolating the amount of FOLR1 in a patient sample based on a 4PL sigmoidal dose response curve fit of serially-diluted purified FOLR1-Fc fusion protein standard.

Figure 13:
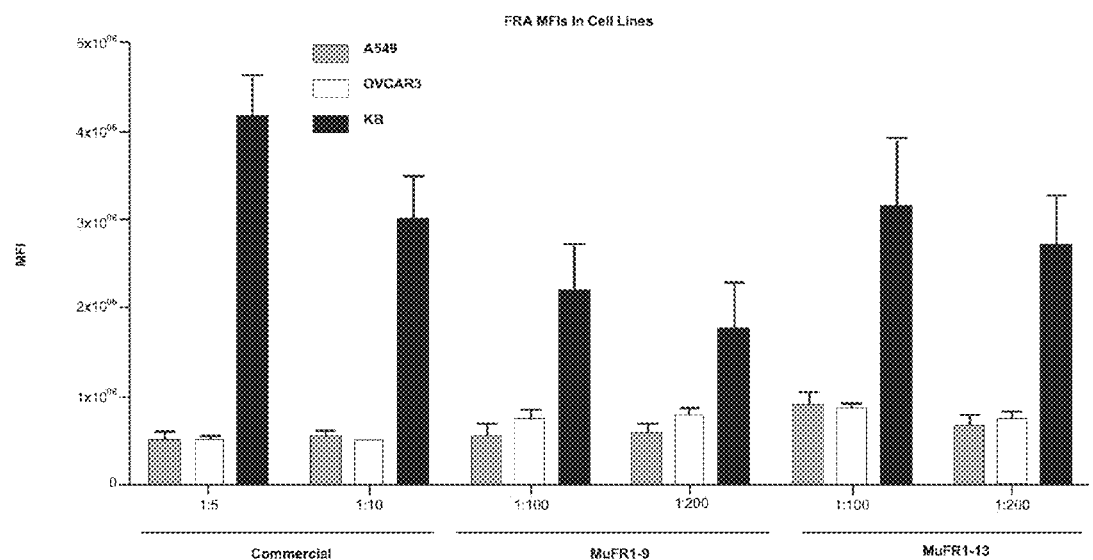

FIG. 13. Titration of anti-FOLR1 antibodies using cell lines with a range of FOLR1 expression levels. For each cell line and dilution, triplicate staining was performed. Mean Fluorescence Intensity (MFI) was measured for FRA expression and averaged and are shown in the table (error represents the SEM).

Figure 14:
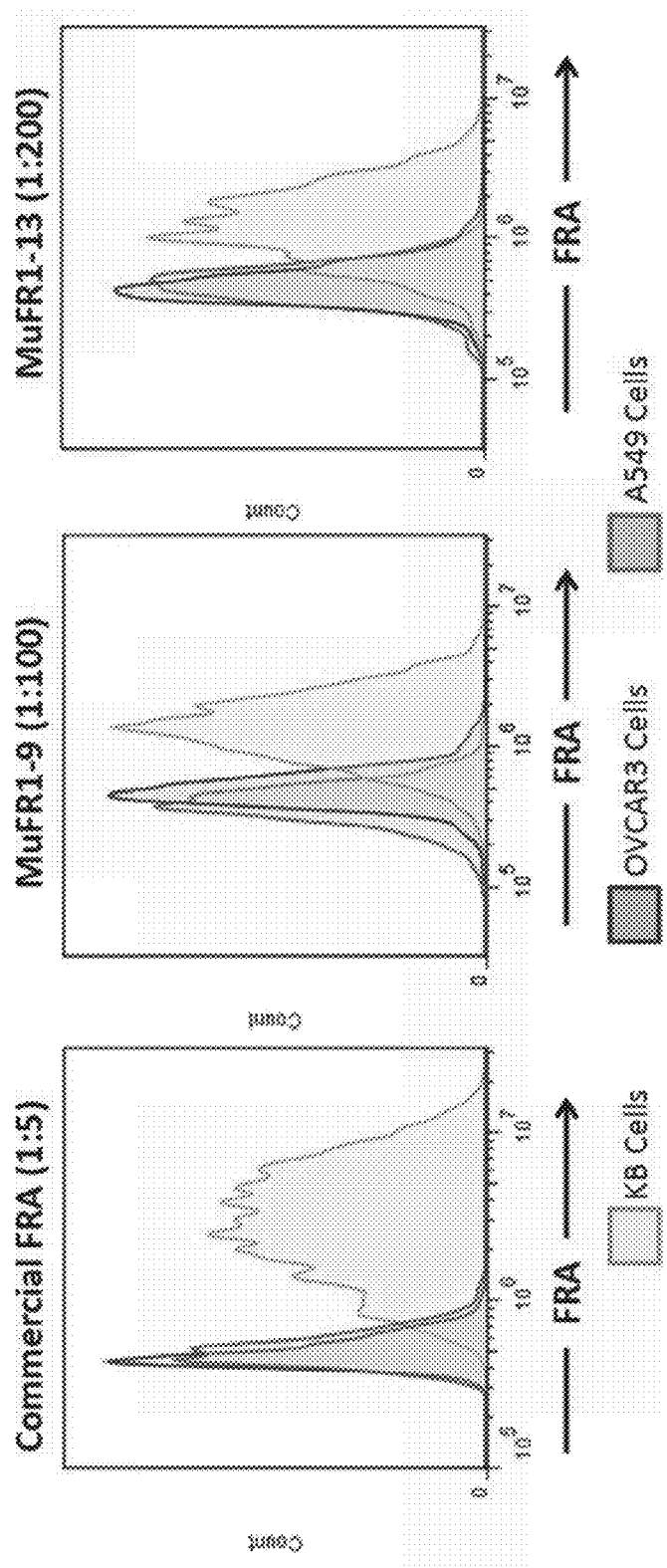

FIG. 14. Histograms showing FOLR1 expression in cell lines using optimal dilutions of anti-FOLR1 antibodies.

Figure 15:
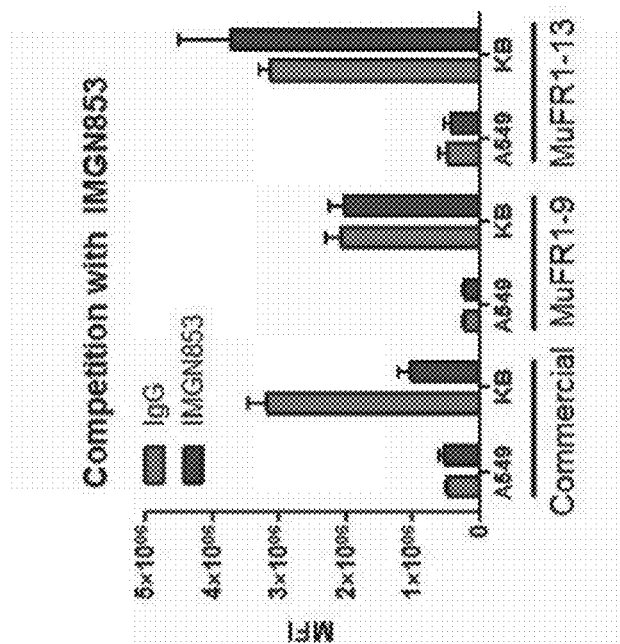

FIG. 15. Graph showing competition between anti-FOLR1 antibodies and IMGN853.

DETAILED DESCRIPTION OF THE INVENTION

The present invention provides a novel method of detecting shed human folate receptor 1 (FOLR1) or FOLR1 on circulating tumor cells in a patient sample. The FOLR1 can be detected using antibodies that do not competitively inhibit the binding of an anti-FOLR1 active agent (e.g., an active agent comprising the antibody huMov19) to FOLR1. Antibodies that do not competitively inhibit the binding of an anti-FOLR1 active agent are especially useful in detecting FOLR1 (e.g., shed FOLR1 or FOLR1 on circulating tumor cells) in samples from patients who have been treated with the anti-FOLR1 active agent. Shed FOLR1 or FOLR1 on circulating tumor cells can be used to monitor or determine therapeutic efficacy, or the likelihood of response to the treatment of cancers characterized by the overexpression of FOLR1. Novel FOLR1-binding polypeptides, such as antibodies, that are useful in the shed FOLR1 detection methods as well as additional FOLR1 detection methods (e.g., 1HC for membrane bound and cell associated FOLR1 and CTC assays) are also disclosed. Related polypeptides and polynucleotides, compositions comprising the FOLR1-binding agents, and methods of making the FOLR1-binding agents are also provided. In addition, methods provided herein can be used for patient stratification.

I. Definitions

To facilitate an understanding of the present invention, a number of terms and phrases are defined below.

The terms "human folate receptor 1," "FOLR1" or "folate receptor alpha (FR-α)," as used herein, refer to any native human FOLR1, unless otherwise indicated. Thus, all of these terms can refer to either a protein or nucleic acid sequence as indicated herein. The term "FOLR1" encompasses "full-length," unprocessed FOLR1 as well as any form of FOLR1 that results from processing within the cell. The term also encompasses naturally occurring variants of FOLR1, e.g., splice variants (except those variants that encompass FOLR2, FOLR3, or FOLR4), allelic variants and isoforms. The FOLR1 polypeptides described herein can be isolated from a variety of sources, such as from human tissue types or from another source, or prepared by recombinant or synthetic methods. Examples of FOLR1 sequences include, but are not limited to NCBI reference numbers P15328, NP_001092242.1, AAX29268.1, AAX37119.1, NP_057937.1, and NP_057936.1. The human FOLR1 sequence is a follows:

(SEQ ID NO: 49)
MAQRMTTQLLLLLVWVAVVGEAQTRIAWARTELLNVCMNAKHHKEKPGPE

DKLHEQCRPWRKNACCSTNTSQEAHKDVSYLYRFNWNHCGEMAPACKRHF

IQDTCLYECSPNLGPWIQQVDQSWRKERVLNVPLCKEDCEQWWEDCRTSY

TCKSNWHKGWNWTSGFNKCAVGAACQPFHFYFPTPTVLCNEIWTHSYKVS

NYSRGSGRCIQMWFDPAQGNPNEEVARFYAAAMSGAGPWAAWPFLLSLAL

MLLWLLS.

The terms "shed antigen" and "shed FOLR1" are used interchangeably herein. These terms refer to a FOLR1 protein that is soluble and that is not cell associated. In some embodiments it includes the extracellular domain (ECD) and the glycosylphosphatidyl inositol (GPI) linker. In one embodiment, the shed FOLR1 includes only the ECD. FOLR1 includes a signal peptide (amino acids 1-24) the FOLR1 protein chain (amino acids 25-233 or 234) and a propeptide which can be cleaved (amino acids 235 to 257). Shed FOLR can include amino acids 1 to 257, 1 to 233, 1 to 234, 25 to 233, 25 to 234 or any other fragments thereof. In some embodiments the signal sequence is cleaved. In other embodiments the ECD and the GPI portion can be embedded in a membrane (e.g., a soluble lipid raft). In one embodiment, the shed FOLR1 can include amino acids 1-233 or a fragment thereof.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

In some embodiments, an antibody is a non-naturally occurring antibody. In some embodiments, and antibody is purified from natural components. In some embodiments, an antibody is recombinant produced. In some embodiments, an antibody is produced by a hybridoma.

A "blocking" antibody or an "antagonist" antibody is one which inhibits or reduces biological activity of the antigen it binds, such as FOLR1. In a certain embodiment, blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

The term "anti-FOLR1 antibody" or "an antibody that binds to FOLR1" refers to an antibody that is capable of binding FOLR1 with sufficient affinity such that the antibody is useful as a diagnostic and/or therapeutic agent in targeting FOLR1. The extent of binding of an anti-FOLR1 antibody to an unrelated, non-FOLR1 protein is less than about 10% of the binding of the antibody to FOLR1 as measured, e.g., by a radioimmunoassay (RIA). In certain embodiments, an antibody that binds to FOLR1 has a dissociation constant (Kd) of ≤1 µM, ≤100 nM, ≤10 nM, ≤1 nM, or ≤0.1 nM. In one embodiment, the anti-FOLR1 antibody does not bind FOLR2, FOLR3, FOLR4, or folic acid.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments. The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, Nature, 256:495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, hamster) that have the desired specificity, affinity, and capability (Jones et al., 1986, *Nature,* 321:522-525; Riechmann et al., 1988, *Nature,* 332:323-327; Verhoeyen et al., 1988, *Science,* 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539 or U.S. Pat. No. 5,639,641. "Resurfacing" antibodies generally involves identification of the variable region framework surface residues in both the light and heavy chains and replacing them with human equivalents. Methods of resurfacing antibodies have been provided, for example in Roguska et al., Proc. Natl. Acad. Sci., USA, 91(3):969-973 (1994) and Roguska et al., Protein Eng. 9(10):895-904 (1996), which are incorporated in their entirety herein by reference.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) *J. Molec. Biol.* 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
| --- | --- | --- | --- |
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | (Kabat Numbering) | | |
| H1 | H31-H35 | H26-H35 | H26-H32 |
| | (Chothia Numbering) | | |
| H2 | H50-H65 | H50-H58 | H52-H56 |
| H3 | H95-H102 | H95-H102 | H95-H102 |

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described herein.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better," the antibody's affinity for the antigen is <0.6 nM, i.e., 0.59 nM, 0.58 nM, 0.57 nM etc. or any value less than 0.6 nM. In one embodiment, the antibody's affinity as determined by a Kd will be between about $10^{-3}$ to about $10^{-12}$ M, between about $10^{-6}$ to about $10^{-11}$ M, between about $10^{-6}$ to about $10^{-10}$ M, between about $10^{-6}$ to about $10^{-9}$ M, between about $10^{-6}$ to about $10^{-8}$ M, or between about $10^{-6}$ to about $10^{-7}$ M.

The phrase "substantially similar," or "substantially the same," as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristics measured by said values (e.g., Kd values). The difference between said two values is less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The term "increased expression" of FOLR1 refers to a sample which contains elevated levels of FOLR1 expression as compared to a reference sample, a reference FOLR1 level, or a previous FOLR1 level detected from the same subject. Thus, for example, "increased FOLR1 protein levels" in a patient sample can have FOLR1 protein levels that are higher than the FOLR1 protein levels in a non-cancerous reference sample. "Increased FOLR1 protein levels" in a patient sample can also, for example, have FOLR1 protein levels that are equal to the FOLR1 protein levels in a cancerous sample. In some embodiments, "increased FOLR1 protein levels" are detected wherein a patient's FOLR1 protein level is at least about 5%, at least about 10%, at least about 15%, at least about 20%, or at least about 25%, at least about 30%, or at least about 50% more than, for example, a previous FOLR1 level detected from the same subject. In circulating tumor cell assays, "increased FOLR1 protein levels" can refer to samples in which FOLR1 is detected on a greater percentage of cells or samples in which FOLR1 is detected in higher levels on the cells. Thus, in some embodiments, "increased FOLR1 protein levels" are detected in CTC assays where at least about 5%, at least about 10%, at least about 15%, at least about 20%, or at least about 25%, at least about 30%, or at least about 50% more cells show FOLR1 expression. In addition, in some embodiments, "increased FOLR1 protein levels" are detected in CTC assays where at least about 5%, at least about 10%, at least about 15%, at least about 20%, or at least about 25%, at least about 30%, or at least about 50% more FOLR1 is detected on cells.

A "reference sample" can be used to correlate and compare the results obtained in the methods of the invention from a test sample. Reference samples can be cells (e.g., cell lines, cell pellets), bodily fluids, or tissue. The FOLR1 levels in the "reference sample" may be an absolute or relative amount, a range of amount, a minimum and/or maximum amount, a mean amount, and/or a median amount of FOLR1. A "reference sample" can also serve as a baseline of FOLR1 expression to which the test sample is compared. The "reference sample" can include a prior sample or baseline sample from the same patient, a normal reference, or a reference from a relevant patient population. Generally, FOLR1 levels are expressed as values in a standard curve. A standard curve is a quantitative method of plotting assay data to determine the concentration of FOLR1 in a sample. In one embodiment, reference sample is an antigen standard comprising purified FOLR1 or FOLR1-Fc. The diagnostic methods of the invention involve a comparison between expression levels of FOLR1 in a test sample and a "reference value" or "reference level." In some embodiments, the reference value is the expression level of the FOLR1 in a reference sample. A reference value may be a predetermined value and may also be determined from reference samples (e.g., control biological samples) tested in parallel with the test samples. A reference value can be a single cut-off value, such as a median or mean or a range of values, such as a confidence interval. Reference values can be established for various subgroups of individuals, such as individuals predisposed to cancer, individuals having early or late stage cancer, male and/or female individuals, or individuals undergoing cancer therapy.

Examples of normal reference samples or values and positive reference samples or values are described herein.

The term "primary antibody" herein refers to an antibody that binds specifically to the target protein antigen in a sample. A primary antibody is generally the first antibody used in an ELISA assay. In one embodiment, the primary antibody is the only antibody used in an IHC procedure. The term "secondary antibody" herein refers to an antibody that binds specifically to a primary antibody, thereby forming a bridge between the primary antibody and a subsequent reagent, if any. The secondary antibody is generally the second antibody used in an immunohistochemical procedure.

As used herein, "immunohistochemistry" refers to histochemical and immunologic methods used to analyze, for example, cells or tissues. Thus, the terms "immunohistochemistry," "immunocytochemistry," and "immunochemistry" are used interchangeably.

A "sample" or "biological sample" of the present invention is of biological origin, in specific embodiments, such as from eukaryotic organisms. In preferred embodiments, the sample is a human sample, but animal samples may also be used in the practice of the invention. Non-limiting sources of a sample for use in the present invention include solid tissue, biopsy aspirates, ascites, fluidic extracts, blood, plasma, serum, spinal fluid, lymph fluid, the external sections of the skin, respiratory, intestinal, and genitourinary tracts, tears, saliva, milk, tumors, organs, cell cultures and/or cell culture constituents, for example. The present invention is particularly useful for cancer samples which generally comprise bodily fluids such as ascites, where the amount of available material is small. The method can be used to examine an aspect of expression of FOLR1 or a state of a sample, including, but not limited to, comparing different types of cells or tissues, comparing different developmental stages, and detecting or determining the presence and/or type of disease or abnormality.

As used herein, the term "capture reagent" refers to a reagent capable of binding and capturing a target molecule in a sample such that under suitable condition, the capture reagent-target molecule complex can be separated from the rest of the sample. In one embodiment, the capture reagent is immobilized. In one embodiment, the capture reagent in a sandwich immunoassay is an antibody or a mixture of different antibodies against a target antigen.

As used herein, the term "detectable antibody" refers to an antibody that is capable of being detected either directly through a label amplified by a detection means, or indirectly through, e.g., another antibody that is labeled. For direct labeling, the antibody is typically conjugated to a moiety that is detectable by some means. In one embodiment, the detectable antibody is a biotinylated antibody.

The word "label" when used herein refers to a detectable compound or composition which is conjugated directly or indirectly to the antibody so as to generate a "labeled" antibody. The label can be detectable by itself (e.g., radioisotope labels or fluorescent labels) or, in the case of an enzymatic label, can catalyze chemical alteration of a substrate compound or composition which is detectable.

As used herein, the term "detection means" refers to a moiety or technique used to detect the presence of the detectable antibody in the ELISA herein and includes detection agents that amplify the immobilized label such as label captured onto a microtiter plate. In one embodiment, the detection means is a fluorimetric detection agent such as avidin or streptavidin.

Commonly a "sandwich ELISA" employs the following steps: (1) microtiter plate is coated with a capture antibody; (2) sample is added, and any antigen present binds to capture antibody; (3) detecting antibody is added and binds to antigen; (4) enzyme-linked secondary antibody is added and binds to detecting antibody; and (5) substrate is added and is converted by enzyme to detectable form.

By "correlate" or "correlating" is meant comparing, in any way, the performance and/or results of a first analysis with the performance and/or results of a second analysis. For example, one may use the results of a first analysis in carrying out the second analysis and/or one may use the results of a first analysis to determine whether a second analysis should be performed and/or one may compare the results of a first analysis with the results of a second analysis. In one embodiment, increased expression of FOLR1 correlates with increased likelihood of effectiveness of a FOLR1-targeting anti-cancer therapy.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include cancers of endothelial, mesenchymal, or epithelial origin, such as lung cancer (e.g., squamous cell cancer, small-cell lung cancer, non-small cell lung cancer, adenocarcinoma of the lung, mesothelioma, and squamous carcinoma of the lung), cancer of the peritoneum (e.g., primary peritoneal), hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial (e.g., endometrial adenocarcinoma) or uterine carcinoma, salivary gland carcinoma, kidney cancer, liver cancer, prostate cancer, vulval cancer, thyroid cancer, hepatic carcinoma, brain cancer (e.g. glioblastoma, tumors of the choroid plexus) and various types of head and neck cancers, and also tumors of blood vessels and fallopian tubes. Cancers also encompass cancers which contain cells having elevated FOLR1 expression levels. Such FOLR1-elevated cancers include, but are not limited to, ovarian, non-small cell lung cancer, uterine, endometrial, pancreatic, renal, lung, and breast cancer.

"Tumor" and "neoplasm" refer to any mass of tissue that result from excessive cell growth or proliferation, either benign (noncancerous) or malignant (cancerous) including pre-cancerous lesions.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "pharmaceutical formulation" refers to a preparation which is in such form as to permit the biological activity of the active ingredient to be effective, and which contains no additional components which are unacceptably toxic to a subject to which the formulation would be administered. Such formulation can be sterile.

An "effective amount" of an antibody as disclosed herein is an amount sufficient to carry out a specifically stated purpose.

An "effective amount" can be determined empirically and in a routine manner, in relation to the stated purpose.

The term "therapeutically effective amount" or "fixed dose" refers to an amount of an antibody or other drug effective to "treat" a disease or disorder in a subject or mammal. In the case of cancer, the therapeutically effective amount of the drug can reduce the number of cancer cells; reduce the tumor size; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; relieve to some extent one or more of the symptoms associated with the cancer; and/or result in a favorable response such as increased progression-free survival (PFS), disease-free survival (DFS), or overall survival (OS), complete response (CR), partial response (PR), or, in some cases, stable disease (SD), a decrease in progressive disease (PD), a reduced time to progression (TTP), a decrease in CA125 in the case of ovarian cancer, or any combination thereof. See the definition herein of "treating." To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

PFS, DFS, and OS can be measured by standards set by the National Cancer Institute and the U.S. Food and Drug Administration for the approval of new drugs. See Johnson et al, (2003) J. Clin. Oncol. 21(7):1404-1411.

"Progression free survival" (PFS) refers to the time from enrollment to disease progression or death. PFS is generally measured using the Kaplan-Meier method and Response Evaluation Criteria in Solid Tumors (RECIST) 1.1 standards. Generally, progression free survival refers to the situation wherein a patient remains alive, without the cancer getting worse.

"Time to Tumor Progression" (TTP) is defined as the time from enrollment to disease progression. TTP is generally measured using the RECIST 1.1 criteria.

A "complete response" or "complete remission" or "CR" indicates the disappearance of all signs of tumor or cancer in response to treatment. This does not always mean the cancer has been cured.

A "partial response" or "PR" refers to a decrease in the size or volume of one or more tumors or lesions, or in the extent of cancer in the body, in response to treatment.

"Stable disease" refers to disease without progression or relapse. In stable disease there is neither sufficient tumor shrinkage to qualify for partial response nor sufficient tumor increase to qualify as progressive disease.

"Progressive disease" refers to the appearance of one more new lesions or tumors and/or the unequivocal progression of existing non-target lesions. Progressive disease can also refer to a tumor growth of more than 20 percent since treatment began, either due to an increases in mass or in spread of the tumor.

"Disease free survival" (DFS) refers to the length of time during and after treatment that the patient remains free of disease.

"Overall Survival" (OS) refers to the time from patient enrollment to death or censored at the date last known alive. OS includes a prolongation in life expectancy as compared to naive or untreated individuals or patients. Overall survival refers to the situation wherein a patient remains alive for a defined period of time, such as one year, five years, etc., e.g., from the time of diagnosis or treatment.

A "decrease in CA125 levels" can be assessed according to the Gynecologic Cancer Intergroup (GCIG) guidelines. For example, CA125 levels can be measured prior to treatment to establish a baseline CA125 level. CA125 levels can be measured one or more times during or after treatment, and a reduction in the CA125 levels over time as compared to the baseline level is considered a decrease in CA125 levels.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer according to the methods of the present invention if the patient shows one or more of the following: reduction in cachexia, increase in survival time, elongation in time to tumor progression, reduction in tumor mass, reduction in tumor burden and/or a prolongation in time to tumor metastasis, time to tumor recurrence, tumor response, complete response, partial response, stable disease, progressive disease, progression free survival (PFS), overall survival (OS), each as measured by standards set by the National Cancer Institute and the U.S. Food and Drug Administration for the approval of new drugs. See Johnson et al, (2003) J. Clin. Oncol. 21(7):1404-1411.

"Polynucleotide" or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after polymerization, such as by conjugation with a labeling component. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars can be replaced, for example, by phosphonate groups, phosphate groups, protected by standard protecting groups, or activated to prepare additional linkages to additional nucleotides, or can be conjugated to solid supports. The 5' and 3' terminal OH can be phosphorylated or substituted with amines or organic capping group moieties of from 1 to 20 carbon atoms. Other hydroxyls can also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages can be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector" means a construct, which is capable of delivering, and expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains. In some embodiments, a polypeptide, peptide, or protein is non-naturally occurring. In some embodiments, a polypeptide, peptide, or protein is purified from other naturally occurring components. In some embodiments, the polypeptide, peptide, or protein is recombinantly produced.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, 1990, *Proc. Natl. Acad. Sci.*, 87:2264-2268, as modified in Karlin et al., 1993, *Proc. Natl. Acad. Sci.*, 90:5873-5877, and incorporated into the NBLAST and XBLAST programs (Altschul et al., 1991, *Nucleic Acids Res.*, 25:3389-3402). In certain embodiments, Gapped BLAST can be used as described in Altschul et al., 1997, *Nucleic Acids Res.* 25:3389-3402. BLAST-2, WU-BLAST-2 (Altschul et al., 1996, *Methods in Enzymology*, 266:460-480), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48): 444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In certain embodiments, identity exists over a region of the sequences that is at least about 10, about 20, about 40-60 residues in length or any integral value therebetween, or over a longer region than 60-80 residues, at least about 90-100 residues, or the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the invention do not abrogate the binding of the polypeptide or antibody containing the amino acid sequence, to the antigen(s), i.e., the FOLR1 to which the polypeptide or antibody binds. Methods of identifying nucleotide and amino acid conservative substitutions which do not eliminate antigen-binding are well-known in the art (see, e.g., Brummell et al., *Biochem.* 32: 1180-1 187 (1993); Kobayashi et al. *Protein Eng.* 12(10):879-884 (1999); and Burks et al. *Proc. Natl. Acad. Sci. USA* 94:.412-417 (1997)).

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Shed Antigen Assay

The antibody maytansinoid conjugate (AMC), IMGN853, comprises the FOLR1-binding monoclonal antibody, huMov19 (M9346A), conjugated to the maytansinoid, DM4 (N(2')-deacetyl-N2'-(4-mercapto-4-methyl-1-oxopentyl)-maytansine), attached via the cleavable sulfo-SPDB (N-succinimidyl 4-(2-pyridyldithio)-2-sulfobutanoate) linker. IMGN853 and huMov19 are described in co-pending US Appl. Pub. No. 2012/0009181, which is herein incorporated by reference in its entirety. The FOLR1 antigen contains a single epitope recognized by Mov19. In one embodiment, the huMov19 antibody comprises the heavy and light chains with the following sequences:

SEQ ID NO: 46: huMov19 vHC
QVQLVQSGAEVVKPGASVKISCKASGYTFTGYFMNWVKQSPGQSLEWIGR

IHPYDGDTFYNQKFQGKATLTVDKSSNTAHMELLSLTSEDFAVYYCTRYD

GSRAMDYWGQGTTVTVSS

SEQ ID NO: 47 - huMov19 vLCv1.00
DIVLTQSPLSLAVSLGQPAIISCKASQSVSFAGTSLMHWYHQKPGQQPRL

LIYRASNLEAGVPDRFSGSGSKTDFTLNISPVEAEDAATYYCQQSREYPY

TFGGGTKLEIKR

-continued
SEQ ID NO: 48 - huMov19 vLCv1.60
DIVLTQSPLSLAVSLGQPAIISCKASQSVSFAGTSLMHWYHQKPGQQPRL

LIYRASNLEAGVPDRFSGSGSKTDFTLTISPVEAEDAATYYCQQSREYPY

TFGGGTKLEIKR.

In some embodiments, an anti-FOLR1 active agent such as IMGN853 modulates FOLR1 activity, e.g. decreases the activity of the FOLR1 protein.

IMGN853 is currently in clinical development for various therapeutic indications which include FOLR1 positive ovarian cancer, non-small cell lung cancer, endometrioid cancer, renal cancer, and other epithelial malignancies. Ovarian cancers exhibit the greatest FOLR1 penetrance and are considered the major indications for treatment with IMGN853 (Antony AC. Ann Rev Nutr 16:501-21 (1996); Yuan Y et al. Hum Pathol 40(10):1453-1460 (2009)).

Measuring levels of circulating antigen in patient plasma samples (shed antigen) may help identify patient populations more likely to respond to AMC treatment. High levels of shed antigen have been reported to markedly affect the pharmacokinetics of therapeutic antibodies (Tolcher A. et al. 20th Symposium on Molecular Targets and Cancer Therapeutics; Oct. 21-24, 2008; Geneva, Switzerland: EORTC-NCI-AACR, p 163, #514; Baselga J, et al. J Clin Oncol 14:737-744 (1996)). It is likely that shed antigen levels from patient plasma samples will be variable depending on factors such as antigen target, disease indications, and disease course. Currently shed antigen levels in disease indications for IMGN853 have been insufficiently examined while correlation with solid tumor expression is limited. While elevation of FOLR1 has been reported in ovarian adenocarcinomas, data suggests that it is not elevated in other FOLR1+tumor indications, such as small cell lung carcinoma (Mantovani L T, et al. Eur J Cancer 30A(3):363-9 (1994); Basal E, et al. PLoS ONE 4(7): e6292 (2009)). The present method allows for detection of the FOLR1 receptor in the presence of high folic acid. Previous assays have used Mov19 in the design of the assay. Since IMGN853 contains Mov19 and in one embodiment is the targeted therapy of the invention, it is vital that the method detects FOLR1 in the presence or absence of Mov19 in embodiments where IMGN853 is administered prior to the detection of FOLR1. Previous assays that use Mov19 have competitive effects and will detect significantly less or no FOLR1 in patients receiving IMGN853 treatment.

In one embodiment, the present method for detecting FOLR1 in human sourced fluid samples uses a traditional sandwich ELISA format (FIG. 1). In one embodiment, the method uses a capture agent (i.e., antibody, other protein) to FOLR1 attached to a solid support. In one embodiment, the solid support is a microtiter plate. To this, the sample (ascites fluids, blood, serum, plasma, etc.) is added without dilution, and is detected by a different detection agent (a different antibody or protein), which does not interfere with the binding of the first capture agent. The detection agent is then detected through the use of a secondary detection agent (biotin/streptavidin, anti-human secondary mono or polyclonal antibody, etc.) which can bind more than one time to the first detection agent, thus amplifying the signal of detection. The secondary detection agent is then quantified by the use of some other means (e.g., TMB/peroxidase, scintillation counting, fluorescent probes, etc.). Additionally, the assay detects FOLR1 and is not negatively impacted by the presence of Mov19, IMGN853, other FOLR1 family members, or folic acid.

The assays of the present invention include assays both to select patients eligible to receive FOLR1-based therapy and assays to monitor patient response. Assays for response prediction are run before therapy selection, and levels of shed FOLR1 may impact therapy decisions. For monitoring patient response, the assay is run at the initiation of therapy to establish baseline (or predetermined) levels of FOLR1 in the sample. The same sample is then assayed and the levels of FOLR1 compared to the baseline or predetermined levels. As used herein, the term "predetermined level" refers generally to an assay cutoff value that is used to assess diagnostic results by comparing the assay results against the predetermined level, and where the predetermined level already has been linked or associated with various clinical parameters (e.g., monitoring whether a subject being treated with a drug has achieved an efficacious blood level of the drug, monitoring the response of a subject receiving treatment for cancer with an anti-cancer drug, monitoring the response of a tumor in a subject receiving treatment for said tumor, etc.). The predetermined level may be either an absolute value or a value normalized by subtracting the value obtained from a patient prior to the initiation of therapy. An example of a predetermined level that can be used is a baseline level obtained from one or more subjects that may optionally be suffering from one or more diseases or conditions. The comparison (or informational analysis) of the level of the assayed biomarker with the baseline or predetermined level can be done by an automated system, such as a software program or intelligence system that is part of, or compatible with, the equipment (e.g., computer platform) on which the assay is carried out. Alternatively, this comparison or informational analysis can be done by a physician. In one embodiment, where the levels remain the same or decrease, the therapy may be effective and can be continued. Where significant increase over baseline level (or predetermined level) occurs, the patient may not be responding. In another embodiment, an increase in shed FOLR1 levels may be indicative of increased cell death and increased release of the shed FOLR1. In this embodiment, an increase in shed FOLR1 is indicative of therapeutic efficacy. Accordingly, in some embodiments, shed FOLR1 is measured and cell death is measured. Assays for measuring cell death are known in the art and include, for example, detection of M30-antigen (caspase-cleaved cytokeratin), markers of DNA damage such as γ-H2AX, or morphological features of cells such as fragmented and/or condensed DAPI-stained nuclei.

The assays of the present invention can be performed by any protein assay methods. Protein assay methods useful in the invention are well known in the art and include immunoassay methods involving binding of a specific unlabeled or labeled antibody or protein to the expressed protein or fragment of FOLR1. Useful immunoassay methods include both solution phase assays conducted using any format known in the art, such as, but not limited to, Biacore, time resolved fluorescence energy transfer (TR-FRET), an ELISA format, (sandwich, forward and reverse competitive inhibition) or a fluorescence polarization format, and solid phase assays such as immunohistochemistry. The FOLR-1 binding agents provided below are particularly useful for these immunoassay methods.

III. FOLR1-Binding Agents

The present invention provides agents that specifically bind human FOLR1. These agents are referred to herein as "FOLR1-binding agents."

The FOLR1-binding agents include FOLR1-binding agents that comprise the heavy and light chain CDR sequences of muFR1-9, muFR1-13, muFR1-53, muFR1-62, and muFR1-64. The CDR sequences muFR1-9, muFR1-13, muFR1-53, and muFR1-62 are described in Tables 1 and 2 below.

TABLE 1

Variable heavy chain CDR amino acid sequences

| Antibody | VH-CDR1 | VH-CDR2 | VH-CDR3 |
|---|---|---|---|
| muFR1-9 | SFGMH (SEQ ID NO: 1) | YISSGSSTFYYADTVKG (SEQ ID NO: 2) | ELTGTFAY (SEQ ID NO: 3) |
| muFR1-13 | RYSVH (SEQ ID NO: 4) | MIWSGGNTDYNSVFKS (SEQ ID NO: 5) | FDGKVSWFAY (SEQ ID NO: 6) |
| muFR1-53 | DYDIS (SEQ ID NO: 7) | EIYPGSGRTYYNERFKG (SEQ ID NO: 8) | SYYYGTNSPFAY (SEQ ID NO: 9) |
| muFR1-62 | TYTMH (SEQ ID NO: 10) | YINPTSGYNNYNQKFKE (SEQ ID NO: 11) | GGAYGRRPVDY (SEQ ID NO: 12) |

TABLE 2

Variable light chain CDR amino acid sequences

| Antibody | VL-CDR1 | VL-CDR2 | VL-CDR3 |
|---|---|---|---|
| muFR1-9 | RASQSINNNLH (SEQ ID NO: 13) | YASQSIS (SEQ ID NO: 14) | QQSNSWPQVT (SEQ ID NO: 15) |
| muFR1-13 | KASQSVSNDVL (SEQ ID NO: 16) | YAYNRYS (SEQ ID NO: 17) | QQDHSSPFT (SEQ ID NO: 18) |
| muFR1-53 | RASQDISNYLH (SEQ ID NO: 19) | YTSRLQS (SEQ ID NO: 20) | QQGNSLPPT (SEQ ID NO: 21) |
| muFR1-62 | KASQNVGTNVA (SEQ ID NO: 22) | SASSRYS (SEQ ID NO: 23) | HQYNSYPYT (SEQ ID NO: 24) |

The FOLR1 binding molecules can be antibodies or antigen-binding fragments that specifically bind to FOLR1 that comprise the CDRs of muFR1-9, muFR1-13, muFR1-53, muFR1-62, or muFR1-64 with up to four (i.e., 0, 1, 2, 3, or 4) conservative amino acid substitutions per CDR.

Polypeptides can comprise one of the individual variable light chains or variable heavy chains described herein. Antibodies and polypeptides can also comprise both a variable light chain and a variable heavy chain. The variable light chain and variable heavy chain sequences of murine muFR1-9, muFR1-13, muFR1-53, and muFR1-62 antibodies are provided in Tables 3 and 4 below.

TABLE 3

Variable heavy chain amino acid sequences

| Antibody | VH Amino Acid Sequence (SEQ ID NO) |
|---|---|
| muFR1-9HCvar | QVQLVESGGGLVQPGGSRKLSCAASGFTFSSFGMHW VRQAPEKGLEWVAYISSGSSTFYYADTVKGRFTISR DNPKNTLFLQMTSLRSEDTAMYYCAKELTGTFAYWG QGTLVTVSA (SEQ ID NO: 25) |

TABLE 3-continued

Variable heavy chain amino acid sequences

| Antibody | VH Amino Acid Sequence (SEQ ID NO) |
|---|---|
| muFR1-13HCvar | QVQLKESGPDLVAPSQSLSITCTVSGFSLSRYSVHW IRQPPGKGLEWLGMIWSGGNTDYNSVFKSRLNITKD NSKSQVFLKMNSLQTDDTAIYYCATFDGKVSWFAYW GQGTLVTVSA (SEQ ID NO: 26) |
| muFR1-53HC | QVQLQQSGPELVRPGASVKMSCKASGYKFTDYDISW VGLQRTGQGLEWIEIYPGSGRTYYNERFKGKATLTA DKSSNTVYMQLSSLTSEDSAVYFCASSYYYGTNSPF AYWGQGTTLTVSS (SEQ ID NO: 27) |
| muFR1-62HC | QVQLQQSGAELARPGASVKMSCKASGYTFTTYTMHW VKQRPGQGLEWIAYINPTSGYNNYNQKFKEKATLTA DKSSSTAYMQLTSLTSEDSAVYYCASGGAYGRRPVD YWGQGTSVTVSS (SEQ ID NO: 28) |

TABLE 4

Variable light chain amino acid sequences

| Antibody | VL Amino Acid Sequence (SEQ ID NO) |
|---|---|
| muFR1-9LCvar | DIVLTQSPATLSVTPGDSVSLSCRASQSINNNLHW YQQKSHESPRLLIKYASQSISGIPSRFSGSGSGTD FTLSINSVETEDFGMYFCQQSNSWPQVTFGAGTKL ELKR (SEQ ID NO: 29) |
| muFR1-13LCvar | SIVMTQTPKFLLVSTGDRFTITCKASQSVSNDVLW YQQKPGQSPKLLIYYAYNRYSGVPDRFTGSGYGTD FTFTITTVQSEDLAVYFCQQDHSSPFTFGSGTKLE IKR (SEQ ID NO: 30) |
| muFR1-53LC | DIQMTQTTSSLSASLGDRVTISCRASQDISNYLHW YQRKPDGTVKLLVYYTSRLQSGVPSRFSGSGSGTD YSLTISNLEQEDIATYFCQQGNSLPPTFGSGTKLE IKR (SEQ ID NO: 31) |
| muFR1-62LC | DIVMTQSQKFMSISVGDRVSVTCKASQNVGTNVAW YQQKPGQSPKTLIYSASSRYSGVPDRFTGSGSGTD FTLTISNVQSEDLADYFCHQYNSYPYTFGGGTKLE IKR (SEQ ID NO: 32) |

Also provided are polypeptides that comprise: (a) a polypeptide having at least about 90% sequence identity to SEQ ID NOs:25-28; and/or (b) a polypeptide having at least about 90% sequence identity to SEQ ID NOs:29-32. In certain embodiments, the polypeptide comprises a polypeptide having at least about 95%, at least about 96%, at least about 97%, at least about 98%, or at least about 99% sequence identity to SEQ ID NOs:25-32. Thus, in certain embodiments, the polypeptide comprises (a) a polypeptide having at least about 95% sequence identity to SEQ ID NOs:25-28, and/or (b) a polypeptide having at least about 95% sequence identity to SEQ ID NOs:29-32. In certain embodiments, the polypeptide comprises (a) a polypeptide having the amino acid sequence of SEQ ID NOs:25-28; and/or (b) a polypeptide having the amino acid sequence of SEQ ID NOs:29-32. In certain embodiments, the polypeptide is an antibody and/or the polypeptide specifically binds FOLR1. In certain embodiments, the polypeptide is a murine, chimeric, or humanized antibody that specifically binds FOLR1. In certain embodiments, the polypeptide having a certain percentage of sequence identity to SEQ ID NOs:25-32 differs from SEQ ID NOs:25-32 by conservative amino acid substitutions only.

Polypeptides can comprise one of the individual light chains or heavy chains described herein. Antibodies and polypeptides can also comprise both a light chain and a heavy chain. The light chain and variable chain sequences of murine muFR1-9, muFR1-13, muFR1-53, and muFR1-62 antibodies are provided in Tables 5 and 6 below.

TABLE 5

Full-length heavy chain amino acid sequences

| Antibody | Full-Length Heavy Chain Amino Acid Sequence (SEQ ID NO) |
|---|---|
| muFR1-9HC | QVQLVESGGGLVQPGGSRKLSCAASGFTFSSFGMHWVRQ APEKGLEWVAYISSGSSTFYYADTVKGRFTISRDNPKNT LFLQMTSLRSEDTAMYYCAKELTGTFAYWGQGTLVTVSA AKTTPPSVYPLAPGSAAQTNSMVTLGCLVKGYFPEPVTV TWNSGSLSSGVHTFPAVLESDLYTLSSSVTVPSSMRPSE TVTCNVAHPASSTKVDKKIVPRDCGCKPCICTVPEVSSV FIFPPKPKDVLTITLTPKVTCVVVDISKDDPEVQFSWFV DDVEVHTAQTQPREEQFNSTFRSVSELPIMHQDWLNGKE FKCRVNSAAFPAPIEKTISKTKGRPKAPQVYTIPPPKEQ MAKDKVSLTCMITDFFPEDITVEWQWNGQPAENYKNTQP IMNTNGSYFVYSKLNVQKSNWEAGNTFTCSVLHEGLHNH HTEKSLSHSPGK (SEQ ID NO: 33) |
| muFR1-13HC | QVQLKESGPDLVAPSQSLSITCTVSGFSLSRYSVHWIRQ PPGKGLEWLGMIWSGGNTDYNSVFKSRLNITKDNSKSQV FLKMNSLQTDDTAIYYCATFDGKVSWFAYWGQGTLVTVS AAKTTPPSVYPLAPGCGDTTGSSVTLGCLVKGYFPESVT VTWNSGSLSSSVHTFPALLQSGLYTMSSSVTVPSSTWPS QTVTCSVAHPASSTTVDKKLEPSGPISTINPCPPCKECH KCPAPNLEGGPSVFIFPPNIKDVLMISLTPKVTCVVVDV SEDDPDVQISWFVNNVEVHTAQTQTHREDYNSTIRVVST LPIQHQDWMSGKEFKCKVNNKDLPSPIERTISKIKGLVR APQVYILPPPAEQLSRKDVSLTCLVVGFNPGDISVEWTS NGHTEENYKDTAPVLDSDGSYFIYSKLNMKTSKWEKTDS FSCNVRHEGLKNYYLKKTISRSPGK (SEQ ID NO: 34) |
| muFR1-53HC | QVQLQQSGPELVRPGASVKMSCKASGYKFTDYDISWVLQ RTGQGLEWIGEIYPGSGRTYYNERFKGKATLTADKSSNT VYMQLSSLTSEDSAVYFCASSYYYGTNSPFAYWGQGTTL TVSSAKTTPPSVYPLAPGSAAQTNSMVTLGCLVKGYFPE PVTVTWNSGSLSSGVHTFPAVLESDLYTLSSSVTVPSSM RPSETVTCNVAHPASSTKVDKKIVPRDCGCKPCICTVPE VSSVFIFPPKPKDVLTITLTPKVTCVVVDISKDDPEVQF SWFVDDVEVHTAQTQPREEQFNSTFRSVSELPIMHQDWL NGKEFKCRVNSAAFPAPIEKTISKTKGRPKAPQVYTIPP PKEQMAKDKVSLTCMITDFFPEDITVEWQWNGQPAENYK SNTQPIMNTNGYFVYSKLNVQKSNWEAGNTFTCSVLHEG LHNHHTEKSLSHSPGK (SEQ ID NO: 35) |
| muFR1-62HC | QVQLQQSGAELARPGASVKMSCKASGYTFTTYTMHWVKQ RPGQGLEWIAYINPTSGYNNYNQKFKEKATLTADKSSST AYMQLTSLTSEDSAVYYCASGGAYGRRPVDYWGQGTSVT VSSAKTTPPSVYPLAPGSAAQTNSMVTLGCLVKGYFPE VTVTWNSGSLSSGVHTFPAVLESDLYTLSSSVTVPSSMR PSETVTCNVAHPASSTKVDKKIVPRDCGCKPCICTVPEV SSVFIFPPKPKDVLTITLTPKVTCVVVDISKDDPEVQFS WFVDDVEVHTAQTQPREEQFNSTFRSVSELPIMHQDWLN GKEFKCRVNSAAFPAPIEKTISKTKGRPKAPQVYTIPPP KEQMAKDKVSLTCMITDFFPEDITVEWQWNGQPAENYKN TQPIMNTNGSYFVYSKLNVQKSNWEAGNTFTCSVLHEGL HNHHTEKSLSHSPGK (SEQ ID NO: 36) |

TABLE 6

Full-length light chain amino acid sequences

| Antibody | Full-length Light Chain Amino Acid Sequence (SEQ ID NO) |
|---|---|
| muFR1-9LC | DIVLTQSPATLSVTPGDSVSLSCRASQSINNNLHWYQQKS HESPRLLIKYASQSISGIPSRFSGSGSGTDFTLSINSVET EDFGMYFCQQSNSWPQVTFGAGTKLELKRADAAPTVSIFP PSSEQLTSGGASVVCFLNNFYPKDINVKWKIDGSERQNGV LNSWTDQDSKDSTYSMSSTLTLTKDEYERHNSYTCEATHK TSTSPIVKSFNRNEC (SEQ ID NO: 37) |

TABLE 6-continued

Full-length light chain amino acid sequences

| Antibody | Full-length Light Chain Amino Acid Sequence (SEQ ID NO) |
|---|---|
| muFR1-13LC | SIVMTQTPKFLLVSTGDRFTITCKASQSVSNDVLWYQQKP GQSPKLLIYYAYNRYSGVPDRFTGSGYGTDFTFTITTVQS EDLAVYFCQQDHSSPFTFGSGTKLEIKRADAAPTVSIFPP SSEQLTSGGASVVCFLNNFYPKDINVKWKIDGSERQNGVL NSWTDQDSKDSTYSMSSTLTLTKDEYERHNSYTCEATHKT STSPIVKSFNRNEC (SEQ ID NO: 38) |
| muFR1-53LC | DIQMTQTTSSLSASLGDRVTISCRASQDISNYLHWYQRKP DGTVKLLVYYSRLQSGVPSRFSGSGSGTDYSLTISTNLEQ EDIATYFCQQGNSLPPTFGSGTKLEIKRADAAPTVSIFPP SSEQLTSGGASVVCFLNNFYPKDINVKWKIDGSERQNGVL NSWTDQDSKDSTYSMSSTLTLTKDEYERHNSYTCEATHKT STSPIVKSFNRNEC (SEQ ID NO: 39) |
| muFR1-62LC | DIVMTQSQKFMSISVGDRVSVTCKASQNVGTNVAWYQQKP GQSPKTLIYASSRYSGVPDRFTGSGSGTDFTLTISNVSQS EDLADYFCHQYNSYPYTFGGGTKLEIKRADAAPTVSIFPP SSEQLTSGGASVVCFLNNFYPKDINVKWKIDGSERQNGVL NSWTDQDSKDSTYSMSSTLTLTKDEYERHNSYTCEATHKT STSPIVKSFNRNEC (SEQ ID NO: 40) |

Also provided are polypeptides that comprise: (a) a polypeptide having at least about 90% sequence identity to SEQ ID NOs:33-36; and/or (b) a polypeptide having at least about 90% sequence identity to SEQ ID NOs:37-40. In certain embodiments, the polypeptide comprises a polypeptide having at least about 95%, at least about 96%, at least about 97%, at least about 98%, or at least about 99% sequence identity to SEQ ID NOs:33-40. Thus, in certain embodiments, the polypeptide comprises (a) a polypeptide having at least about 95% sequence identity to SEQ ID NOs:33-36, and/or (b) a polypeptide having at least about 95% sequence identity to SEQ ID NOs:37-40. In certain embodiments, the polypeptide comprises (a) a polypeptide having the amino acid sequence of SEQ ID NOs:33-36; and/or (b) a polypeptide having the amino acid sequence of SEQ ID NOs:37-40. In certain embodiments, the polypeptide is an antibody and/or the polypeptide specifically binds FOLR1. In certain embodiments, the polypeptide is a murine, chimeric, or humanized antibody that specifically binds FOLR1. In certain embodiments, the polypeptide having a certain percentage of sequence identity to SEQ ID NOs:33-40 differs from SEQ ID NOs:33-40 by conservative amino acid substitutions only.

The affinity or avidity of an antibody for an antigen can be determined experimentally using any suitable method well known in the art, e.g., cytometry (including flow cytometry), enzyme-linked immunoabsorbent assay (ELISA), or radio-immunoassay (RIA), or kinetics (e.g., surface plasmon resonance spectroscopy (BIACORE™) analysis). Direct binding assays as well as competitive binding assay formats can be readily employed. (See, for example, Berzofsky, et al., "Antibody-Antigen Interactions," In Fundamental Immunology, Paul, W. E., Ed., Raven Press: New York, N.Y. (1984); Kuby, Janis Immunology, W.H. Freeman and Company: New York, N.Y. (1992); and methods described herein. The measured affinity of a particular antibody-antigen interaction can vary if measured under different conditions (e.g., salt concentration, pH, temperature). Thus, measurements of affinity and other antigen-binding parameters (e.g., KD or Kd, $K_{on}$, $K_{off}$) are made with standardized solutions of antibody and antigen, and a standardized buffer, as known in the art and such as the buffer described herein.

In one aspect, binding assays can be performed using cytometry (e.g., flow cytometry) on cells expressing the FOLR1 antigen on the surface. For example, FOLR1-positive cells such as SKOV3 were incubated with varying concentrations of anti-FOLR1 antibodies using $1\times10^5$ cells per sample in 100 μL FACS buffer (RPMI-1640 medium supplemented with 2% normal goat serum). Then, the cells were pelleted, washed, and incubated for 1 h with 100 μL of FITC-conjugated goat-anti-mouse or goat-anti-human IgG-antibody (such as is obtainable from, for example Jackson Laboratory, 6 μg/mL in FACS buffer). The cells were pelleted again, washed with FACS buffer and resuspended in 200 μL of PBS containing 1% formaldehyde. Samples were acquired, for example, using a FACSCalibur flow cytometer with the HTS multiwell sampler and analyzed using CellQuest Pro (all from BD Biosciences, San Diego, US). For each sample the mean fluorescence intensity for FL1 (MFI) was exported and plotted against the antibody concentration in a semi-log plot to generate a binding curve. A sigmoidal dose-response curve is fitted for binding curves and EC50 values are calculated using programs such as GraphPad Prism v4 with default parameters (GraphPad software, San Diego, Calif.). EC50 values can be used as a measure for the apparent dissociation constant "Kd" or "KD" for each antibody.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g., radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies.

Alternatively monoclonal antibodies can also be made using recombinant DNA methods as described in U.S. Pat. No. 4,816,567. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the human FOLR1 is a humanized antibody. In certain embodiments, such antibodies are used therapeutically to reduce antigenicity and HAMA (human anti-mouse antibody) responses when administered to a human subject.

Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing FOLR1 binding. Accordingly, part or all of the non-human or human CDR sequences are maintained while the non-human sequences of the variable and constant regions can be replaced with human or other amino acids.

Antibodies can also optionally be humanized, resurfaced, engineered or human antibodies engineered with retention of high affinity for the antigen FOLR1 and other favorable biological properties. To achieve this goal, humanized (or human) or engineered anti-FOLR1 antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as FOLR1. In this way, framework (FR) residues can be selected and combined from the consensus and import sequences so that the desired antibody characteristic, such as increased affinity for the target antigen(s), is achieved.

Humanization, resurfacing or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Roguska et al., Proc. Natl. Acad. Sci., USA, 91(3):969-973 (1994), Roguska et al., Protein Eng. 9(10):895-904 (1996), U.S. Pat. Nos. 5,639,641, 5,723, 323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567; PCT/US98/16280; US96/18978; US91/09630; US91/05939; US94/01234; GB89/01334; GB91/01134; GB92/01755; WO90/14443; WO90/14424; WO90/14430; EP 229246; U.S. Pat. Nos. 7,557,189; 7,538,195; and 7,342,110, each of which is entirely incorporated herein by reference, including the references cited therein.

In certain alternative embodiments, the antibody to FOLR1 is a human antibody. Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety). Affinity maturation strategies and chain shuffling strategies (Marks et al., 1992, Bio/Technology 10:779-783, incorporated by reference in its entirety) are known in the art and can be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545, 807; 5,545,806; 5,569,825; 5,625,126; 5,633,425; and 5,661, 016.

This invention also encompasses bispecific antibodies that specifically recognize a human folate receptor 1. Bispecific antibodies are antibodies that are capable of specifically recognizing and binding at least two different epitopes. The different epitopes can either be within the same molecule (e.g., the same human folate receptor 1) or on different molecules, for example, the antibodies can specifically recognize and bind a human folate receptor 1 as well as, for example, 1) an effector molecule on a leukocyte such as a T-cell receptor (e.g., CD3) or Fc receptor (e.g., CD64, CD32, or CD16) or 2) a cytotoxic agent as described in detail below.

Exemplary bispecific antibodies can bind to two different epitopes, at least one of which originates in a polypeptide of the invention. Alternatively, an anti-antigenic arm of an immunoglobulin molecule can be combined with an arm which binds to a triggering molecule on a leukocyte such as a T cell receptor molecule (e.g., CD2, CD3, CD28, or B7), or Fc receptors for IgG so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp.

Med. 175:217-225; Kostelny et al., 1992, J. Immunol. 148: 1547-1553; Gruber et al., 1994, J. Immunol. 152:5368; and U.S. Pat. No. 5,731,168). Antibodies with more than two valencies are also contemplated. For example, trispecific antibodies can be prepared (Tutt et al., J. Immunol. 147:60 (1991)). Thus, in certain embodiments the antibodies to FOLR1 are multispecific.

In certain embodiments are provided an antibody fragment to, for example, increase tumor penetration. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain embodiments, antibody fragments are produced recombinantly. Fab, Fv, and scFv antibody fragments can all be expressed in and secreted from E. coli or other host cells, thus allowing the production of large amounts of these fragments. Such antibody fragments can also be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

According to the present invention, techniques can be adapted for the production of single-chain antibodies specific to human folate receptor 1 (see U.S. Pat. No. 4,946,778). In addition, methods can be adapted for the construction of Fab expression libraries (Huse, et al., Science 246:1275-1281 (1989)) to allow rapid and effective identification of monoclonal Fab fragments with the desired specificity for a folate 1 receptor, or derivatives, fragments, analogs or homologs thereof. Antibody fragments can be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the polypeptides of a human FOLR1. In this regard, the variable region can comprise or be derived from any type of mammal that can be induced to mount a humoral response and generate immunoglobulins against the desired tumor associated antigen. As such, the variable region of the modified antibodies can be, for example, of human, murine, non-human primate (e.g., cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and in certain embodiments from an antibody from a different species. It may not be necessary to replace all of the CDRs with the complete CDRs from the donor variable region to transfer the antigen-binding capacity of one variable domain to another. Rather, it may only be necessary to transfer those residues that are necessary to maintain the activity of the antigen-binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein can comprise alterations or modifications to one or more of the three heavy chain constant domains (CH1, CH2 or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ΔCH2 constructs). In some embodiments, the omitted constant region domain will be replaced by a short amino acid spacer (e.g., 10 residues) that provides some of the molecular flexibility typically imparted by the absent constant region.

It will be noted that in certain embodiments, the modified antibodies can be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic, or even omitted altogether, so as to maintain the desired biochemical qualities of the modified antibodies.

Besides the deletion of whole constant region domains, it will be appreciated that the antibodies of the present invention can be provided by the partial deletion or substitution of a few or even a single amino acid. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g., complement C1Q binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. Certain embodiments can comprise the addition of one or more amino acids to the constant region to enhance desirable characteristics such as decreasing or increasing effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The polypeptides of the present invention can be recombinant polypeptides, natural polypeptides, or synthetic polypeptides comprising an antibody, or fragment thereof, against a human FOLR1. It will be recognized in the art that some amino acid sequences of the invention can be varied without significant effect of the structure or function of the protein. Thus, the invention further includes variations of the polypeptides which show substantial activity or which include regions of an antibody, or fragment thereof, against a human folate receptor protein. Such mutants include deletions, insertions, inversions, repeats, and type substitutions.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g., Zoeller et al., Proc. Nat'l. Acad. Sci. USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against human FOLR1. Recombinant expression vectors are replicable DNA constructs which have synthetic or cDNA-derived DNA fragments encoding a polypeptide chain of an anti-FOLR1 antibody, or fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of a FOLR1-binding polypeptide or antibody (or a FOLR1 protein to use as an antigen) include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a FOLR1-binding agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005, each of which is hereby incorporated by reference herein in its entirety.

IV. Polynucleotides

In certain embodiments, the invention encompasses polynucleotides comprising polynucleotides that encode a polypeptide that specifically binds a human FOLR1 receptor or a fragment of such a polypeptide. For example, the invention provides a polynucleotide comprising a nucleic acid sequence that encodes an antibody to a human FOLR1 or encodes a fragment of such an antibody. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (antisense) strand. In some embodiments, the polynucleotide is a cDNA or a DNA lacking one more endogenous introns.

In some embodiments, a polynucleotide is a non-naturally occurring polynucleotide. In some embodiments, a polynucleotide is recombinantly produced.

In certain embodiments, the polynucleotides are isolated. In certain embodiments, the polynucleotides are substantially pure. In some embodiments, a polynucleotide is purified from natural components.

The invention provides a polynucleotide comprising a polynucleotide encoding a polypeptide comprising a sequence selected from the group consisting of SEQ ID NOs: 1-40. Also provided is a polynucleotide encoding a polypeptide having at least about 95%, at least about 96%, at least about 97%, at least about 98%, or at least about 99% sequence identity to SEQ ID NOs: 1-40.

In certain embodiments the polynucleotides comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used.

The present invention further relates to variants of the hereinabove described polynucleotides encoding, for example, fragments, analogs, and derivatives.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as $E.\ coli$).

Vectors and cells comprising the polynucleotides described herein are also provided.

V. Detection

When a sandwich ELISA format is used, the capture antibody will be unlabeled. The detection antibody will be either directly labeled, or detected indirectly by addition (after washing off excess detection antibody) of a molar excess of a second, labeled antibody directed against the first antibody.

The label used for the detection antibody is any detectable functionality that does not interfere with the binding of the FOLR1 antibodies. Examples of suitable labels are those numerous labels known for use in immunoassay, including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, biotin/streptavidin, biotin/Streptavidin-β-galactosidase with MUG, spin labels, bacteriophage labels, stable free radicals, and the like. As noted above, the fluorimetric detection is one example.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al. Nature 144:945 (1962); David et al. Biochemistry 13:1014-1021 (1974); Pain et al. J. Immunol. Methods 40:219-230 (1981); and Nygren J. Histochem. and Cytochem. 30:407-412 (1982). In certain embodiments, labels herein are fluorescent to increase amplification and sensitivity to 8 pg/ml, more preferably biotin with streptavidin-β-galactosidase and MUG for amplifying the signal. In certain embodiments, a colorimetric label is used, e.g., where the detectable antibody is biotinylated and the detection means is avidin or streptavidin-peroxidase and 3,3',5,5'-tetramethyl benzidine.

The conjugation of such label, including the enzymes, to the antibody is a standard manipulative procedure for one of ordinary skill in immunoassay techniques. See, for example, O'Sullivan et al. "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166.

Following the addition of last labeled antibody, the amount of bound antibody is determined by removing excess unbound labeled antibody through washing and then measuring the amount of the attached label using a detection method appropriate to the label, and correlating the measured amount with the amount of shed FOLR1 or FOLR1 on circulating tumor cells in the biological sample. For example, in the case of enzymes, the amount of color developed and measured will be a direct measurement of the amount of shed FOLR1 present or FOLR1 present on circulating tumor cells. Specifically, if HRP is the label, the color can be detected using the substrate 3,3',5,5'-tetramethyl benzidine at 450 nm absorbance.

VI. Circulating Tumor Cell Assays

The anti-FOLR1 antibodies described herein may also be used for the detection of FOLR1 in a circulating tumor cell assay. Circulating tumor cells (CTCs) are cells that have shed into the vasculature from a tumor and circulate in the bloodstream. CTCs are present in circulation in extremely low concentrations. In general, CTC are enriched from patient blood or plasma by various techniques known in the art. CTCs may be stained for specific markers using methods known in the art including, but not limited to, cytometry (e.g., flow cytometry)-based methods and IHC-based methods. CTCs may be stained for protein markers unique to the tumor cells which allows for the identification and distinction of CTCs from normal blood cells. CTCs may also be stained for FOLR1 using the antibodies of the invention including, but not limited to, FR1-9 and FR1-13. CTC analysis may also include quantitative analysis of the number of CTCs and/or the number of FOLR1 positive CTCs. In the present invention, the FOLR1 antibodies described herein may be used to stain the CTCs isolated from a subject having a cancer to measure the FOLR1 present in the CTCs. An increase in FOLR1 expressing CTCs may help identify the subject as having a cancer that is likely to respond to FOLR1 based therapy or allow for optimization of a therapeutic regimen with a FOLR1 antibody or Immunoconjugate. CTC FOLR1 quantitation can provide information on the stage of tumor, response to therapy and/or disease progression. It can be used as prognostic, predictive or pharmacodimamic biomarker. In addition, staining of CTCs for particular markers including, but not limited to FOLR1, may be used as a liquid biopsy either alone or in combination with additional tumor marker analysis of solid biopsy samples.

VII. Kits

As a matter of convenience, the assay method of this invention can be provided in the form of a kit. Such a kit is a packaged combination including the basic elements of: (a) a first reagent, which can be a capture reagent, comprised of the monoclonal antibodies against human FOLR1; and/or (b) a second reagent which is a detection reagent. The detection reagent can also comprise FOLR1 monoclonal antibodies, but can also comprise detectable (labeled or unlabeled) antibodies that bind to FOLR1. These basic elements are defined hereinabove and in the Examples below.

In one embodiment wherein the first reagent and the second reagent are antibodies, antigen-binding fragments thereof, or polyeptides that bind to FOLR1, the first and second reagents are different antibodies, antigen-binding fragments thereof, or polyeptides. In one embodiment, the first reagent binds to a different FOLR1 epitope than the second FOLR1 reagent. In onen embodiment, neither the first reagent or the second reagent competitively inhibits the binding of an active agent (e.g., a an active agent comprising an huMOv19 antibody or antigen-binding fragment thereof) from binding to FOLR1.

In one embodiment, the kit further comprises a solid support for the capture reagents, which can be provided as a separate element or on which the capture reagents are already immobilized. Hence, the capture antibodies in the kit can be immobilized on a solid support, or they can be immobilized on such support that is included with the kit or provided separately from the kit.

In one embodiment, the capture reagent is coated on a microtiter plate. The detection reagent can be labeled antibodies detected directly or unlabeled antibodies that are detected by labeled antibodies directed against the unlabeled antibodies raised in a different species. Where the label is an enzyme, the kit will ordinarily include substrates and cofactors required by the enzyme, and where the label is a fluorophore, a dye precursor that provides the detectable chromophore. Where the detection reagent is unlabeled, the kit can further comprise a detection means for the detectable antibodies, such as the labeled antibodies directed to the unlabeled antibodies, e.g., in a fluorimetric-detected format. Where the label is an enzyme, the kit will ordinarily include substrates and cofactors required by the enzyme, where the label is a fluorophore, a dye precursor that provides the detectable chromophore, and where the label is biotin, an avidin such as avidin, streptavidin, or streptavidin conjugated to HRP or β-galactosidase with MUG.

In one embodiment, the capture reagent is the FOLR1 antibody FR1-9 and the detection reagent is the FOLR1 antibody FR1-13. In another embodiment, the FR1-13 is biotinylated.

The kit also typically contains instructions for carrying out the assay, and/or FOLR1 protein, or fragments thereof (e.g., FOLR1 extracellular domain or the FOLR1 extracellular domain and all or a part of the GPI linkage domain) as an antigen standard, as well as other additives such as stabilizers, washing and incubation buffers, and the like. In one embodiment, the FOLR1 antigen standard is a FOLR1-Fc immunoadhesin. The kit can also include instructions for detection and scoring of FOLR1 expression.

The components of the kit will be provided in predetermined ratios, with the relative amounts of the various reagents suitably varied to provide for concentrations in solution of the reagents that substantially maximize the sensitivity of the assay. Particularly, the reagents can be provided as dry powders, usually lyophilized, including excipients, which on dissolution will provide for a reagent solution having the appropriate concentration for combining with the sample to be tested.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application.

Example 1

Development of Murine Anti-FOLR1 Antibodies

There were two different immunization/screening series. In the first series, mice were subcutaneously immunized with approximately $5 \times 10^6$ FOLR1-expressing KB cells (American Tissue Culture Collection, ATCC CCL-17). In the second series 300-19 cells expressing human FOLR1 on their surface were used to immunize mice. To make these cells, the human FOLR1 amino acid sequence was obtained from the NCBI website (accession NP_057937), then it was codon optimized and synthesized by Blue Heron biotechnologies, flanked by EcoRI and Xba1 restriction sites to facilitate cloning into the pSRa mammalian expression vector. 300-19 cells, a pre-B cell line derived from a Balb/c mouse (Reth et al., *Nature*, 317:353-355 (1985)), were transfected with the pSRa-FolR1 expression plasmid to stably express high levels of human FOLR1 on the cell surface. Standard immunization protocols known to those of skill, for example, such as those used at ImmunoGen, Inc. were applied for both series. Immunized mice were boosted with antigen three days before being sacrificed for hybridoma generation. Spleens from mice was collected according to standard animal protocols, such as, for example grinding tissue between two sterile, frosted microscopic slides to obtain a single cell suspension in RPMI-1640 medium. The spleen cells were centrifuged, pelleted, washed, and fused with a murine myeloma, such as, for example P3X63Ag8.653 cells (Kearney et al., J. Immunol., 123:1548-1550 (1979)) using polyethylene glycol-1500 (Roche 783 641). The fused cells were resuspended in RPMI-1640 selection medium containing hypoxanthine-aminopterin-thymidine (HAT) (Sigma H-0262) and selected for growth in 96-well flat-bottomed culture plates (Corning-Costar 3596, 0.2 ml of cell suspension per well) at 37° C. with 5% $CO_2$. After 5 days of incubation, 0.1 ml of culture supernatant was removed from each well and replaced with 0.1 ml of RPMI-1640 medium containing hypoxanthine-thymidine (HT)

supplement (Sigma H-0137). Incubation at 37° C. with 5% $CO_2$ was continued until hybridoma clones were ready for antibody screening. Other techniques of immunization and hybridoma production can also be used, including those described in Langone et al. (Eds., "Immunochemical Techniques, Part I", Methods in Enzymology, Academic Press, volume 121, Florida) and Harlow et al. ("Antibodies: A Laboratory Manual"; Cold Spring Harbor Laboratory Press, New York (1988)).

Example 2

Hybridoma Screening and Selection

FOLR1-300-19 cells transfected with human FOLR1 and KB cells were used in the first and second series of screenings correspondently. Culture supernatants from the hybridoma were screened by flow cytometry for secretion of mouse monoclonal antibodies that bind to FOLR1 positive cells, such as FOLR1-expressing 300-19 cells or KB cells, but not to the FOLR1 negative cells, such as non-transfected 300-19 cells. 0.1 ml of hybridoma supernatants was incubated for 3 h with either FOLR1-positive cells or the non-transfected 300-19 cells ($1 \times 10^5$ cells per sample) in 0.1 ml FACS buffer (RPMI-1640 medium supplemented with 2% normal goat serum). Then, the cells were centrifuged, pelleted, washed, and incubated for 1 hour with 0.1 ml of PE-conjugated goat anti mouse IgG-antibody (such as obtainable from, for example Jackson Laboratory, 6 μg/mL in FACS buffer). The cells were centrifuged, pelleted again, washed with FACS buffer and resuspended in 0.2 ml of PBS containing 1% formaldehyde. Cell-associated fluorescence was measured using a FACSCalibur flow cytometer with the HTS multiwell sampler or a FACS array flow cytometer and analyzed using CellQuest Pro (all from BD Biosciences, San Diego, US). Positive hybridoma clones were subcloned by limiting dilution. One subclone from each hybridoma, which showed the same reactivity against FOLR1 as the parental cells by flow cytometry, was chosen for subsequent analysis. Stable subclones were cultured and the isotype of each secreted anti-FOLR1 antibody was identified using commercial isotyping reagents (Roche 1493027). Murine antibodies were protein A purified from cleared hybridoma media as described above. These antibodies were designated FR-1 antibodies.

One clone, muFR1-13, was identified as an anti-FOLR1 clone that (1) did not compete or hinder the binding of Mov19 simultaneously to the same antigen, and (2) had a high binding specificity to the target as demonstrated by common flow cytometry techniques (FIGS. 2A and 2B). These two characteristics were necessary in the development of this assay, and so clone muFR1-13 was chosen for use in the assay.

From the remaining 64 anti-FOLR1 clone panel, a second antibody was required for the assay that held the same criteria as was necessary for muFR1-13. Additionally, the second antibody could not compete or hinder the binding of muFR1-13 simultaneously to the same antigen (i.e., Mov19, muFR1-13 and the final clone must have all distinctly separate epitopes). To satisfy these conditions, a series of competition ELISA experiments were conducted on the remaining panel of 65 anti-folate clones (FIG. 3A). If an antibody shares the same, or sterically similar epitope to the antibody being detected, a reduction in signal is observed (FIG. 3B). Using this method, 5 antibodies of the 64 tested were identified as having epitopes that compete with Mov19, and hence were removed from further consideration.

The same method was repeated substituting Mov19 conjugated Biotin with muFR1-13 conjugated Biotin (FIG. 4). Using this method, 6 additional clones were identified as having epitopes that compete with muFR1-13, and hence were removed from further consideration. Of the remaining 53 clones, 13 more clones were shown to have poor affinity and were removed from consideration.

The remaining 40 clones were screened using a similar ELISA format as shown in FIG. 1. The 40 clones were alternatively coated onto the assay plate in place of muFR1-9 in the diagram, and the resulting binding curves were analyzed shown in FIG. 5. Antibodies that contained the lowest half-maximal response (EC50) were considered to have the highest binding specificity to FOLR1, and thus were chosen as the top candidates for the assay. The binding affinities of the top 4 clones assayed in this method ranged from $\sim 1\text{-}5 \times 10^{-9}$ M once new, higher quality materials were available for testing.

Example 3

Murine Monoclonal Antibody Purification

Antibodies were purified from hybridoma subclone supernatants using standard methods, such as, for example Protein A or G chromatography (HiTrap Protein A or G HP, 1 mL, Amersham Biosciences). Briefly, supernatant was prepared for chromatography by the addition of 1/10 volume of 1 M Tris/HCl buffer, pH 8.0. The pH-adjusted supernatant was filtered through a 0.22 μm filter membrane and loaded onto column equilibrated with binding buffer (PBS, pH 7.3). The column was washed with binding buffer until a stable baseline was obtained with no absorbance at 280 nm. Antibody was eluted with 0.1 M acetic acid buffer containing 0.15 M NaCl, pH 2.8, using a flow rate of 0.5 mL/min. Fractions of approximately 0.25 mL were collected and neutralized by the addition of 1/10 volume of 1M Tris/HCl, pH 8.0. The peak fraction(s) was dialyzed overnight twice against 1×PBS and sterilized by filtering through a 0.2 μm filter membrane. Purified antibody was quantified by absorbance at $A_{280}$.

Example 4

Binding Characterization by Flow Cytometry

Binding specificity was tested by flow cytometry using purified antibodies. Each antibody was incubated for 3 hours with either FOLR1-expressing 300-19 cells or the non-transfected 300-19 cells ($1 \times 10^5$ cells per sample) in 0.1 ml FACS buffer (RPMI-1640 medium supplemented with 2% normal goat serum). Then, the cells were pelleted, washed, and incubated for 1 hour with 0.1 ml of FITC-conjugated goat anti-mouse IgG-antibody (such as is obtainable from, for example Jackson Laboratory, 6 μg/mL in FACS buffer). The cells were pelleted again, washed with FACS buffer and resuspended in 200 μL of PBS containing 1% formaldehyde. Samples were acquired using a FACSCalibur flow cytometer with the HTS multiwell sampler or a FACS array flow cytometer and analyzed using CellQuest Pro (all from BD Biosciences, San Diego, US). The FACS histograms of anti-FOLR1 antibodies showed a fluorescence shift, while parental 300-19 cells did not. Also, no significant fluorescence shift was detected when either of the cell lines was incubated only with FITC conjugated goat anti-human IgG-antibody alone.

Example 5

Cloning and Sequencing of the VL and VH Regions of muFR1-9 and FR1-53

Total cellular RNA was prepared from $5 \times 10^6$ hybridoma cells using an RNeasy kit (QIAgen) according to the manufacturer's protocol. cDNA was subsequently synthesized from total RNA using the SuperScript II cDNA synthesis kit (Invitrogen). The procedure for the first round degenerate PCR reaction on the cDNA derived from hybridoma cells was based on methods described in Wang et al. (2000) J Immunol Methods. January 13; 233(1-2):167-77) and Co et al. (1992) J. Immunol. February 15; 148(4):1149-54)). VH sequences were amplified by PCR using the following degenerate primers: EcoMH1 CTTCCGGAATTCSARGTNMAGCTGSAG-SAGTC (SEQ ID NO:45), EcoMH2 CTTCCGGAATTC-SARGTNMAGCTGSAGSAGTCWGG (SEQ ID NO:41), and BamIgG1 GGAGGATCCATAGACAGATGGGGGT-GTCGTTTTGGC (SEQ ID NO:42). VL sequences were amplified by PCR using the following degenerate primers: SacIMK GGAGCTCGAYATTGTGMTSACMCARCT-MCA (SEQ ID NO:43) and HindKL TATAGAGCT-CAAGCTTGGATGGTGGGAAGATGGATA-CAGTTGGTGC (SEQ ID NO:44). (Mixed bases are defined as follows: N=G+A+T+C, S=G+C, Y=C+T, M=A+C, R=A+G, W=A+T).

The PCR reaction mixtures were then run on a 1% low melt agarose gel, the 300 to 400 bp bands were excised, purified using Zymo DNA mini columns, and sent to Agencourt Biosciences for sequencing. The respective 5' and 3' PCR primers were used as sequencing primers to sequence the variable region cDNAs from both directions. The amino acid sequences of VH and VL regions were obtained by translating the DNA sequencing results with Vector NTI software.

The preliminary variable region cDNA sequences included 5' end sequences derived from the degenerate PCR primers rather than the murine antibody mRNA so sequence comparisons with mouse antibody germline sequences facilitated the identification and removal of these sequencing artifacts. The NCBI IgBlast site (www.ncbi.nlm.nih.gov/igblast/) was utilized to search for the murine germline sequences from which the preliminary antibody cDNA sequences were derived and the primer derived 5' end sequences were replaced with the corresponding germline sequences. The cleaned up variable region sequences were then combined with the NCBI reference sequences for the murine kappa and IgG1 constant regions (accessions AJ294736.1 and D78344.1 respectively) to assemble expected full length murine antibody sequences. The molecular weight of the expected murine FR1-9 and FR1-53 light and heavy chains were then calculated and compared with the mass measured by liquid chromatography/mass spectrophotometric analysis (LC/MS).

The initial efforts to sequence the murine FR1-9 light chain, following the methods described above, proved unsuccessful so alternative methods were employed. The light chain sequences of hybridomas related to FR1-9 were used to design the KS77LClead PCR primer (ttttgagctctggattccagc-ctccagaggt) to anneal to the presumed leader sequence of the FR1-9 light chain framework. This leader primer PCR reaction and sequencing was performed as described above and yielded a complete cDNA sequence encoding a light chain that matches the FR1-9 light chain mass measured by LC/MS.

Example 6

FOLR1 Fc Fusion Control Sample

A human folate receptor 1 Fc fusion molecule was constructed as an alternative soluble antigen source to the human folate binding protein typically derived from human milk. The amino-terminus of the human FolR1 cDNA, described in the immunization example above, was excised from the full length sequence with an EcoRI and Pst1 restriction digest. This fragment contained the cDNA encoding the 233 amino acids from the N terminal signal peptide to the residues just up stream of the GPI linkage site of huFolR1 (NCBI accession NM_016731.2). A Pst1 to BamHI oligonucleotide linker facilitated the cloning of the FolR1 fragment in-frame with the murine IgG2A hinge, CH2, and CH3 antibody constant region sequences (NCBI accession P01863) in the pmuFc2ANL-EK mammalian expression plasmid. The human FolR1-Fc fusion protein was then expressed by transient or stable transfections in mammalian host cell lines such as HEK-293T or CHO cells. Since the 475 amino acid fusion protein contains the murine IgG2A constant region, the molecule was purified following the standard murine antibody purification procedures described above.

Example 7

Shed Antigen ELISA Assay

To assure that materials were continuously performing as expected, all antibodies were screened for binding by both ELISA and flow cytometry methods known in the art. Flow cytometry was performed using FOLR1 expressing human T47D cells cultured using in-vitro cell culture techniques known in the art. The antibodies were bound to these cells and detected indirectly using a goat anti-murine Alexa-fluor 488 detection antibody on a FACScalibur machine (FIG. 6A-B). The same methods were applied to the other antibodies, and it was determined that the final selected antibodies FR1-13 and FR1-9 showed an approximately $1-3\times10^{-9}$ M, and $2-4\times10^{-9}$ binding affinity respectively by both methods.

It is important that the assay detect only FOLR1, and not FOLR2 or especially FOLR3 (commonly found as a shed protein in human plasma), since Mov19 is specific for only FOLR1. To determine this, the top four clones were screened by commercially available ELISA kits (FIGS. 7A-B). The positive control detection antibody shows a positive signal above background indicating detection of FOLR2 or FOLR3. The remaining antibodies (FR1-9, FR1-53, FR1-62, FR1-64, & Mov19) do not produce a signal in the assay, and therefore do not bind to FOLR2 or FOLR3.

Additionally, the presence of folic acid bound to FOLR1 could potentially obscure the epitope of the chosen antibodies. To assure that the assay would detect FOLR1 in physiological amounts of folic acid in human blood, folic acid was pre-incubated with the FOLR1 standard purified protein and added to the assay plate. As shown in FIG. 8, the presence of folic acid had negligible impact on the detection affinity of the assay compared to positive controls containing no folic acid. Therefore, it was concluded that the assay could detect FOLR1 even in the presence of bound folic acid.

Since none of the top four antibody clones (FR1-9, 53, 62, or 64) showed interference with the binding of Mov19 or FR1-13, and because no adverse binding properties were observed in the presence of FOLR2, FOLR3, or folic acid, these four candidates of the original 64 clones were viable for use in the assay. Of these four clones, it was determined that clone FR1-9 and FR1-53 had higher binding affinities compared to FR1-62 and FR1-64. Production of the FR1-53 antibody from its parent hybridoma produced consistently poorer yield, and hence clone FR1-9 was chosen for its ease of antibody production, higher antibody purity, and percent monomer.

In efforts to optimize the assay, a systematic approach was used in which concentrations of FR1-9, Biotinylated FR1-13, Strp-HRP, and respective incubation times were optimized using FOLR1-Fc fusion protein as the antigen standard. The FOLR1-Fc fusion is a fusion peptide of huFOLR1 and murine IgG2A hinge, CH2, CH3. Criteria for establishing optimized conditions were reproducible signals with a high signal to noise ratio, minimal matrix effects in human plasma samples, high repeatability and precision and lowest limit of detection.

More specifically, the assay was performed by coating an assay plate with muFR1-9 at 2 µg/mL and incubated. After blocking with a non-specific protein, samples (including antigen standards and human plasma samples) were added to the assay plates to incubate. Plates were then washed and muFR1-13b detection antibody (2 µg/mL) was added to each well. Plates were washed again before adding a molar excess of streptavidin conjugated Horse Radish Peroxidase (1:5,000). The plate was washed again before 3,3',5,5'-Tetramethylbenzidine (TMB), was added. TMB reacted with the peroxidase to form a blue color, with an intensity commensurate with the amount of FOLR1 present in the sample. The reaction was stopped with an acid containing solution, which turned the color yellow. The assay was then read on a spectramax plate reader to determine the intensity of the color reaction in each sample (absorbance). When necessary, a sigmoidal dose-response (variable slope) curve was generated with Graphpad Prism v5.04 software using the 4PL equation: $Y=Bottom+(Top-Bottom)/1+10^{\wedge}((LogEC50-X)*Hill Slope}$ for all dilution series.

To determine the adequacy of the final ELISA format, human ovarian cancer patient plasma and non-tumor sourced human ascites samples were tested. In non-tumor bearing patients with ascites fluid, 15 samples were analyzed for the presence of FOLR1. No FOLR1 was detected by the assay in all 15 samples, and no false positives were observed due to matrix effects (FIG. 9). Alternatively, these ascites samples had purified human FOLR1 protein added into them, and the subsequent detection was performed. Recovery of the FOLR1 protein as determined by the assay was greater than 85% of the known added amount (not shown). Therefore, it was assumed there were no interfering proteins in non-tumor associated human ascites fluid even with no dilution of the sample.

The same analysis was performed in pooled normal human plasma (pooled was n=10 patients per lot). No endogenous FOLR1 was detected by the assay, and no interfering proteins were discovered in non-diluted samples of human plasma with added purified huFOLR1-Fc protein (FIG. 10). Samples of human ovarian cancer plasma were provided by the Dana Farber Cancer Institute or Mass General Hospital. Of the 72 samples analyzed to date, 7 samples were identified as having detectable levels of FOLR1 with a range of 0.7 to 30.6 nM. A representative analysis of this data is shown in FIG. 11. Here, three of eight samples contained detectable levels of FOLR1 showing 0.74, 0.91 and 30.6 nM for samples PB105, PB106, and PB109 respectively. The method for interpolation of this data from a relevant standard curve generated using huFOLR1-Fc is shown in FIG. 12.

Example 8

Circulating Tumor Cell Assay

Three cell lines with varying levels of FOLR1 expression were selected as representative of high expression (KB), low expression (OVCAR3), and no expression (A549). Unlabeled FR1-9 and FR1-13, as well as a commercial anti-FOLR1 antibody ("commercial FRA"), were titrated, and optimal titrations were determined for each of the antibodies using laser scanning cytometry (LSC) detection on the selected cell lines. Fluorescence was measured as mean fluorescence intensity (MFI) and is shown in FIG. 13. All three antibodies showed expression of folate receptor in KB cells. Optimal dilutions were identified for each antibody as follows: 1:5 for commercial FRA, 1:100 for muFR1-9, and 1:200 for muFR1-13. Of the antibodies tested, the commercial antibody gave the best signal to background ration (8.0 versus 4.07 (muFR1-9) and 4.19 (muFR1-13)), but only muFR1-9 showed a signal in the OVCAR3 cells (approximately 30% more signal than A549 cells). See FIG. 14.

For applications that include monitoring the treatment or efficacy with IMGN853, the antibody selected for use in a CTC assay should not compete with the antibody component of IMGN853 (i.e., huMov19 (M9346A)) for binding to FOLR1. Competition assays were conducted to determine if any of the antibodies competed with IMGN853 antibody for binding to FOLR1. For these assays, A549 (negative) and KB (high expressors) cells were treated with the M9346A antibody or vehicle alone. Cells were then washed and stained with each of the three antibodies, and expression was analyzed using LSC. The results are provided in FIG. 15. Light bars (left) represent vehicle alone, and dark bars (right) represent IMGN853 treated cells. If competition with the therapeutic IMGN853 exists, then the dark bar (right) will be lower than the light bar (left) in the KB cells. The results in FIG. 15 show that the commercial FRA antibody competes for binding with IMGN853 (~66% drop in FRA signal), while the muFR1-9 and muFR1-13 antibodies were not affected by IMGN853 treatment.

Taken together, these results demonstrate that muFR1-9 and muFR1-13 did not compete with IMGN853, thereby making them the more desirable candidates for use in an assay that monitors FOLR1 levels in a bodily fluid (e.g., blood or plasma), circulating tumor cell, or tissue sample, after treatment with IMGN853. In addition, muFR1-9 was more sensitive and demonstrated the unique ability to detect expression in OVCAR3 cells which had low levels of expression and is the preferred candidate antibody for these types of assays.

Example 9

Detection of FOLR1 in Circulating Tumor Cells (CTCs) Isolated from NSCLC and Ovarian Cancer Patients Blood samples are drawn from ovarian cancer or NSCLC cancer patients at the following time points: Screening (up to 28 days prior to baseline); Baseline; Prior to Cycle 3; and End of Cycle 4. CTCs are enriched from the samples and stained for CK, CD45, nuclei, and FOLR1 using the antibodies and dilutions described in Example 8, above. The number of CTCs (i.e., CK+/CD45-nucleated cells), the number of CK−/CD45-nucleated cells, the expression of FOLR1 on CTCs, the number of CK−/CD45-nucleated cells, and the percentage of FOLR1 positive CTCs and CK−/CD45-nucleated cells are determined by LSC for each sample. The data is used to determine FOLR1 expression levels in CTCs at various time points during the Phase I clinical trial for IMGN853.

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

What is claimed is:

1. An antibody or antigen-binding fragment thereof that specifically binds to the same FOLR1 epitope as, and competitively inhibits the binding to FOLR1 of, an antibody selected from the group consisting of:
  (a) an antibody comprising the variable heavy chain polypeptide of SEQ ID NO:25 and the variable light chain polypeptide of SEQ ID NO:29;
  (b) an antibody comprising the variable heavy chain polypeptide of SEQ ID NO:26 and the variable light chain polypeptide of SEQ ID NO:30;
  (c) an antibody comprising the variable heavy chain polypeptide of SEQ ID NO:27 and the variable light chain polypeptide of SEQ ID NO:31; and
  (d) an antibody comprising the variable heavy chain polypeptide of SEQ ID NO:28 and the variable light chain polypeptide of SEQ ID NO:32.

2. An immunoassay kit for detecting FOLR1 protein in a sample, the kit comprising: (a) a first reagent, wherein the first reagent is the antibody or antigen-binding fragment thereof of claim 1, and (b) a second reagent, wherein the second reagent is a second antibody or antigen-binding fragment that specifically binds to FOLR1.

3. The immunoassay kit of claim 2, wherein the second reagent comprises a chromogenic detection agent, a fluorogenic detection agent, an enzymatic detection agent, or an electrochemiluminescent detection reagent.

4. The immunoassay kit of claim 2, wherein the second reagent is biotinylated.

5. The immunoassay kit of claim 2, wherein the first reagent is immobilized on a solid support.

6. An antibody or antigen-binding fragment thereof that specifically binds to FOLR1, wherein said antibody or antigen-binding fragment thereof comprises a heavy chain variable domain and a light chain variable domain, wherein:
  (a) the heavy chain variable domain comprises the CDR1, CDR2, and CDR3 sequences of SEQ ID NOs: 1, 2, and 3, respectively, and the light chain variable domain comprises the CDR1, CDR2, and CDR3 sequences of SEQ ID NOs: 13, 14, and 15, respectively;
  (b) the heavy chain variable domain comprises the CDR1, CDR2, and CDR3 sequences of SEQ ID NOs: 4, 5, and 6, respectively, and the light chain variable domain comprises the CDR1, CDR2, and CDR3 sequences of SEQ ID NOs: 16, 17, and 18;
  (c) the heavy chain variable domain comprises the CDR1, CDR2, and CDR3 sequences of SEQ ID NOs: 7, 8, and 9, respectively, and the light chain variable domain comprises the CDR1, CDR2, and CDR3 sequences of SEQ ID NOs: 19, 20, and 21; or
  (d) the heavy chain variable domain comprises the CDR1, CDR2, and CDR3 sequences of SEQ ID NOs: 10, 11, and 12, respectively, and the light chain variable domain comprises the CDR1, CDR2, and CDR3 sequences of SEQ ID NOs: 22, 23, and 24.

7. The antibody or antigen-binding fragment thereof of claim 6, wherein said antibody or antigen-binding fragment thereof is murine, humanized, chimeric, resurfaced, or human.

8. An immunoassay kit for detecting FOLR1 protein in a sample, the kit comprising: (a) a first reagent, wherein the first reagent is the antibody or antigen-binding fragment of claim 6 and wherein said antibody or antigen-binding fragment comprises the heavy chain variable domain CDR1, CDR2, and CDR3 sequences of SEQ ID NOs: 1, 2, and 3, respectively, and the light chain variable domain CDR1, CDR2, and CDR3 sequences of SEQ ID NOs: 13, 14, and 15, respectively and (b) a second reagent, wherein the second reagent is an antibody or antigen-binding fragment comprising the heavy chain variable domain CDR1, CDR2, and CDR3 sequences of SEQ ID NOs: 4, 5, and 6, respectively, and the light chain variable domain CDR1, CDR2, and CDR3 sequences of SEQ ID NOs: 16, 17, and 18, respectively.

9. The immunoassay kit of claim 8, wherein the second reagent comprises a chromogenic detection agent, a fluorogenic detection agent, an enzymatic detection agent, or an electrochemiluminescent detection reagent.

10. The immunoassay kit of claim 8, wherein the second reagent is biotinylated.

11. The immunoassay kit of claim 8, wherein the first reagent is immobilized on a solid support.

12. An antibody or antigen-binding fragment thereof that specifically binds to the same FOLR1 epitope as, and competitively inhibits the binding of an antibody comprising the variable heavy chain polypeptide of SEQ ID NO:25 and the variable light chain polypeptide of SEQ ID NO:29 to FOLR1.

13. An antibody or antigen-binding fragment thereof that specifically binds to FOLR1, wherein said antibody or antigen-binding fragment thereof comprises the heavy chain variable domain CDR1, CDR2, and CDR3 sequences of SEQ ID NOs: 1, 2, and 3, respectively, and the light chain variable domain CDR1, CDR2, and CDR3 sequences of SEQ ID NOs: 13, 14, and 15, respectively.

14. An antibody or antigen-binding fragment thereof that specifically binds to FOLR1, wherein said antibody or antigen-binding fragment comprises a heavy chain variable domain and a light chain variable domain, wherein the light chain variable domain comprises the sequence set forth in SEQ ID NO:29 and the heavy chain variable domain comprises the sequence set forth in SEQ ID NO:25.

15. An antibody or antigen-binding fragment thereof that specifically binds to FOLR1, wherein said antibody or antigen-binding fragment thereof comprises a heavy chain variable domain and a light chain variable domain, wherein said heavy chain variable domain and said light chain variable domain comprise the sequences set forth in
  (a) SEQ ID NO: 25 and SEQ ID NO:29, respectively;
  (b) SEQ ID NO: 26 and SEQ ID NO:30, respectively;
  (c) SEQ ID NO:27 and SEQ ID NO:31, respectively;
  (d) SEQ ID NO:28 and SEQ ID NO:32, respectively.

* * * * *